US011865121B2

(12) United States Patent
Komorowski

(10) Patent No.: US 11,865,121 B2
(45) Date of Patent: Jan. 9, 2024

(54) CHROMIUM CONTAINING COMPOSITIONS FOR IMPROVING HEALTH AND FITNESS

(71) Applicant: Nutrition 21, LLC, Purchase, NY (US)

(72) Inventor: James R. Komorowski, Trumbull, CT (US)

(73) Assignee: Nutrition21, LLC, Saddle Brook, NJ (US)

( * ) Notice: Subject to any disclaimer, the term of this patent is extended or adjusted under 35 U.S.C. 154(b) by 590 days.

(21) Appl. No.: 15/427,471

(22) Filed: Feb. 8, 2017

(65) Prior Publication Data

US 2017/0239267 A1 Aug. 24, 2017

Related U.S. Application Data

(60) Provisional application No. 62/285,014, filed on Feb. 11, 2016.

(51) Int. Cl.
| | | |
|---|---|---|
| A61K 31/555 | (2006.01) |
| A61K 31/718 | (2006.01) |
| A61K 33/24 | (2019.01) |
| A23L 33/165 | (2016.01) |
| A23L 33/17 | (2016.01) |
| A23L 33/125 | (2016.01) |
| A23L 33/16 | (2016.01) |
| A61K 9/08 | (2006.01) |
| A61K 9/14 | (2006.01) |
| A61K 31/198 | (2006.01) |
| A61K 31/732 | (2006.01) |
| A61K 36/899 | (2006.01) |
| A61K 38/01 | (2006.01) |
| A61K 45/06 | (2006.01) |

(52) U.S. Cl.
CPC .......... *A61K 31/555* (2013.01); *A23L 33/125* (2016.08); *A23L 33/16* (2016.08); *A23L 33/165* (2016.08); *A23L 33/17* (2016.08); *A61K 9/08* (2013.01); *A61K 9/14* (2013.01); *A61K 31/198* (2013.01); *A61K 31/718* (2013.01); *A61K 31/732* (2013.01); *A61K 33/24* (2013.01); *A61K 36/899* (2013.01); *A61K 38/018* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | |
|---|---|---|
| 3,939,259 A | 2/1976 | Pescetti |
| 3,965,256 A | 6/1976 | Leslie |
| 4,164,573 A | 8/1979 | Galinsky |
| 4,315,927 A | 2/1982 | Evans |
| 4,421,685 A | 12/1983 | Chance et al. |
| 4,424,057 A | 1/1984 | House |
| 4,476,118 A | 10/1984 | Brange et al. |
| 4,571,391 A | 2/1986 | Riley et al. |
| 4,797,278 A | 1/1989 | Kawai et al. |
| 4,921,877 A | 5/1990 | Cashmere et al. |
| 4,923,855 A | 5/1990 | Jensen |
| 4,954,492 A | 9/1990 | Jensen |
| 5,023,252 A | 6/1991 | Hseih |
| 5,028,599 A | 7/1991 | Hunter |
| 5,032,608 A | 7/1991 | Dudrick |
| 5,053,389 A | 10/1991 | Balschmidt et al. |
| 5,057,320 A | 10/1991 | Evans et al. |
| 5,085,996 A | 2/1992 | Evans |
| 5,087,623 A | 2/1992 | Boynton et al. |
| 5,087,624 A | 2/1992 | Boynton et al. |
| 5,093,200 A | 3/1992 | Watanabe et al. |
| 5,106,836 A | 4/1992 | Clemens et al. |
| 5,114,963 A | 5/1992 | Holaday et al. |
| RE33,988 E | 7/1992 | Evans |
| 5,164,384 A | 11/1992 | Paul |
| 5,175,156 A | 12/1992 | Boynton et al. |
| 5,194,615 A | 3/1993 | Jensen |
| 5,320,853 A | 6/1994 | Noda et al. |
| 5,336,672 A | 8/1994 | Southern, Jr. et al. |
| 5,340,834 A | 8/1994 | Stitt |
| 5,474,978 A | 12/1995 | Bakaysa et al. |
| 5,496,827 A | 3/1996 | Patrick |
| 5,534,488 A | 7/1996 | Hoffmann |
| 5,582,839 A | 12/1996 | McCarty |

(Continued)

FOREIGN PATENT DOCUMENTS

| | | |
|---|---|---|
| CN | 1665566 A | 9/2005 |
| CN | 1823608 A | 8/2006 |

(Continued)

OTHER PUBLICATIONS

Anderson et al., "Lack of Toxicity of Chromium Chloride and Picolinate in Rats," J. Am. Coll. Nutr., 1997; 16(3): pp. 273-279.
Anderson, "Chromium Metabolism and Its Role in Disease Processes in Man," Clin. Psychol. Biochem., 1986; 4: pp. 31-41.
Boyle et al., "Chromium depletion in the pathogenesis of diabetes and atherosclerosis," Southern Med. J., 1977; 70: pp. 1449-1453.
Davis et al., "Effects of Over-the-Counter Drugs on Chromium Retention and Urinary Excretion in Rats", J. Nutrition Res., 1995; 15: pp. 202-210.
International Search Report and Written Opinion issued in PCT/US2017/016946, dated June 7, 2017.

(Continued)

*Primary Examiner* — Terry A McKelvey
*Assistant Examiner* — Catheryne Chen
(74) *Attorney, Agent, or Firm* — Foley Hoag LLP; Lucas P. Watkins

(57) ABSTRACT

Administration of certain chromium complexes in combination with a starch provide unexpected benefits regarding increasing amino acid absorption, protein synthesis, exercise tolerance, lean muscle mass, skeletal muscle hypertrophy, muscle power, muscle endurance, muscle strength, FSR, and decreasing delayed onset muscle soreness, muscle protein breakdown, and fat mass.

14 Claims, 21 Drawing Sheets

(56) References Cited

U.S. PATENT DOCUMENTS

| | | | |
|---|---|---|---|
| 5,597,585 A | 1/1997 | Williams et al. |
| 5,614,553 A | 3/1997 | Ashmead et al. |
| 5,631,288 A | 5/1997 | De Simone |
| 5,635,535 A | 6/1997 | Wagstaff |
| 5,643,957 A | 7/1997 | Leone-Bay et al. |
| 5,650,386 A | 7/1997 | Leone-Bay et al. |
| 5,707,970 A | 1/1998 | McCarty et al. |
| 5,721,114 A | 2/1998 | Abrahamsen et al. |
| 5,731,303 A | 3/1998 | Hsieh |
| 5,766,633 A | 6/1998 | Milstein et al. |
| 5,773,647 A | 6/1998 | Leone-Bay et al. |
| 5,776,498 A | 7/1998 | McCarty |
| 5,776,504 A | 7/1998 | McCarty |
| 5,776,888 A | 7/1998 | Leone-Bay et al. |
| 5,789,401 A | 8/1998 | McCarty |
| 5,804,688 A | 9/1998 | Leone-Bay et al. |
| 5,858,968 A | 1/1999 | Weiner et al. |
| 5,863,944 A | 1/1999 | Leone-Bay et al. |
| 5,866,536 A | 2/1999 | Leone-Bay et al. |
| 5,876,710 A | 3/1999 | Leone-Bay et al. |
| 5,876,757 A | 3/1999 | McCarty |
| 5,879,681 A | 3/1999 | Leone-Bay et al. |
| 5,914,326 A | 6/1999 | McCarty et al. |
| 5,929,066 A | 7/1999 | McCarty |
| 5,939,381 A | 8/1999 | Leone-Bay et al. |
| 5,948,772 A | 9/1999 | de la Harpe et al. |
| 5,955,503 A | 9/1999 | Leone-Bay et al. |
| 5,965,121 A | 10/1999 | Leone-Bay et al. |
| 5,989,539 A | 11/1999 | Leone-Bay et al. |
| 5,990,166 A | 11/1999 | Leone-Bay et al. |
| 6,001,347 A | 12/1999 | Leone-Bay et al. |
| 6,004,925 A | 12/1999 | Dasseux et al. |
| 6,014,846 A | 1/2000 | Sono et al. |
| 6,037,323 A | 3/2000 | Dasseux et al. |
| 6,048,846 A | 4/2000 | Cochran |
| 6,051,561 A | 4/2000 | Leone-Bay et al. |
| 6,060,513 A | 5/2000 | Leone-Bay et al. |
| 6,071,510 A | 6/2000 | Leone-Bay et al. |
| 6,090,958 A | 7/2000 | Leone-Bay et al. |
| 6,099,869 A | 8/2000 | McCarty |
| 6,100,298 A | 8/2000 | Leone-Bay et al. |
| 6,136,317 A | 10/2000 | de la Harpe et al. |
| 6,140,304 A | 10/2000 | Sears |
| 6,156,735 A | 12/2000 | McCarty et al. |
| 6,203,823 B1 | 3/2001 | McCarty |
| 6,251,889 B1 | 6/2001 | de la Harpe |
| 6,329,361 B1 | 12/2001 | McCarty |
| 6,344,444 B1 | 2/2002 | McCarty et al. |
| 6,358,504 B1 | 3/2002 | Leone-Bay et al. |
| 6,376,549 B1 | 4/2002 | Fine et al. |
| 6,524,616 B1 | 2/2003 | Notelivitz et al. |
| 6,576,233 B2 | 6/2003 | Hsia et al. |
| 6,579,866 B2 | 6/2003 | McCleary |
| 6,689,383 B1 | 2/2004 | Anderson et al. |
| 6,693,129 B2 | 2/2004 | Rath et al. |
| 6,809,115 B2 | 10/2004 | Katz et al. |
| 6,955,873 B1 | 10/2005 | Blum |
| 7,112,561 B2 | 9/2006 | Gyurik et al. |
| RE39,480 E | 1/2007 | McCarty |
| 7,247,328 B2 | 7/2007 | Abdel-Monem et al. |
| 7,291,591 B2 | 11/2007 | Fishman |
| 7,300,927 B2 | 11/2007 | Esmond et al. |
| 7,429,564 B2 | 9/2008 | Arbit et al. |
| 8,062,677 B2 | 11/2011 | Komorowski |
| 8,586,061 B2 | 11/2013 | Komorowski |
| 8,771,752 B2 | 7/2014 | Mao et al. |
| 8,933,022 B2 | 1/2015 | Komorowski |
| 9,005,637 B2 | 4/2015 | Komorowski |
| 9,028,879 B2 | 5/2015 | Komorowski |
| 9,119,835 B2 | 9/2015 | Komorowski |
| 9,421,170 B2 | 8/2016 | Komorowski |
| 9,597,404 B2 | 3/2017 | Komorowski |
| 9,675,702 B2 | 6/2017 | Komorowski |
| 10,245,325 B2 | 4/2019 | Komorowski |
| 2002/0009824 A1 | 1/2002 | Maeda |
| 2002/0081315 A1* | 6/2002 | Katz .................. A61K 36/45 424/195.16 |
| 2002/0086065 A1 | 7/2002 | Katz |
| 2002/0098247 A1 | 7/2002 | Komorowski et al. |
| 2002/0197331 A1 | 12/2002 | Komorowski et al. |
| 2003/0059824 A1 | 3/2003 | Henderson |
| 2003/0091654 A1 | 5/2003 | Katz et al. |
| 2003/0211172 A1 | 11/2003 | Jones et al. |
| 2004/0005368 A1 | 1/2004 | Mann et al. |
| 2004/0043065 A1 | 3/2004 | Stankov |
| 2004/0058873 A1 | 3/2004 | Esmond et al. |
| 2004/0115265 A1 | 6/2004 | Benkerrour et al. |
| 2004/0185119 A1 | 9/2004 | Theuer |
| 2005/0058704 A1 | 3/2005 | Schneider et al. |
| 2005/0069593 A1 | 3/2005 | Zwiefel |
| 2005/0214384 A1 | 9/2005 | Juturu et al. |
| 2005/0214385 A1 | 9/2005 | Komorowski et al. |
| 2005/0233946 A1 | 10/2005 | Fine et al. |
| 2006/0008857 A1 | 1/2006 | Oda et al. |
| 2006/0024383 A1 | 2/2006 | Berlin |
| 2006/0062859 A1 | 3/2006 | Blum et al. |
| 2006/0088574 A1 | 4/2006 | Manning et al. |
| 2006/0234913 A1 | 10/2006 | Arbit et al. |
| 2007/0092584 A1 | 4/2007 | Fine et al. |
| 2007/0179197 A1 | 8/2007 | Henderson |
| 2007/0231260 A1 | 10/2007 | Zerangue et al. |
| 2008/0206415 A1* | 8/2008 | Sherwood .................. A23J 3/08 426/326 |
| 2009/0099215 A1* | 4/2009 | Cornelius ................ A23L 33/10 514/263.31 |
| 2009/0155384 A1 | 6/2009 | Komorowski |
| 2010/0009015 A1* | 1/2010 | Juturu .................. A61K 31/415 424/655 |
| 2010/0178362 A1 | 7/2010 | Komorowski et al. |
| 2010/0227007 A1* | 9/2010 | Romero .................. A61P 43/00 424/725 |
| 2010/0262434 A1 | 10/2010 | Shaya |
| 2011/0293759 A1 | 12/2011 | Westerlund |
| 2012/0028891 A1 | 2/2012 | Paetau-Robinson et al. |
| 2012/0100228 A1 | 4/2012 | Komorowski |
| 2012/0100229 A1 | 4/2012 | Rivkees |
| 2012/0128794 A1 | 5/2012 | Komorowski |
| 2012/0225134 A1 | 9/2012 | Komorowski |
| 2015/0094258 A1 | 4/2015 | Komorowski |
| 2015/0174074 A1 | 6/2015 | Komorowski |
| 2015/0224140 A1 | 8/2015 | Komorowski |
| 2015/0272991 A1 | 10/2015 | Juturu et al. |
| 2015/0320796 A1 | 11/2015 | Komorowski |
| 2015/0320874 A1 | 11/2015 | Komorowski |
| 2015/0368369 A1 | 12/2015 | Wu-Wong |
| 2016/0220581 A1 | 8/2016 | Komorowski et al. |
| 2016/0234784 A1 | 8/2016 | Hamada |
| 2016/0375035 A1 | 12/2016 | Komorowski |
| 2017/0304360 A1 | 10/2017 | Komorowski |
| 2019/0216821 A1 | 7/2019 | Komorowski |
| 2019/0314510 A1 | 10/2019 | Komorowski |
| 2022/0023337 A1 | 1/2022 | Juturu et al. |

FOREIGN PATENT DOCUMENTS

| | | |
|---|---|---|
| CN | 103702672 A | 4/2014 |
| EP | 0016496 A1 | 10/1980 |
| EP | 0598309 A2 | 5/1994 |
| EP | 0881649 A1 | 12/1998 |
| EP | 1731142 A1 | 12/2006 |
| EP | 2134351 A1 | 12/2009 |
| GB | 1443662 A | 7/1976 |
| IN | 208600 | 8/2007 |
| WO | WO-89/10357 A1 | 11/1989 |
| WO | WO-91/11117 A2 | 8/1991 |
| WO | WO-95/28838 A1 | 11/1995 |
| WO | WO-96/35421 A1 | 11/1996 |
| WO | WO-98/25589 A1 | 6/1998 |
| WO | WO-98/44793 | 10/1998 |
| WO | WO-99/07387 A1 | 2/1999 |
| WO | WO-96/25939 A1 | 8/1999 |
| WO | WO-00/06534 A1 | 2/2000 |
| WO | WO-00/07979 A2 | 2/2000 |

(56) References Cited

FOREIGN PATENT DOCUMENTS

| | | |
|---|---|---|
| WO | WO-00/12095 A1 | 3/2000 |
| WO | WO-2000/015211 A2 | 3/2000 |
| WO | WO-00/47188 A1 | 8/2000 |
| WO | WO-00/50386 A1 | 8/2000 |
| WO | WO-00/59863 A1 | 10/2000 |
| WO | WO-01/19542 A1 | 3/2001 |
| WO | WO-2001021073 A1 | 3/2001 |
| WO | WO-01/25679 A1 | 4/2001 |
| WO | WO-01/25704 A1 | 4/2001 |
| WO | WO-01/27123 A1 | 4/2001 |
| WO | WO-01/32130 A2 | 5/2001 |
| WO | WO-01/32596 A1 | 5/2001 |
| WO | WO-01/34114 A1 | 5/2001 |
| WO | WO-01/41985 A1 | 6/2001 |
| WO | WO-01/44199 A1 | 6/2001 |
| WO | WO-01/51454 A1 | 7/2001 |
| WO | WO-2001/58284 A1 | 8/2001 |
| WO | WO-02/02509 A1 | 1/2002 |
| WO | WO-02/04024 A1 | 1/2002 |
| WO | WO-02/11564 A2 | 2/2002 |
| WO | WO-02/19969 A2 | 3/2002 |
| WO | WO-02/20466 A1 | 3/2002 |
| WO | WO-2002/024180 A2 | 3/2002 |
| WO | WO-02/36127 A2 | 5/2002 |
| WO | WO-02/36202 A2 | 5/2002 |
| WO | WO-02/067953 A2 | 9/2002 |
| WO | WO-2002/069937 A1 | 9/2002 |
| WO | WO-2002/070438 A2 | 9/2002 |
| WO | WO-2003/028631 A2 | 4/2003 |
| WO | WO-2003/043569 A2 | 5/2003 |
| WO | WO-2003/090671 A2 | 11/2003 |
| WO | WO-2004/107881 A1 | 12/2004 |
| WO | WO-2006/060753 A2 | 6/2006 |
| WO | WO-2007/016256 A2 | 2/2007 |
| WO | WO-2008/094939 A1 | 8/2008 |
| WO | WO-2008/112706 A1 | 9/2008 |
| WO | WO-2009/002867 A2 | 12/2008 |
| WO | WO-2009/009393 A2 | 1/2009 |
| WO | WO-2011/002939 A1 | 1/2011 |
| WO | WO-2012/119007 A1 | 9/2012 |
| WO | WO-2017/139337 A1 | 8/2017 |

OTHER PUBLICATIONS

Kamath et al., "Absorption, Retention and Urinary Excretion of Chromium-51 in Rats Pretreated with Indomethacin and Dosed with Dimethylprostaglandin E2, Misoprostol or Prostacyclin1,2,3," J. Nutrition, (1997); 127: pp. 478-482.

Komorowski, Nutrition21 Press Release, [online], Dec. 2015, [retrieved on Mar. 31, 2017]. Retrieved from the Internet: <URL: http://nutrition21.com/wp-content/uploads/2016/01/ISNEC_V_Press-Release_DRA625VPRISENC121815aa.pdf>.

Moore et al., "Ingested protein dose response of muscle and albumin protein synthesis after resistance exercise in young men," Am. J. Clin. Nutr., 2009; 89(1): pp. 161-168.

Nair et al., "A simple practice guide for dose conversion between animals and human," J Basic Clin Pharm., 2016; 7(2): pp. 27-31.

National Academy of Sciences, Recommended Dietary Allowances, Chromium, pp. 159-161 (1980).

Pi-Sunyer et al., "Chromium" Chapter 40, Present Knowledge in Nutrition, 5th Edition, Published by The Nutrition Foundation, Inc., Washington, D.C., 1984: pp. 571-586.

Recommended Daily Allowances, Ninth Revised Edition, The National Academy of Sciences, (1980): p. 160.

Schwarz and Mertz, "Chromium (III) and the Glucose Tolerance Factor," Letters to the Editor, 1959: pp. 292-295, 1959.

Sigma-Aldrich, nicotinic acid; catalog No. N4126, [online], [retrieved on Apr. 16, 2018]. Retrieved from the Internet: <URL: https://www.sigmaaldrich.com/catalog/product/sial/n4126?lang=en&region=US>.

Sigma-Aldrich, picolinic acid; catalog No. P5503, [online], [retrieved on Apr. 16, 2018]. Retrieved from the Internet: <URL: https://www.sigmaaldrich.com/catalog/product/sigma/p5503?lang=en&region=US>.

Ziegenfuss, "Novel Chromium/Amylopectin Complex Increases Muscle Protein Synthesis When Combined with a Suboptimal Dose of Whey Protein," The International Sport & Exercise Nutrition Conference (Dec. 2015). [online], Retrieved from the Internet: <URL: https://nutrition21.com/wp-content/uploads/2016/01/UK-N21-Poster-2015-V6.pdf>.

Symons et al. "A Moderate Serving of High-Quality Protein Maximally Stimulates Skeletal Muscle Protein Synthesis in Young and Elderly Subjects," J Am Diet Assoc., 2009; 109(9): pp. 1582-1586.

Zhang, "A Good Diet Can Help You Build Muscles," published on Dec. 31, 2007. English translation included.

Tigerfitness.com, [online], retrieved from the Internet: < URL: <https://www.tigerfitness.com/blogs/supplements/velositol-the-protein-potentiating-powerhouse>, 2012.

Agency for Toxic Substances and Disease Registry, Sep. 2008, Public Health Statement: Perchlorates, 10 pp.

Alberti et al., "Definition, Diagnosis and Classification of Diabetes Mellitus and it's Complications Part 1: Diagnosis and Classification of Diabetes Mellitus Provisional Report of a WHO Consultation," Diabet Med., 1998; 15: pp. 539-553. cited by applicant.

Albrink et al., "Effect of high-and low-fiber diets on plasma lipids and insulin," The Am. J. Clin. Nutr., 1979; 32: pp. 1486-1491.

American Heart Association Dec. 6, 2000, About Cholesterol: what are healthy levels of cholesterol? [online], [retrieved on Mar. 1, 2011]. Retrieved from the Internet: <URL:https://web.archive.org/web/20001206061100/americanheart.org/cholesterol/-about_level.html>.

Anderson "Nutritional factors influencing the glucose/insulin system: chromium," J Am Coll Nutr, 1997; 16: pp. 404-410.

Anderson et al., "Effects of supplemental chromium on patients with symptoms of reactive hypoglycemia," Metabolism, 1987; 36(4): pp. 351-355.

Anderson, et al., "Stability and Absorption of Chromium and Absorption of Chromium Histidinate Complexes by Humans", Biological Trace Element Research, vol. 101; 211-218 (2004).

Anonymous. New chromium formulation for easy absorption. Nutra [online]; 2001; downloaded from <URL https://www.nutraingredients.com/Article/2001/12/05/New-chromium-formulation-for-easy-absorption#> retrieved on May 6, 2016.

Aragno et al., "Dehydroepiandrosterone modulates nuclear factor-kB activation in hippocampus of diabetic rats," Endocrinology, 2002; 143(9): pp. 3250-3258.

Badimon et al., "Role of high density lipoproteins in the regression of atherosclerosis", Supplement III Circulation, 1992; 86(6): pp. 86-94.

Bailey et al., "Exposure of Pregnant Mice to Chromium Picolinate Results in Skeletal Defects to Their Offspring," Birth Defects Research (Part B), 2006; 77: pp. 244-249.

Beales et al., "Caution is required with Interferon a as a potential treatment for Type I diabetes," Diabetes; 42: p. 385 (1999).

Belusko, Jun. 1977, Evidence for chromium-insulin interaction, Dissertation, Loyola University Chicago, 258 pp.

Berge et al., "Pharmaceutical Salts," J. Pharm. Sci., 1977, 66(1): pp. 1-19.

Bilsky et al., "Enkephalin Glycopeptide Analogues Produce Analgesia with Reduced Dependence Liability," J. Med. Chem.,2000; 43: pp. 2586-2590.

BioVendor Research and Diagnostic Products, Porcine Insulin ELISA Kit (product information), 16 pp., accessed Jan. 7, 2016.

Bourasset et al., "Evidence for an active transport of morphine-6-beta-D-glucuronide but not P-glycoprotein-mediated at the blood-brain barrier," J. Neurochem., 2003; 86: pp. 1564-1567.

Brand-Miller, "Importance of glycemic index in diabetes," Am. J. Clin. Nutr., 1994; 59(suppl): pp. 747S-752S.

Bridges, "Iron Deficiency", Encyclopedia of Life Sciences, published by Wiley Online Library Apr. 19, 2001, [retrieved on Nov. 10, 2011]. Retrieved from the Internet: < URL: https://onlinelibrary.wiley.com/doi/abs/10.1038/npg.els.0002277>.

(56) References Cited

OTHER PUBLICATIONS

Brun et al. "Synapse Loss and Gliosis in the Molecular Layer of the Cerebral Cortex in Alzheimer's Disease and in Frontal Lobe Degeneration," Neurodegeneration, 1995; 4: pp. 171-177.
Byrnes et al., "Amylopectin starch promotes the development of insulin resistance in rats," J. Nutr., 1995; 125: pp. 1430-1437.
Campbell et al., "Interaction of insulin and chromium (III) on mitochondrial swelling," Am. J. Physiol, 1962; 204(6): pp. 1028-1030.
Castro et al., "Cardiometabolic Syndrome: Pathophysiology and Treatment", Curr Hypertens Rep., 2003; 5(5): pp. 393-401.
Cefalu et al., "Role of chromium in human health and in diabetes," Diabetes Care, 2004; 27(11): pp. 2741-2751, [online]. Retrieved from the Internet: < URL: http://care.diabetesjournals.org/content/27/11/2741.full-text.pdf>.
Cefalu et al., "The Effect of Chromium Supplementation on Carbohydrate Metabolism and Body Fat Distribution" Diabetes, 1997; 46(1): p. 55A. (Abstract).
Cefalu, "Effect of Chromium Picolinate on Insulin Sensitivity in Vivo," J. Trace Elem Exp Med., 1999; 12: pp. 71-83.
Chemspider, Chromium Picolinate, [online], [retrieved on Jan. 7, 2016]. Retrieved from the Internet: < URL: http://www.chemspider.com/Chemical-Structure.133913.html>.
Chen et al., "Risk of cardiovascular disease and all-cause mortality among diabetic patients prescribed rosignlitazone or pioglitazone: a meta-analysis of retrospective cohort studies," Chinese Medical Journal, 2012; 125(23): pp. 4301-4306. cited byapplicant.
Christman et al., "Redox regulation of nuclear factor Kappa B: therapeutic potential for attenuating inflammatory responses," Brain Pathology, 2000; 10(1): pp. 153-162.
Chrom bei Diabetes mellitus, (Oct. 31, 2010), Retrieved from the Internet: web.archive.org/web/28181831894712/www.diabetiker-experte.de/Chrom-bei-Diabetes- mellitus.html, 3 pp.
Chung, "Effects of biotin-rich functional food (whalgichan) on hair growth and biological stimulation in rat and human," J. Food Sci. Nutr., 2000; 5(1): pp. 42-47.
Coggeshall et al., "Biotin Status and Plasma Glucose in Diabetics," Annals N.Y. Acad. Sci., 1985; 447: pp. 389-392.
Cornford et al., "High Expression of the Glut1 Transporter in Human Brain Hemangioblastoma Endothelium," J. Neuropathol. Exp. Neurol., 1995; 54(6): pp. 842-851.
Cornford, et al., "Dynamic [.sup. 18F] Fluorodeoxyglucose Positron Emission Tomography and Hypometabolic Zones in Seizures: Reduced Capillary Influx," Ann. Neurol., 1998; 43(6): pp. 801-808.
Dansky et al., "High-Density Lipoprotein and Plaque Regression: The Good Cholesterol Gets Even Better," Circulation; 1999; 100: pp. 1762-1763.
Davidson et al., "Effectiveness of Chromium in Atypical Depression: A Placebo-Controlled Trial," Biological Psychiatry, 2003; 53: pp. 261-264.
Defronzo et al., "Glucose Clamp Technique: A method for quantifying insulin secretion and resistance," Am. J. Physiol., 1979; pp. E214-E223.
Dickinson, 2012 https ://www.crnusa.org/sites/default/fi les/pdfs-benefi ts/CR N-Benefitsof Nutritional Supplements-2012. pdf.
Diem et al., "Scientific Tables," Documenta Geigy, Seventh Edition, 1975; pp. 457-497.
Dietary Reference Intakes (DRIs): Estimated Average Requirements, Food and Nutrition Board, Institute of Medicine, 2001, National Academies, 8 pp.
Diplock, "Antioxidant Nutrients and Disease Prevention: An Overview" Am. J. Clin. Nutr., 1991; 53: p. 189S-193S.
Dokusova et al., 1972, The effect of biotin on the level of cholesterol in the blood of patients with atherosclerosis and essential hyperlipidemia, Kardiologiia, 12(12):113.
Domenico, "Only One Chromium Supplement Helps People with Diabetes," an electronic article from www.naturalnews.com published Dec. 5, 2008, online, [retrieved on Apr. 6, 2017]. Retrieved from the Internet: <URL:http://www.naturalnews.com/z025006_chromium_supplement_sugar.htmll>.

Dorflinger, "Metabolic Effects of Implantable Steroid Contraceptives for Women", Contraception, 2002; 65: pp. 47-62.
Dousset et al., "Trace Elements, Free Radicals, and HIV Progression", Nutrition and Aids, 2nd Ed., CRC Press, Chapter 4, p. 23-39 (2001).
Drake et al., "Chromium Infusion in hospitalized patients with severe insulin resistance: a retrospective analysis," Endocr Pract., 2012; 18(3): pp. 394-398.
Drugbank, Succinic Acid, Jan. 13, 2005, [online]. Retrieved from the Internet: < URL: http://www.drugbank.ca/drugs/DB00139>.
EP Extended Search Report, dated May 7, 2005, European Application No. 08731918.2 (PCT/US2008/056545).
European Search Report and Opinion dated Apr. 14, 2016 for EP Patent Application No. 16160735.3.
Evans et al., "Chromium Picolinate Increases Membrane Fluidity and Rate of Insulin Internalization" Journal of Inorganic Biochemistry, 1992; 46: pp. 243-250.
Feng et al., "Chromium picolinate reduces insulin requirement in people with type 2 diabetes mellitus," Diabetes. (2002 Annual Conference), 2002; 51(2): p. A469-1929-PO. (Abstract).
Fielding et al., Molecular Physiology of Reverse Cholesterol Transport, J Lipid Res, 1995; 36: pp. 211-228.
Folstein et al., ""Mini-Mental State" A Practical Method for Grading the Cognitive State of Patients for the Clinician," J Psychiatr Res., 1975; 12: pp. 189-198.
Fontvieille et al., "The use of low glycaemic index foods improves metabolic control of diabetic patients over five weeks," Diabetic Medicine, 1992; 9: pp. 444-450.
Gamberino et al. "Glucose Transporter Isoform Expression in Huntington's Disease Brain," J. Neurochem., 1994; 63: pp. 1392-1397.
Garg et al., "Comparison of effects of high and low carbohydrate diets on plasma lipoproteins and insulin sensitivity in patients with mild NIDDM," Diabetes, 1992; 41: pp. 1278-1285.
Gavin Iii, M.D et al., "Report of the Expert Committee on the Diagnosis and Classification of Diabetes Mellitus", Diabetes Care; 20(7): pp. 1183-1197. (1997).
Godsland et al., "Insulin resistance, secretion and metabolism in users of oral contraceptives," Journal of Clinical Endocrinology and Metabolism, 1992; 74(1): pp. 64-79.
Golik et al., "Effects of captopril and enalapril on zinc metabolism in hypertensive patients," Journal of the American College of Nutrition, 1998; 17(1): pp. 75-78.
Goodman and Gilman, 1992, The Pharmacological Basis of Therapeutics, Pergamon Oress, Eighth Edition, pp. 5-6.
Govindaraju et al., "Chromium(III)-Insulin Derivatives and Their Implication in Glucose Metabolism", Journal of Inorganic Biochemistry, 1989; 35: pp. 137-147.
Govindaraju et al., "Chymotrypsin-Catalyzed Hydrolysis of Chromium(III) Derivatives of Insulin: Evidence for Stabilization of the Protein Through Interactions with Metal lons", Journal of Inorganic Biochemistry, 1989; 35: pp. 127-135. cited by applicant.
Gress et al., "Hypertension and Antihypertensive Therapy as Risk Factors for Type 2 Diabetes Mellitus", N. Eng. J. Med., 2000; 342: pp. 905-912.
Gustaw-Rothenberg et al., "Biomarkers in Alzheimer's disease: past present and future," Biomark Med., 2010; 4(1): pp. 15-26.
Hannonen et al., "Neurocognitive functioning in children with type-1 diabetes with and without episodes of severe hypoglycaemia," Developmental Medicine & Child Neurology 2003; 45(4): pp. 262-268.
Harding et al., "Outcome-based comparison of Ritalin.RTM. versus food-supplement treated children with AD/HD," Alternative Medicine Review, 2003; 8(3): pp. 319-330.
Harrington et al., "Rosiglitazone Does Not Improve Cognition or Global Function when Used as Adjunctive Therapy to AChE Inhibitors in Mild-to-Moderate Alzheimer's Disease: Two Phase 3 Studies," Current Alzheimer Research, 2011; 8: pp. 592-606.
Hayden et al., "Molecular Genetics of Human Lipoprotein Lipase Deficiency", Mol. Cell Biochem., 1992; 113: pp. 171-176.
Hebert et al., "Alzheimer Disease in the US Population," Arch. Neurol., 2003; 60: pp. 1119-1122.

(56) References Cited

OTHER PUBLICATIONS

Higgins et al., "Development of insulin resistance in the rat is dependent on the rate of glucose absorption from the diet," J. Nutr., 1996; 126: pp. 596-602.
Hoggard, "L-Histidine Complexes of Chromium(III)," Inorganic Chemistry, 1981; 20(2): pp. 415-421.
Hou et al., "Influence of blood glucose on the expression of glucose transporter proteins 1 and 3 in the brain of diabetic rats, "Chin Med J (Engl)., 2007; 120(19): pp. 1704-1709.
Hughes et al., "A New Clinical Scale for the Staging of Dementia," Brit. J. Psychiat., 1982; 140: pp. 566-572.
International Preliminary Report on Patentability dated Aug. 13, 2009 for PCT Application No. PCT/US2008/052352.
International Preliminary Report on Patentability dated Jan. 12, 2010 in PCT/US2008/069079.
International Preliminary Report on Patentability dated Nov. 17, 2011 for PCT Application No. PCT/US10/40679.
International Preliminary Report on Patentability, dated Sep. 15, 2009, PCT/US2008/056545.
International Search Report and Written Opinion dated Aug. 16, 2010 for PCT Application No. PCT/US10/40679.
International Search Report and Written Opinion dated Jan. 8, 2009 in PCT/US2008/069079.
International Search Report and Written Opinion dated Jun. 3, 2008 for PCT Application No. B PCT/US2008/052352.
International Search Report and Written Opinion for International Application No. 8 PCT/US16/38513, mailed Sep. 19, 2016.
International Search Report and Written Opinion issued in PCT/US2017/016946, mailed Jun. 7, 2017.
International Search Report and Written Opinion, dated Jul. 31, 2008, PCT/US2008/056545.
Jula et al., "Effects of Diet and Simvastatin on Serum Lipids, Insulin, and Antioxidants in Hypercholesterolemic Men," JAMA, 2002; 287: pp. 598-605.
Julius et al., "Antihypertensive Treatment of Patients with Diabetes and Hypertension", Am. J. Hypertens., 2001; 14(11): p. 310S-316S.
Juturu et al., "Absorption and excretion of chromium from orally administered chromium chloride, chromium acetate and chromium oxide in rats," Trace Elements and Electrolytes, 2003; 20(1): pp. 23-28.
Juturu et al., Faseb J. (2003), vol. 17, No. 5, Pt. 2, A1098, Abstract. STN online, file DRUGU, Acc. No. 2003-34331.
Juturu, "Cardiometabolic Syndrome -- New Therapeutic Challenges, " Medical Nutrition Matters, 2006; 26(2): pp. 1, 3-10.
Kaats et al., "A Randomized, Double-Masked, Placebo-Controlled Study of the Effects of Chromium Picolinate Supplementation on Body Composition: A Replication and Extension of a Previous Study," Curr. Ther. Res., 1998; 59(6): pp. 379-388. cited byapplicant.
Kalaria et al., "Reduced Glucose Transporter at the Blood-Brain Barrier and in Cerebral Cortex in Alzheimer Disease," J. Neurochem., 1989; 53(4): pp. 1083-1088.
Kannel et al., "Declining cardiovascular mortality," Circulation, 1984; 70(3): pp. 331-336.
Kashyap, "Cholesterol and atherosclerosis: a contemporary perspective," Ann. Acad. Med. Singapore, 1997; 26(4):517-523 (abstract).
Katsumata et al., "Suboptimal energy balance selectively up-regulates muscle GLUT gene expression but reduces insulinindependent glucose uptake during postnatal development," Faseb J., 1999; (13): pp. 1405-1413.
Katz et al., "Quantitative Insulin Sensitivity Check Index: A Simple, Accurate Method for Assessing Insulin Sensitivity in Humans," J Clin Endocrinol Metab., 2000; 85(7): pp. 2402-2410.
Khan et al., "Synthesis and Characterization of Cr(III), Fe(III) and Ni(II) Complexes of a-Amino, Imidazolepropanoic Acid," Asian Journal of Chemistry, 2011; 23(5): pp. 1969-1972.
Kim et al., "Molecular targets of selenium in cancer prevention," Nutrition and Cancer, 2001; 40(1): pp. 50-54.
Koivisto et al., "Lispro Mix25 insulin as premeal therapy in type 2 diabetic patients," Diabetes Care, 1999; 22(3): pp. 459-462.

Kolata, "Drug Trials Test Bold Plan to Slow Alzheimer's," The New York Times, 2010: 6 pp., online, [retrieved on May 13, 2014]. Retrieved from the Internet: < URL: https://www.nytimes.com/2010/07/17/health/research/17drug.html?pagewanted -= all>.
Komorowski et al., "Chromium histidinate increases brain GLUT-1 and GLUT-3 levels impaired by insulin resistance," Journal of Cerebral Blood Flow and Metabolism, 2009; 29: pp. S392- S393.
Komorowski et al., "Chromium histidinate reduces brain damage caused by insulin-induced hypoglycemia," The FASEB Journal, 2011; 25: 766.13 (Abstract).
Kozauer et al., "Regulatory innovation and drug development for early-stage Alzheimer's disease," The New England Journal of Medicine, 2013: 3 pp.
Kriss et al., "Enkephalin-based drug design: conformational analysis of O-linked glycopeptides by NMR and molecular modeling," Tetrahedron-Asymmetr., 2000; 11: pp. 9-25.
Lastra et al., "Cardiometabolic Syndrome and Chronic Kidney Disease", Curr Diab Rep., 2006; 6(3): pp. 207-212.
Lee et al., "Beneficial effect of chromium supplementation on serum triglyceride levels in NIDDM," Diabetes Care, 1994; 17(12): pp. 1449-1452.
Lemme et al. "Action of chromium (III) on growth and carcass composition of swine for rations with differing glycemic index," (Wirkung von Chrom (III) auf Wachstuin und Schlachtkoperzusammensetzung von Schweinen bei Rationen mit unterschiedlichemglycamischen index) Mengen-und Spurenelemente, Arbeistagung, 17th, Jena (1997), pp. 200-207. (with translation).
Lerer-Metzger et al., "Effects of long-term low-glycaemic index starchy food on plasma glucose and lipid concentrations and adipose tissue cellularity in normal and diabetic rats," British Journal of Nutrition, 1996; 75: pp. 723-732. cited byapplicant.
Lindemann et al., "Effect of chromium source on tissue concentration of chromium in pigs" J Anim Sci, 2008; 86: pp. 2971-2978.
Liu et al., "A prospective study of dietary glycemic load and risk of myocardial infarction in women," Atherosclerosis-Diet and Metabolic Disease II, The FASEB Journal, An Annual Meeting of Professional Research Scientists, 1998; (Abstract).
Liu et al., "Decreased glucose transporters correlate to abnormal hyperphosphorylation of tau in Alzheimer disease, " FEBS Letters 582, 2008: pp. 359-364.
Maebashi et al., "Therapeutic evaluation of the effect of biotin on hyperglycemia in patients with non-insulin dependent diabetes mellitus." J. Clin. Biochem. Nutr., 1993; 14: pp. 211-218.
Mangialasche et al., "Alzheimer's disease: clinical trials and drug development," Lancet Neural, 2010; 9: pp. 702-716.
Markesbery et al., "Oxidative Alterations in Alzheimer's Disease," Brain Pathol, 1999; 9: pp. 133-146.
Martin et al., "Chromium picolinate supplementation attenuates body weight gain and increases insulin senstivitiy in subjects with type 2 diabetes," Diabetes Care, 2006; 29(8): pp. 1826-1832.
Matthews et al., "Homeostasis model assessment: insulin resistance and beta-cell function from fasting plasma glucose and insulin concentrations in man," Diabetologia, 1985; 28: pp. 412-419.
Mazziotta, et al. "Reduced Cerebral Glucose Metabolism in Asymptomatic Subjects at Risk for Huntington's Disease," New England J. Med., 1987; 316(7): pp. 357-362.
Mccarty, "Dietary glycemic index may influence cancer risk by modulating IGF-1 activity: a hypothesis," Journal of Medicinal Food, 1998; 1(2): pp. 123-140.
Mccarty, "High-dose biotin, an inducer of glucokinase expression, may synergize with chromium picolinate to enable a definitive nutritional therapy for type II diabetes," Medical Hypotheses, 1999; 52(5): pp. 401-406.
Mccarty, "Homologous physiological effects of phenformin and Chronium picolinate," Medical Hypothesis, 1993; 41: pp. 316-324.
Mccarty, "The Case for Supplemental Chromium and a Survey of Clinical Studies With Chromium Picolinate," Journal of Applied Nutrition, 1991; 43(1): pp. 58-66.
Mccarty, "Toward Prevention of Alzheimers Disease -- Potential Nutraceutical Strategies for Suppressing the Production of Amyloid Beta Peptides," Medical Hypotheses, 2006; 67: pp. 682-697.

(56) References Cited

OTHER PUBLICATIONS

Melki et al., "Expression of the adipocyte fatty acid-binding protein in streptozotocin-diabetes: effects of insulin deficiency and supplementation," Journal of Lipd Research, 1993; 34: pp. 1527-1534.
Mensink et al., "Effects of monounsaturated fatty acids v complex carbohydrates on serum lipoproteins and apoproteins in healthy men and women," Metabolism, 1989; 38(2): pp. 172-178.
Mertz, Walter. "Chromium in Human Nutrition: A Review." American Institute of Nutrition. 626- 633 (1993).
Miranda, et al., "Effect of Chromium and Zinc on Insulin Signaling in Skeletal Muscle Cells," Biological Trace Element Research, 2004; 101: pp. 19-36.
Mock, Chapter 22: Biotin, in Present Knowledge in Nutrition, Zeigler et al., eds., seventh edition, 1996; pp. 220-235.
Monster et al., "Oral Contraceptive Use and Hormone Replacement Therapy are Associated with Microalbuminuria", Arch Intern Med., 2001; 161: pp. 2000-2005.
Morrison et al., "High fat diet increases hippocampal oxidative stress and cognitive impairment in aged mice: implications for decreased Nrf2 signaling," J. Neurochem., 2010; 114: pp. 1581-1589.
Mossop, "Trivalent chromium, in atherosclerosis and diabetes," Central African Journal of Medicine, 1991; 37(11): pp. 369-374.
National Cholesterol Education Program of the National Heart, Lung and Blood Institute, "High Blood Cholesterol -- What You Need to Know," [online], [published Jun. 2005], Retrieved from the Internet: < URL:https://catalog.nhlbi.nih.gov/sites/default/files/publicationfiles/05-329- 0.pdf>.
Nijm et al., "Inflammation and cortisol response in coronary artery disease," Ann. Med .; 41 : pp. 224-233. (2009).
Nutrition 21, "New Clinical Data Shows Chromium Picolinate Improves Cognitive Function," an electronic article from www.businesswire.com, public release Dec. 13, 2007, online, [retrieved on Apr. 6, 2017]. Retrieved from the Internet: <URL:http://www.businesswire.com/news/home/20071213005201/en/Clinical-Data-Sho- ws- Chromium-Picolinate-Improves-Cognitive>.
O'Bryant et al., "Staging Dementia Using Clinical Dementia Rating Scale Sum of Boxes Scores: A Texas Alzheimer's Research Consortium Study," Arch. Neurol., 2008; 65(8): pp. 1091-1095.
Ornish et al., "Can lifestyle change reverse coronary heart disease?" Lancet, 1990; 336: pp. 129-133.
Pawlak et al., "Glycaemic index of food and the rate of fat deposition in rats," Proceedings of the Nutrition Society of Australia, 1997; 21:143.
Petersen et al., "Mild Congnitive Impairment". Arch Neurol, 1999; 56: pp. 303-308.
Petersen, "Pharmacodynamic Effects of Oral Contraceptive Steroids on Biochemical Markers for Arterial Thrombosis", Danish Medical Bulletin, 2002; 49: pp. 43-60.
Pilz et.al. "Elevated plasma free fatty acids predict sudden cardiac death: a 6.85-year follow-up of 3315 patients after coronary anaioaraphy," Eur. Heart J., (28): DD. 2763-2769.(2007).
Preuss, et al., "Comparing metabolic effects of six different commercial trivalent chromium compounds" Journal of Inorganic Biochemistry, 102:1986-1990 (2008).
Ramkishan, "Pharmacological evaluation of new drug formulations of insulin with trace elements of proven antidiabetic activity," Doctoral Thesis, Gujarat University, Oct. 2005, pp. 156-218.
Rangasamy et al. "Genetic ablation of Nrf2 enhances susceptibility to cigarette smoke-induced emphysema in mice", (2004) J Clin Invest 114:1248.
Ravina et al. "Reversal of corticosteroid-induced diabetes mellitus with supplemental chromium." Diabetic Medicine, 1999; 16: pp. 164-167.
Ravina et al., "Clinical Use of the Trace Element Chromium (III) in the Treatment of Diabetes Mellitus," The Journal of Trace Elements in Experimental Medicine, 1995; 8: pp. 183-190.
Ravina, et al. "Control of steroid induced diabetes with supplemental chromium." The Journal of Trace Elements in Experimental Medicine. 12: 375-378 (1999).

Reagan, et al., "Regulation of GLUT-3 glucose transporter in the hippocampus of diabetic rats subjected to stress ." Am. J. Physiol. Endocrinol. Metab., 1999; 276: pp. E879-E886.
Reddi et al., "Biotin supplementation improves glucose and insulin tolerances in genetically diabetic kk mice," Life Sciences, 1988; 42: pp. 1323-1330.
Reed et al., "A New Rat Model of Type 2 Diabetes: The Fat-fed, Streptozotocin-treated Rat" Metabolism 49(11):1390-1394 (2000).
Robins et al., "High Density Lipoproteins, But Not Other Lipoproteins, Provide a Vehicle for Sterol Transport to Bile", J. Clin. Invest., 1997; 99: pp. 380-384.
Rovner, "Alzheimer's Scary Link to Diabetes", Chemical & Engineering News, vol. 87, Issue 20, pp. 42-46, May 18, 2009.
Royal Society of Chemistry ChemSpider Database ID 133913, Chromium Picolinate, retrieved from http://www.chemspider.com/ Jan. 10, 2017.
Rudzite et al., "Changes in membrane fluidity induced by tryptophan and its metabolites," Advances in Experimental Medicine and Biology, 1999; 467: pp. 353-367.
Salmeron et al., "Dietary fiber, glycemic load, and risk of NIDDM in men," Diabetes Care, 1997; 20(4): pp. 545-550.
Salmeron et al., "Dietary fiber, glycemic load, and risk of non-insulin dependent diabetes mellitus in women," JAMA, 1997; 277(6): pp. 472-477.
Sayre et al. "4-Hydroxynonenal-Derived Advanced Lipid Peroxidation End Products are Increased in Alzheimer's Disease," J Neurochem 1997; 68(5): pp. 2092-2097.
Schwartz, Present Knowledae in Nutrition, pp. 571-577 (1984).
Sekine et al., "Molecular physiology of renal organic anion transporters," Am. J Physiol Renal Physiol, 2006; 290: pp. F251-F261.
Shimabukuro et al., "Fatty acid-induced B cell apoptosis: A link between obesity and diabetes," Proc. Nat. Acad. Sci., 1998; (95): DD. 2498- 2502.
Simpson et al., "Decreased Concentrations of GLUT1 and GLUT3 Glucose Transporters in the Brains of Patients with Alzheimer's Disease," Ann. Neurol., 1994; 35: pp. 546-551.
Singer et al., "The Effect of Chromium Picolinate and Biotin Supplementation on Glycemic Control in Poorly Controlled Patients with Type 2 Diabetes Mellitus: A Placebo-Controlled, Double-Blinded, Randomized Trial," Diabetes Technology & Therapeutics, 2006; 8(6): pp. 636-643.
Spady, D.K., Reverse Cholesterol Transport and Atherosclerosis Regression, 100:576-578 (1999).
Sreekanth et al., "Molecular basis of chromium insulin interactions", Biochemical and Biophysical Research Communications, 2008; 369: pp. 725-729.
Srinivasan et al., "Perchlorate: health effects and technologies for its removal from water resources," Int. J. Environ. Res. Public Health, 2009; 6: pp. 1418-1442.
Storlien et al., "Dietary fats and insulin action," Diabetologia, 1996, 39: pp. 621-631.
Striffler et al. "Dietary Chromium Decreases Insulin Resistance in Rats Fed a High-Fat, Mineral-Imbalanced Diet," Metabolism. 1998; 47(4): 396-400.
Sundberg et al., "Interactions of Histidine and Other Imidazole Derivatives with Transition D Metal Ions in Chemical and Biological Systems," Chemical Reviews, 1974; 74(4): pp. 471-517.
Supplementary European Search Report and Opinion dated Feb. 27, 2013 for EP Patent Application No. 10794738.4.
Szatmari, "The Epidemiology of Attention-Deficit Hyperactivity Disorders," Child Adolesc. Psychiat. Clin. North Am., 1992; 1(2): pp. 361-371.
Tanzi et al., "Twenty Years of the Alzheimer's disease Amyloid Hypothesis: A Genetic Perspective," Cell, 2005; 120: pp. 545-555.
Thomas et al., "The role of advanced glycation in reduced organic cation transport associated with experimental diabetes," JPET, 2004; 311(2): pp. 456-466.
Tuzcu et al., "Effect of Melatonin and Vitamin E on Diabetes-induced Learning and Memory Impairment in Rats," European Journal of Pharmacology, 2006; 537: pp. 106-110.
Uehara et al. "Chronic insulin hypoglycemia induces GLUT-3 protein in rat brain neurons," Am. J. Physiol., 1997; 272: pp. E716-E719.

(56) References Cited

OTHER PUBLICATIONS

Urberg et al., "Hypercholesterolemic effects of nicotinic acid and chromium supplementation" The Journal of Family Practice, 27(6):603-606 (1988).
Vincent "Menagerie of Chromium Supplements", Oct. 3, 2012, Chapter 7 in The Bioinorganic Chemistry of Chromium, pp. 169-188).
Wallin et al. "Glial Fibrillary Acidic Protein in the Cerebrospinal Fluid of Patients with Dementia," Dementia, 1996; 7: pp. 267-272.
Wang et al., "Homozygous Disruption of Pctp Modulates Atherosclerosis in Apolipoprotein E- Deficient Mice", J Lipid Res., 2006; 47: pp. 2400-2407.
Wang et al., "Involvement of Organic Cation Transporter 1 in Hepatic and Intestinal Distribution of Metformin," Journal of Pharmacology and Experimental Therapeutics, 2002; 302(2): pp. 510-515.
Wolever et al., "Beneficial effect of low-glycemic index diet in overweight NIDDM subjects," Diabetes Care, 1992;15(4): pp. 562-564.
Wolever et al., "Dietary recommendations for diabetes: high carbohydrate or high monounsaturated fat?" Nutrition Today, 1999; 34(2): pp. 73-77.
Wolever et al., "The glycemic index: methodology and clinical implications," Am. J. Clin. Nutr. 1991; 54: pp. 846-854.
Yang et al., "Differential effects of salen and manganese-salen complex (EUK-8) on the regulation of cellular cadmium uptake and toxicity," Toxicological Sciences, 2005; 85: pp. 551-559.
Yoritaka et al. "Immunohistochemical detection of 4-hydroxynonenal protein adducts in Parkinson disease", (1996) Proc. Natl. Acad. Sci. USA 93:2696-2701.
Zhang et al., "A high biotin diet improves the impaired glucose tolerance of long-term spontaneously hyperglycemic rats with non-insulin-dependent diabetes mellitus," J. Nutr. Sci., Vitaminol., 1996; 42: pp. 517-526.
Zhang et al., "Biotin administration improves the impaired glucose tolerance of streptozotocininduces diabetic Wistar rats," J. Ntr. Sci. Vitaminol., 1997; 43(3): pp. 271-280.
Zhang et al., "Dynamic expression of glucose transporters 1 and 3 in the brain of diabetic rats with cerebral ischemia reperfusion", Chin Med J., 2009, 122(17): pp. 1996-2001.
Atherton et al., "Muscle protein synthesis in response to nutrition and exercise", The Journal of Physiology. 2012;590(Pt 5): 1049-1057. doi: 10.1113/jphysiol.2011.225003.
Babault et al., "Pea proteins oral supplementation promotes muscle thickness gains during resistance training: A double-blind, randomized, Placebo-controlled clinical trial vs. Whey protein", J Int Soc Sports Nutr. 2015;12(1):1-9. doi:10.1186/s12970-014-0064-5.
Catoire et al., "The search for exercise factors in humans". The FASEB Journal. 2015;29.
Extended European Search Report for EP Application No. 08714104.0 dated Nov. 7, 2012.
Extended European Search Report for EP Application No. 10794738.4 dated Feb. 27, 2013.
Extended European Search Report for EP Application No. 16160735.3 dated May 2, 2016.
Furuyashiki et al., "Effects of ingesting highly branched cyclic dextrin during endurance exercise on rating of perceived exertion and blood components associated with energy metabolism", Biosci Biotechnol Biochem. 2014;78(12):2117-2119. doi:10.1080/09168451. 2014.943654.
Guimaraes-Ferreira et al., "Synergistic effects of resistance training and protein intake: practical aspects", Nutrition. 2014;30(10):1097-1103. doi:10.1016/j.nut.2013.12.017.
Hua et al., "Molecular Mechanisms of Chromium in Alleviating Insulin Resistance", The Journal of Nutritional Biochemistry. 2012;23(4):313-319. doi:10.1016/j.jnutbio.2011.11.001.
Keller et al., "Strength and muscle mass loss with aging process. Age and strength loss", Muscles, Ligaments and Tendons Journal. 2013;3(4):346-350.
Komorowski et al., "The effect of the addition of an amylopectin/chromium complex to increasing doses of whey protein on muscle protein synthesis in rats", Proceedings of the Fourteenth International Society of Sports Nutrition (ISSN) Conference and Expo, Journal of The International Society of Sports Nutrition (2017) 14(Suppl 2): 31, Abstract P44, pp. 20-21.
Komorowski et al., "The Effects of Velositol on Exercised-Induced Myokines", American College of Nutrition 2017 Conference, 1 page.
MacDougall et al., "The time course for elevated muscle protein synthesis following heavy resistance exercise", Can J Appl Physiol. 1995;20(4):480-486.
Nutrition 21, "Nutrition 21 Presents Three Preclinical Scientific Studies on Velositol at ISSN", Globe Newswire, Jun. 28, 2017, retrieved from https://www.globenewswire.com/en/news- release/2017/06/28/1254039/0/en/Nutrition-21-Presents-Three-Preclinical-Scientific-Studies-on-Velositol-at-ISSN.html.
Reidy et al., "Role of Ingested Amino Acids and Protein in the Promotion of Resistance Exercise-Induced Muscle Protein Anabolism", The Journal of Nutrition. 2016;146(2):155-183. doi:10.3945/jn.114.203208.
Schinetsky, "Velositol—The Protein-Potentiating Powerhouse", 2017 https://www.tigerfitness.com/blogs/supplements/velositol-the-protein-potentiating powerhouse.
So et al., "Exercise-induced myokines in health and metabolic diseases", Integrative Medicine Research. 2014;3(4):172-179. doi:10.1016/j.imr.2014.09.007.
Subbotina et al., "Musclin is an activity-stimulated myokine that enhances physical endurance", PNAS. 2015;112(52):16042-16047.
United Kingdom Search Report for Application No. GB2019331.4 dated Jan. 11, 2021 (Our Reference No. NTW-05202).
Wiseman et al., "Amylopectin starch induces nonreversible insulin resistance in rats". J Nutr. 1996;126(2):410-415.
Ziegenfuss et al., "Effects of an amylopectin and chromium complex on the anabolic response to a suboptimal dose of whey protein", Journal of the International Society of Sports Nutrition (2017) 14:6.
Notice of Allowance for Application U.S. Appl. No. 16/366,936 dated Oct. 18, 2023.

* cited by examiner

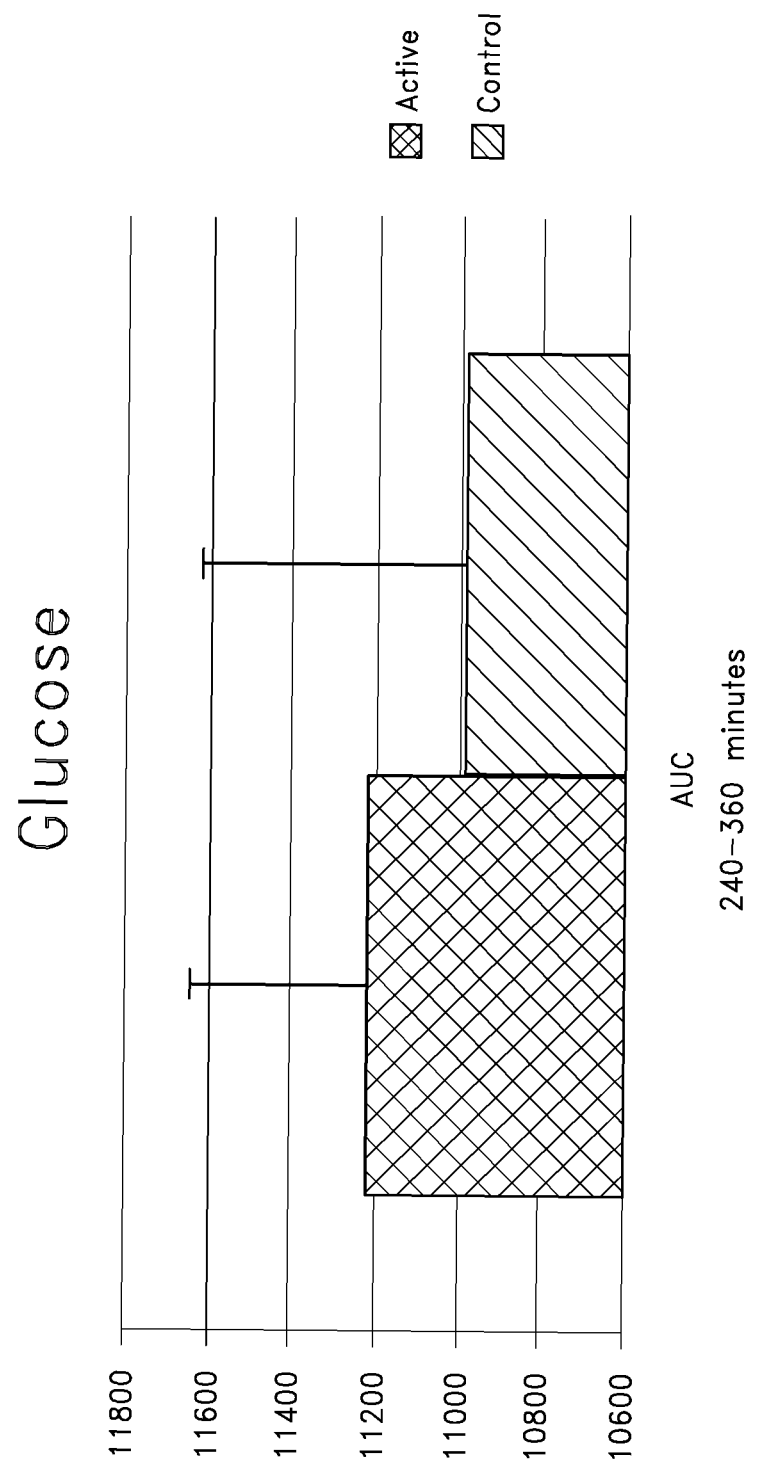

CHROMIUM CONTAINING COMPOSITIONS FOR IMPROVING HEALTH AND FITNESS

INCORPORATION BY REFERENCE TO RELATED APPLICATIONS

Any and all priority claims identified in the Application Data Sheet, or any correction thereto, are hereby incorporated by reference under 37 CFR 1.57. This application claims the benefit of U.S. Provisional Application No. 62/285,014, filed Feb. 11, 2016. The aforementioned application is incorporated by reference herein in its entirety, and is hereby expressly made a part of this specification.

FIELD

The present disclosure relates to compositions for use by those engaging in exercise training, both in elite and amateur athletes, as well as in exercise naïve individuals.

BACKGROUND

Embodiments relate to compositions that comprise, consist essentially of, or consist of a chromium complex and a starch for improving muscle health. In some aspects, the composition includes a chromium picolinate complex, a chromium histidinate complex and amylopectin. In some aspects, the composition includes a chromium-amylopectin complex. In some aspects, the composition also includes at least one amino acid source. The amino acid source may comprise amino acids that are essential for muscle growth. The amino acids may include one or more of histidine, isoleucine, leucine, lysine, methionine, phenylalanine, threonine, tryptophan, and valine. Other embodiments relate to the use of such compositions. These compositions are useful for, inter alia, increasing amino acid absorption, increasing protein synthesis, increasing exercise tolerance, increasing lean muscle mass, increasing skeletal muscle hypertrophy, increasing muscle power, increasing muscle endurance, increasing muscle strength, increasing muscle fractional synthesis rate (FSR), decreasing delayed onset muscle soreness, decreasing muscle protein breakdown, and/or decreasing fat mass. In some embodiments, the compositions may be useful for treating or preventing sarcopenia. In some aspects the chromium source is one or more chromium complexes.

Protein Transport and Exercise

Muscles are composed of the contractile proteins myosin and actin, which together form the myofibrils. Contraction occurs when actin ratchets over myosin, shortening the length of myofibrils. Physical activity is necessary to maintain normal muscle mass and strength and prevent muscle atrophy. Resistance training results in increased skeletal muscle size (hypertrophy), strength, and endurance, as a biological adaptation to addressing the increased workload. This adaptation results from changes in the rates of protein synthesis and/or breakdown during and after resistance training. Such adaptation requires increased amino acid availability, both to prevent excess muscle tissue breakdown and to facilitate protein synthesis.

This system requires adequate nutrition to provide the amino acids that form the protein, but beyond that, the pathways are controlled by activating factors. Meeting the increased demand for amino acids post-exertion allows the protein synthesis machinery to be up-regulated, thus allowing for maintenance and/or growth of muscle mass.

Protein intake provides a muscle protein synthesis dose-response up to a total dose of approximately 20 grams of protein. Protein intake in excess of the 20 gram ceiling does not result in increased muscle protein synthesis, and can be harmful, for example, by stimulating amino acid oxidation. Moore et al., *Am. J. Clin. Nutr.*, vol. 89, pp. 161-168 (2009).

Glucose Transport and Exercise

Exercise training may have many effects on skeletal muscle, including increased glucose transport. For a short period after exercise, skeletal muscle glucose transport is insulin-independent. Subsequently, as the acute effect of exercise on glucose transport wears off, skeletal muscles experience a substantial increase in the sensitivity of the glucose transport process to stimulation by insulin and other activators of glucose transport.

Post-Exercise Recovery

Effective post exercise recovery is essential for amateur and elite athletes to maintain performance, and for individuals new to exercise to derive the most benefit from exercise training and continue with their exercise regimen. Delayed onset muscle soreness (DOMS) is a familiar experience for the elite or novice athlete. Symptoms can range from muscle tenderness to severe debilitating pain. DOMS is most prevalent at the beginning of the sporting season when athletes are returning to training following a period of reduced activity. DOMS is also common when athletes are first introduced to certain types of activities regardless of the time of year. Resistance exercise induces micro-injury at a greater frequency and severity than other types of muscle actions. Proper recovery both from a general exercise regime, as well as from intense training regimes and DOMS requires replenishing muscle glycogen stores, rehydration, and protein supplementation to maintain and/or increase lean body mass.

Metabolism

During growth, pregnancy, and muscle development, metabolism is primarily in the anabolic phase, that is, more muscle is added than is broken down. In contrast, the catabolic phase of muscle growth and development results in a net loss of lean muscle. This can occur through both overtraining, and lack of proper nutrition.

The anabolic/catabolic balance is an important factor not only in healthy mammals during growth and development but also in disease and disease management. Muscle wasting in patients with restricted movement is common clinical issue. For example, patients in intensive care often become catabolic quickly after admission. Similarly, astronauts become catabolic in weightless environment of space and begin losing muscle tissue and strength almost immediately. Extreme loss of muscle tissue leads to a condition termed cachexia, which is often seen in cancer, trauma, and burn patients. A shift toward catabolism also occurs as a normal part of aging.

Individuals of all ages and athletic abilities can benefit from enhanced muscle development, i.e., prolonging the anabolic phase. However, methods such as anabolic steroids are not healthy or safe for most individuals. Rather, using in weight and/or cardiovascular training intense enough to reach the anaerobic threshold, results in a constant flux of tearing down muscle fibers (catabolism) and rebuilding the fibers (anabolism). This cycle of rebuilding is especially rapid during the 90 minutes following exercise (the "anabolic window").

The Role of Chromium

Dietary supplementation of chromium to normal individuals has been reported to lead to improvements in glucose tolerance, serum lipid concentrations, including high-density lipoprotein cholesterol, insulin and insulin binding. Anderson, 1986 Clin. Psychol. Biochem. 4:31-41. Supplemental chromium in the trivalent form, e.g. chromic chloride, is associated with improvements of risk factors associated with adult-onset (Type 2) diabetes and cardiovascular disease.

Chromium is a nutritionally essential trace element. The necessity of dietary chromium was established in 1959 by Schwartz. Schwartz, "Present Knowledge in Nutrition," page 571, fifth edition (1984, the Nutrition Foundation, Washington, D.C.). Chromium depletion is characterized by the disturbance of glucose, lipid and protein metabolism and by a shortened lifespan. Chromium is essential for optimal insulin activity in all known insulin-dependent systems. Boyle et al., 1977 Southern Med. J. 70:1449-1453. Insufficient dietary chromium has been linked to both maturity-onset diabetes and to cardiovascular disease.

The principal energy sources for the body are glucose and fatty acids. Chromium depletion results in biologically ineffective insulin and compromised glucose metabolism. Under these conditions, the body relies primarily upon lipid metabolism to meet its energy requirements, which can lead to the production of elevated amounts of acetyl-CoA and ketone bodies. In some cases, some of the acetyl-CoA can be diverted to increased cholesterol biosynthesis, resulting in hypercholesterolemia. As such, glycosuria, hypercholesterolemia, and often ketoacidosis are often associated with diabetes mellitus. The accelerated atherosclerotic process seen in diabetics is associated with hypercholesterolemia Boyle et al., supra.

Chromium functions as a cofactor for insulin. It binds to the insulin receptor and potentiates many, and perhaps all, of its functions. Boyle et al., supra. These functions include, but are not limited to, the regulation of carbohydrate and lipid metabolism. Present Knowledge in Nutrition, supra, at p. 573-577. The introduction of inorganic chromium compounds per se into individuals is not particularly beneficial. Chromium must be converted endogenously into an organic complex or must be consumed as a biologically active molecule. Only about 0.5% of ingested inorganic chromium, however, is assimilated into the body. Only 1-2% of most organic chromium compounds are assimilated into the body. Recommended Daily Allowances, Ninth Revised Edition, The National Academy of Sciences, page 160, 1980.

Metal coordination complexes of picolinic acid (pyridine-2-carboxylic acid) have the following structural formula:

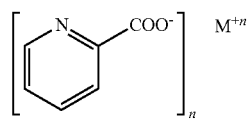

wherein M represents the metallic cation and n is equal to the cation's valence. For example, when M is Cr and n=3, then the compound is chromic tripicolinate. Other chromium picolinates include chromic monopicolinate and chromic dipicolinate. The U.S. Recommended Daily Intake (RDI) of chromium is 120 µg.

U.S. Pat. Nos. 5,087,623; 5,087,624; and 5,175,156, disclose the use of chromium tripicolinate for supplementing dietary chromium, reducing hyperglycemia and stabilizing serum glucose, increasing lean body mass and reducing body fat, and controlling serum lipid levels, including the lowering of undesirably high serum LDL-cholesterol levels and the raising of serum High Density Lipid (HDL)-cholesterol levels. U.S. patent application Ser. Nos. and 10/090, 038 and 11/136,794, disclose the use of high doses of chromium complexes (providing between 1,000 and 10,000 µg/day) and biotin for treating dyslipidemia, and increasing serum HDL levels.

Nicotinic acid and picolinic acid form coordination complexes with monovalent, divalent and trivalent metal ions and facilitate the absorption of these metals by transporting them across intestinal cells and into the bloodstream.

Other compounds such as non-steroidal anti-inflammatory drugs (NSAIDs) such as aspirin and indomethachin have also been shown to facilitate chromium absorption. For Example, Davis et al. demonstrated that orally administered $CrCl_3$ is facilitated by the non-steroidal anti-inflammatory drugs (NSAIDs) aspirin and indomethacin. Davis et al., 1995, J. Nutrition Res. 15:202-210 (1995); Kamath et al., 1997, J. Nutrition 127:478-482. These drugs inhibit the enzyme cyclooxygenase which converts arachidonic acid to various prostaglandins, resulting in inhibition of intestinal mucus formation and lowering of intestinal pH which facilitates chromium absorption.

U.S. Pat. No. 4,315,927 teaches that when selected essential metals are administered to mammals as exogenously synthesized coordination complexes of picolinic acid, they are directly available for absorption without competition from other metals. These complexes are safe, inexpensive, biocompatible and easy to produce.

SUMMARY

This application is based in part on the surprising discovery that certain chromium complexes, when provided in combination with starch and/or protein, provide an unexpected increase in amino acid absorption, protein synthesis, exercise tolerance, lean muscle mass, skeletal muscle hypertrophy, muscle power, muscle endurance, muscle strength, FSR, and decreasing delayed onset muscle soreness, muscle protein breakdown, and fat mass. In some aspects, the chromium complexes, when provided in combination with starch and/or protein can be used to treat and/or prevent muscle loss and/or sarcopenia.

Some embodiments provide a method for increasing muscle mass, comprising: administering an effective amount of a chromium complex and a starch in combination with an amount of a protein to a subject, wherein the subject's lean muscle mass is increased relative to providing the amount of the protein alone.

Some embodiments provide a method for decreasing delayed onset muscle soreness, comprising: administering an effective amount of a chromium complex and a starch in combination with an amount of a protein to a subject, wherein the subject's delayed onset muscle soreness is decreased relative to providing the amount of the protein alone.

Some embodiments provide a method for increasing plasma levels of essential amino acids, comprising: administering an effective amount of a chromium complex and a starch in combination with an amount of a protein to a subject, wherein the subject's plasma levels of essential amino acids are increased relative to providing the amount of the protein alone.

Some embodiments provide a method for increasing muscle uptake of branched chain amino acids, comprising: administering an effective amount of a chromium complex and a starch in combination with an amount of a protein to a subject, wherein the subject's muscle uptake of branched chain amino acids is increased relative to providing the amount of the protein alone.

Some embodiments provide a method of increasing a rate of muscle hypertrophy comprising: administering an effective amount of a chromium complex and a starch in combination with an amount of a protein to a subject temporally proximate to a resistance exercise, wherein the subject's rate of muscle hypertrophy is increased relative to providing the amount of the protein alone.

Some embodiments provide a method of increasing a fractional rate of muscle protein synthesis comprising: administering an effective amount of a chromium complex and a starch in combination with an amount of a protein to a subject temporally proximate to a resistance exercise, wherein the subject's fractional rate of muscle protein synthesis is increased relative to providing the amount of the protein alone.

Some embodiments provide a method of ameliorating muscle soreness comprising: identifying a subject suffering from muscle soreness; and administering an effective amount of a chromium complex and a starch in combination with an amount of a protein to the subject, wherein the subject's muscle soreness is decreased relative to providing the amount of the protein alone.

Some embodiments provide a method of increasing exercise stamina comprising: identifying a subject in need of increased exercise stamina; and administering an effective amount of a chromium complex and a starch in combination with an amount of a protein to a subject prior to an exercise, wherein the subject's exercise stamina is increased relative to providing the amount of the protein alone.

Some embodiments further comprise administering a compound selected from the group consisting of caffeine, creatine, creatine hydrochloride, creatine monohydrate, taurine, guarana, vitamin C, vitamin $B_1$, vitamin $B_2$, vitamin $B_3$, vitamin $B_5$, vitamin $B_6$, vitamin $B_7$, vitamin $B_9$, and vitamin $B_{12}$, and combinations thereof.

In some embodiments, the protein is a whey protein. In some embodiments, the whey protein is hydrolyzed. In some embodiments, the protein source is branched chain amino acids. In some embodiments, the protein is a vegetable protein. In some embodiments, the protein comprises at least one essential amino acid. In some embodiments, the at least one essential amino acid is leucine. In some embodiments, the starch is amylopectin.

In some embodiments, the chromium complex is selected from the group consisting of chromium picolinate, chromic tripicolinate, chromium nicotinate, chromic polynicotinate, chromium chloride, chromium histidinate, chromium trihistidinate, and chromium yeasts, and combinations thereof. In some embodiments, the chromium complex consists essentially of chromium picolinate and chromium histidinate. In some embodiments, the chromium complex consists essentially of chromium picolinate. In some embodiments, the chromium complex consists essentially of chromium histidinate. In some embodiments, the effective amount of the chromium and the starch is provided as a chromium-starch complex. In some embodiments, the amount of the protein is an amount of the protein consumed in a single day. In some embodiments, the amount of the protein is administered at least one hour after the effective amount of the chromium and the starch.

Some embodiments provide a nutritional supplement comprising: a first amount of a chromium complex; and a second amount of amylopectin; wherein the first amount and the second amount are formulated as a single dose and are effective to increase muscle mass in a subject.

In some embodiments, the chromium is present between about 0.001% (w/w) and about 3% (w/w). In some embodiments, the chromium is present between about 0.005% (w/w) and about 2% (w/w). In some embodiments, the chromium is present between about 0.01% (w/w) and about 1% (w/w). In some embodiments, the supplement is a solid. In some embodiments, the solid is a powder. In some embodiments, the supplement is a liquid. In some embodiments, the liquid is a concentrated formulation. In some embodiments, the supplement further comprises at least one of a sweetener and a flavoring agent.

Some embodiments provide a method of making a composition comprising chromium picolinate, chromium histidinate, at least one protein source, at least one starch, and at least one excipient, comprising: wet milling the at least one protein source and the least one starch to form a first mixture; spray drying the first mixture; and dry blending the first mixture with chromium picolinate and chromium histidinate to form a second mixture.

Some embodiments provide a method of stimulating muscle synthesis, comprising: identifying a person in need of increased muscle synthesis; and administering an effective amount of a chromium/amylopectin complex in combination with an amount of a protein, wherein the chromium/amylopectin complex causes increased muscle mass in a subject compared to a subject receiving a composition consisting essentially of the amount of the protein alone.

Some embodiments provide a method of treating muscle loss comprising: identifying a person in need of treatment for muscle loss; and administering an effective amount of a chromium/amylopectin complex in combination with an amount of a protein, wherein the chromium/amylopectin complex causes increased muscle mass in a subject compared to a subject receiving a composition consisting essentially of the amount of the protein alone.

In some embodiments, the person is experiencing sarcopenia. In some embodiments, the administration of the chromium/amylopectin complex causes increased muscle mass in a subject compared to a subject receiving the same diet without the chromium/amylopectin complex.

Some embodiments provide a method of increasing muscle power comprising: administering a composition having a chromium complex to provide a first bioavailable amount of chromium to a subject and a starch source to provide a second bioavailable amount of starch to the subject; and administering an amount of a protein to the subject, wherein the subject's muscle power is increased relative to administering a composition consisting essentially of the amount of the protein alone.

Some embodiments provide a nutritional supplement comprising chromium picolinate, chromium histidinate, and amylopectin, wherein the chromium and amylopectin are present in a weight ratio from at least about 1:1 to about 1:2000. In some embodiments, the chromium is present between about 100 mcg and about 2,000 mcg. In some embodiments, the chromium is present between about 500 mcg and about 1,500 mcg. In some embodiments, the chromium is present at about 1,000 mcg. In some embodiments, the amylopectin is present between about 100 mg and about 3,000 mg. In some embodiments, the amylopectin is present between about 1,000 mg and about 2,500 mg. In some embodiments, the amylopectin is present between about 1,500 mg and about 2,000 mg. In some embodiments, the amylopectin is derived from waxy maize.

Some embodiments provide a method for treating sarcopenia, comprising: administering an effective amount of a chromium complex and a starch in combination with an amount of a protein to a subject.

A method of treating muscle loss comprising: identifying a person in need of treatment for muscle loss; and administering an effective amount of a chromium/amylopectin complex. In some embodiments, the person is experiencing sarcopenia. In some embodiments, the person is elderly. In some embodiments, the administration of the chromium/amylopectin complex causes increased muscle mass in a subject compared to a subject receiving the same diet without the chromium/amylopectin complex.

Some embodiments provide a method for increasing muscle mass. For example, a method may include administering an effective amount of a chromium complex to a subject in combination with a starch and a protein. The subject's lean muscle mass may be increased relative to providing the protein and starch alone. In another example, a method may include administering an amount of chromium and starch to a subject. The subject may consume an amount of protein. The subject's lean muscle mass may be increased relative to consuming the amount of protein alone. In some embodiments the muscle mass is increased by about 1 to 10%; 1.2 to 9%; 1.4 to 8%; 1.6 to 7%; 1.8 to 6%; 2 to 5%; 3 to 4%; or any value in between. In some embodiments the muscle mass is increased by 1%, 2%, 3%, 4%, 5%, 6%, 7%, 8%, 9%, 10%, or any value in between.

Some embodiments provide a method for decreasing delayed onset muscle soreness. For example, a method may include administering an effective amount of a chromium complex to a subject in combination with a protein and a starch. The subject's delayed onset muscle soreness may be decreased relative to providing protein and starch alone. In another example, a method may include administering an amount of chromium and starch to a subject. The subject may consume an amount of protein. The subject's onset muscle soreness may be decreased relative to consuming the amount of protein alone. In some embodiments the delayed onset muscle soreness is decreased by about 10 to 100%; 15 to 95%; 20 to 90%; 25 to 85%; 30 to 80%; 35 to 75%; 45 to 70%; or any value in between. In some embodiments the delayed onset muscle soreness is decreased by 10%, 20%, 30%, 40%, 50%, 60%, 70%, 80%, 90%, 100%, or any value in between.

Some embodiments provide a method for increasing plasma levels of essential amino acids. For example, a method may include administering an effective amount of a chromium complex to a subject in combination with a protein and a starch. The subject's plasma levels of essential amino acids may be increased relative to providing protein and starch alone. In another example, a method may include administering an amount of chromium and starch to a subject. The subject may consume an amount of protein. The subject's plasma levels of essential amino acids may be increased relative to consuming the amount of protein alone. In some embodiments the plasma levels of essential amino acids is increased by about 5 to 100%; 10 to 90%; 15 to 80%; 20 to 70%; 25 to 60%; 30 to 50%; 35 to 40%; or any value in between. In some embodiments the plasma levels of essential amino acids is increased by 5%, 10%, 15%, 20%, 30%, 40%, 50%, 60%, 70%, 80%, 90%, or any value in between. In some embodiments, the essential amino acids are selected from phenylalanine, valine, threonine, tryptophan, methionine, leucine, isoleucine, lysine, and histidine. In some embodiments, the essential amino acids are leucine and/or isoleucine.

Some embodiments provide a method for increasing muscle uptake of branched chain amino acids. For example, a method may include administering an effective amount of a chromium complex in combination with a protein and a starch to a subject. The subject's muscle uptake of branched chain amino acids may be increased relative to providing protein and starch alone. In another example, a method may include administering an amount of chromium and starch to a subject. The subject may consume an amount of protein. The subject's uptake of branched chain amino acids may be increased relative to consuming the amount of protein alone. In some embodiments the muscle uptake of branched chain amino acids is increased by about 5 to 100%; 10 to 90%; 15 to 80%; 20 to 70%; 25 to 60%; 30 to 50%; 35 to 40%; or any value in between. In some embodiments the muscle uptake of branched chain amino acids is increased by 5%, 10%, 15%, 20%, 30%, 40%, 50%, 60%, 70%, 80%, 90%, or any value in between. In some embodiments, the branched chain amino acids are selected from valine, threonine, leucine, and isoleucine. In some embodiments, the branched chain amino acids amino acids are leucine and/or isoleucine.

Some embodiments provide a method of increasing rate of muscle hypertrophy. For example, a method may include administering an effective amount of a chromium complex in combination with a protein and a starch to a subject. The administration may be temporally proximate to resistance exercise. The subject's rate of muscle hypertrophy may be increased relative to providing protein and starch alone. In another example, a method may include administering an amount of chromium and starch to a subject. The subject may consume an amount of protein. The subject's rate of muscle hypertrophy may be increased relative to consuming the amount of protein alone. In some embodiments the rate of muscle hypertrophy is increased by about 1 to 10%; 1.2 to 9%; 1.4 to 8%; 1.6 to 7%; 1.8 to 6%; 2 to 5%; 3 to 4%; or any value in between. In some embodiments the rate of muscle hypertrophy is increased by 1%, 2%, 3%, 4%, 5%, 6%, 7%, 8%, 9%, 10%, or any value in between.

Some embodiments provide a method of increasing the fractional rate of muscle protein synthesis. For example, a method may include administering an effective amount of a chromium complex in combination with a protein and a starch to a subject. The administration may be temporally proximate to resistance exercise. The subject's fractional rate of muscle protein synthesis may be increased relative to providing protein and starch alone. In another example, a method may include administering an amount of chromium and starch to a subject. The subject may consume an amount of protein. The consumption of protein may be temporally proximate to resistance exercise. The subject's rate of muscle protein synthesis may be increased relative to consuming the amount of protein alone. In some embodiments the fractional rate of muscle protein synthesis is increased by about 1 to 10%; 1.2 to 9%; 1.4 to 8%; 1.6 to 7%; 1.8 to 6%; 2 to 5%; 3 to 4%; or any value in between. In some embodiments the fractional rate of muscle protein synthesis is increased by 1%, 2%, 3%, 4%, 5%, 6%, 7%, 8%, 9%, 10%, or any value in between.

Some embodiments provide a method of ameliorating muscle soreness. For example, a method may include identifying a subject suffering from muscle soreness and administering an effective amount of a chromium complex in combination with a protein and a starch to the subject. The subject's muscle soreness may be decreased relative to providing protein and starch alone. In another example, a method may include administering an amount of chromium and starch to a subject. The subject may consume an amount of protein. The subject's muscle soreness may be decreased in less time relative to consuming the amount of protein alone. In some embodiments the muscle soreness is ameliorated by about 10 to 100%; 15 to 95%; 20 to 90%; 25 to 85%; 30 to 80%; 35 to 75%; 45 to 70%; or any value in between. In some embodiments the muscle soreness is ameliorated by 10%, 20%, 30%, 40%, 50%, 60%, 70%, 80%, 90%, 100%, or any value in between.

Some embodiments provide a method of increasing exercise stamina. For example, a method may include identifying a subject in need of increased exercise stamina and administering an effective amount of a chromium complex in combination with a protein and a starch to the subject. The administration may be prior to beginning exercise. The subject's exercise stamina may be increased relative to providing protein and starch alone. In another example, a method may include administering an amount of chromium and starch to a subject. The subject may consume an amount of protein. The subject's stamina may be increased relative to consuming the amount of protein alone. In some embodiments the exercise stamina is increased by about 1 to 20%; 2 to 18%; 3 to 17%; 4 to 16%; 5 to 15%; 6 to 14%; 7 to 12%; or any value in between. In some embodiments the exercise stamina is increased by 1%, 2%, 3%, 4%, 5%, 6%, 7%, 8%, 9%, 10%, 11%, 12%, 13%, 14%, 15%, 16%, 17%, 18%, 19%, 20%, or any value in between.

Some embodiments provide a method of treating or preventing muscle loss. For example, a method may include identifying a subject in the need of a treatment to prevent muscle loss. Such a subject may have sarcopenia. The method may include administering an effective amount of a chromium complex in combination with a starch to the subject. The subject's muscle loss may be stopped and/or reversed. In another example, a method may include administering an amount of chromium and starch to a subject. The subject may consume an amount of protein. The subject's muscle loss may be stopped and/or reversed. In some embodiments the muscle loss is reduced by about 10 to 100%; 15 to 95%; 20 to 90%; 25 to 85%; 30 to 80%; 35 to 75%; 45 to 70%; or any value in between. In some embodiments the muscle loss is reduced by 10%, 20%, 30%, 40%, 50%, 60%, 70%, 80%, 90%, 100%, or any value in between.

Some embodiments provide a method of increasing FSR. For example, the method may include administering an effective amount of a chromium complex in combination with a protein and a starch to a subject, which increases FSR relative to an equivalent dose of protein and starch alone. In some embodiments, the method may include administering an effective amount of a chromium complex in combination with a protein and a starch to a subject, which provides an equivalent FSR relative to a higher dose of protein and starch alone. In some embodiments, the dose of protein and starch alone is 1.3-fold, 1.5-fold, 1.8-fold, 2-fold, 2.3-fold, 2.5-fold, 2.8-fold, 3-fold, 3.3-fold, 3.5-fold, 3.8-fold, 4-fold, 4.3-fold, 4.5-fold, 4.8-fold, or 5-fold higher, or any value in between.

Some embodiments further comprise administering a compound selected from caffeine, creatine, creatine hydrochloride, creatine monohydrate, taurine, guarana, vitamin C, vitamin B1, vitamin B2, vitamin B3, vitamin B5, vitamin B6, vitamin B7, vitamin B9, and vitamin B12, or any combination of the foregoing.

In some embodiments, the protein is whey protein. In some embodiments, the whey protein is hydrolyzed. In some embodiments, the starch is amylopectin.

In some embodiments, the chromium complex is selected from chromium picolinate, chromic tripicolinate, chromium nicotinate, chromic polynicotinate, chromium chloride, chromium histidinate, chromium trihistidinate, and chromium yeasts, or any combination of the foregoing. In some embodiments, the chromium complex is selected from chromium picolinate, chromic tripicolinate, chromium histidinate, chromium trihistidinate and a combination of any of the foregoing.

In some embodiments, the chromium complex consists essentially of chromium picolinate and chromium histidinate. In some embodiments, the chromium complex consists essentially of chromium picolinate. In some embodiments, the chromium complex consists essentially of chromium histidinate.

Some embodiments provide a nutritional supplement. The supplement may include a first amount of a Chromium/Amylopectin Complex. The supplement may also include a second amount of protein. The first amount of the Chromium/Amylopectin Complex may be provided in an amount that causes an increase in muscle mass in a subject to a greater extent than providing a composition consisting essentially of the second amount of protein.

In some embodiments, the chromium is present between about 0.001% (w/w) to about 3% (w/w). In some embodiments, the chromium is present between about 0.005% (w/w) to about 2% (w/w). In some embodiments, the supplement is a solid. In some embodiments, the solid is a powder. In some embodiments, the supplement is a liquid. In some embodiments, the liquid is a concentrated formulation. In some embodiments, the supplement further comprises at least one of a sweetener and a flavoring agent.

Some embodiments provide a method of making a composition comprising chromium picolinate, chromium histidinate, at least one protein source, at least one starch, and at least one excipient. The method may include wet milling the at least one protein source and the least one starch to form a first mixture, spray drying the first mixture, and dry blending the first mixtures with chromium picolinate and chromium histidinate to form a second mixture.

Some embodiments provide a method of stimulating muscle synthesis comprising identifying a person in need of increased muscle synthesis. For example, a method may include administering an effective amount of a Chromium/Amylopectin Complex in combination with an amount of protein. The Chromium/Amylopectin Complex may cause an increase in muscle mass in a subject compared to a subject receiving a composition consisting essentially of the amount of protein and amylopectin alone.

Some embodiments provide a nutritional supplement comprising chromium picolinate, chromium histidinate, and amylopectin, wherein the chromium and amylopectin are present in a ratio from at least about 1:1 to about 1:2000, or any ratio in between. Some embodiments provide a nutritional supplement comprising chromium picolinate, chromium histidinate, and amylopectin, wherein the chromium and amylopectin are present in a ratio of 1:1, 1:5, 1:10, 1:20, 1:50, 1:100, 1:200, 1:300, 1:400, 1:500, 1:600, 1:700, 1:800, 1:900, 1:1000, 1:1200, 1:1400, 1:1600, 1:1800, 1:2000, or any ratio in between. In some embodiments, the chromium and amylopectin are present in a ratio of about 1:1 to about 1:2000, about 1:10 to about 1:1800, about 1:20 to about 1:1600, about 1:40 to about 1:1400, about 1:60 to about 1:1200, about 1:80 to about 1:1000, about 1:100 to about 1:800, about 1:150 to about 1:600, about 1:200 to about 1:400, or any ratio in between.

In some embodiments, the total chromium present in the composition is between about 10 mcg to about 2,000 mcg. In some embodiments, the total chromium present in the composition is between about 10 to about 2,000 mcg, about 50 to about 1,800 mcg, about 100 to about 1,600 mcg, about 200 to about 1,400 mcg, about 300 to about 1,200 mcg, about 400 to about 1000 mcg, about 500 to about 800 mcg, or any amount in between.

In some embodiments, the amylopectin is present between about 100 mg to about 3,000 mg, or any amount in between. In some embodiments, the amylopectin is present between about 1,000 mg to about 2,500 mg, or any amount in between. In some embodiments, the amylopectin is present between about 1,500 mg to about 2,000 mg, or any amount in between. In some embodiments, the amylopectin is derived from waxy maize.

In some embodiments, the chromium is selected from chromium picolinate, chromic tripicolinate, chromium nicotinate, chromic polynicotinate, chromium chloride, chromium histidinate, chromium trihistidinate, and chromium yeasts, or any combination of the foregoing. In some embodiments, the chromium consists essentially of chromium picolinate and chromium histidinate. In some embodiments, the chromium consists essentially of chromium picolinate. In some embodiments, the chromium consists essentially of chromium histidinate.

In some embodiments, the composition comprises about 500 mcg chromium from chromium histidinate, about 500 mcg of chromium from chromium picolinate, and about 2,000 mg amylopectin. In some embodiments, the composition further comprises about 5 to about 20 grams of an amino acid source. In some embodiments, the amino acid source is whey protein. In some embodiments, the composition is formulated for combining with a protein shake or workout recovery beverage.

In some embodiments, the nutritional supplement further comprises a compound selected from caffeine, creatine, creatine hydrochloride, creatine monohydrate, taurine, guarana, vitamin C, vitamin B1, vitamin B2, vitamin B3, vitamin B5, vitamin B6, vitamin B7, vitamin B9, and vitamin B12, or any combination of the foregoing. Any of the features of an embodiment is applicable to all other embodiments identified herein. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other embodiments.

BRIEF DESCRIPTION OF THE DRAWINGS

FIGS. 6, 6A, and 6B illustrate changes in mean±SD plasma glucose. While the two-way ANOVA was not significant (P=0.22) for a difference between trials, within-trial increases were statistically significant for only Trial A at all time points after 300 min (i.e. 330 min, 360 min, 390 min, and 480 min).

The results indicate that the Active trial yielded a more robust response (≈32%) in FSR versus the Control trial (21%; P=0.001). Specifically, in the Active trial, pre-treatment FSRpl was 0.0507±0.01% and post-treatment FSRpl was 0.0745±0.016%. In the Control trial, pre-treatment FSRic was 0.0532±0.023% while post-treatment FSRic was 0.0647±0.013%. The significant response of the Active trial was achieved in light of similar leucine and essential amino acid concentrations resultant from each treatment. A potential explanation for improved response of the Active trial may lie in its insulinogenic properties. Peak insulin response of the Active trial trended towards significance (p=0.09).

Figure 1:
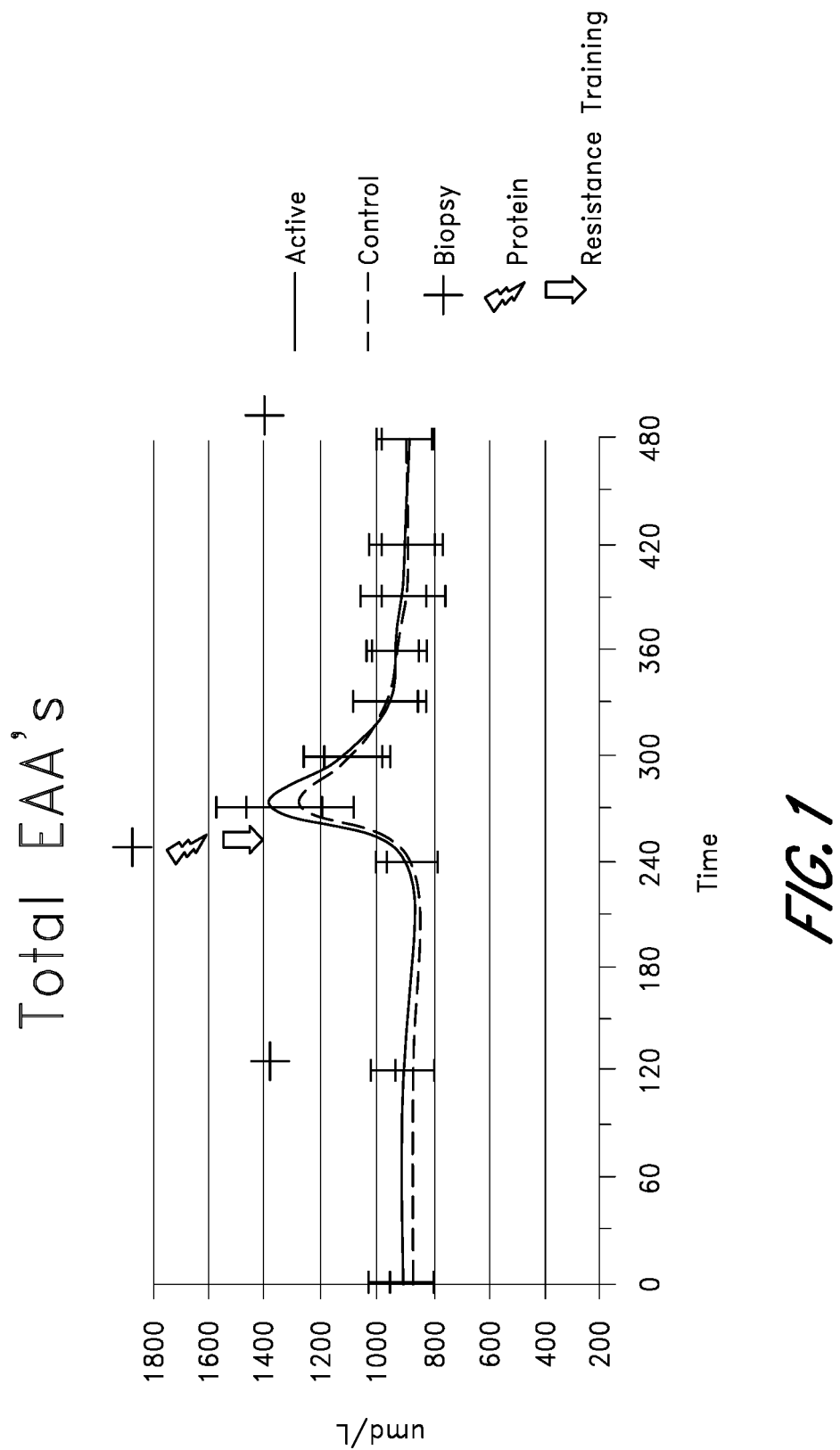
FIG. 1 and FIG. 2 illustrate changes in mean±SD plasma essential amino acids (EAAs). Although within-trial increases were statistically significant for both Trial A and Trial B at various time points (i.e. 270 min, 300 min), no overall or between-group (pairwise) differences were noted.
Figure 2:
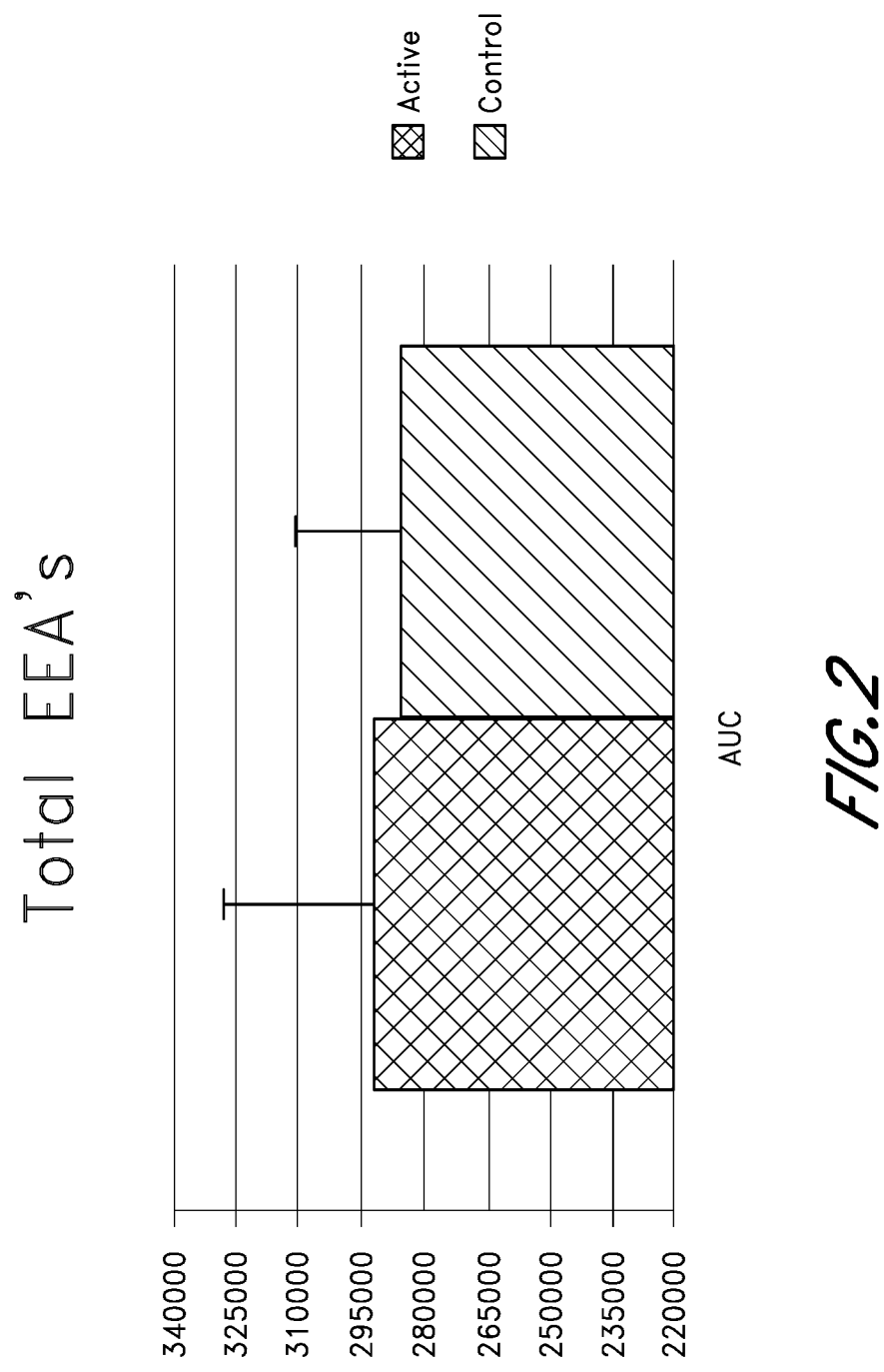
Figure 3:
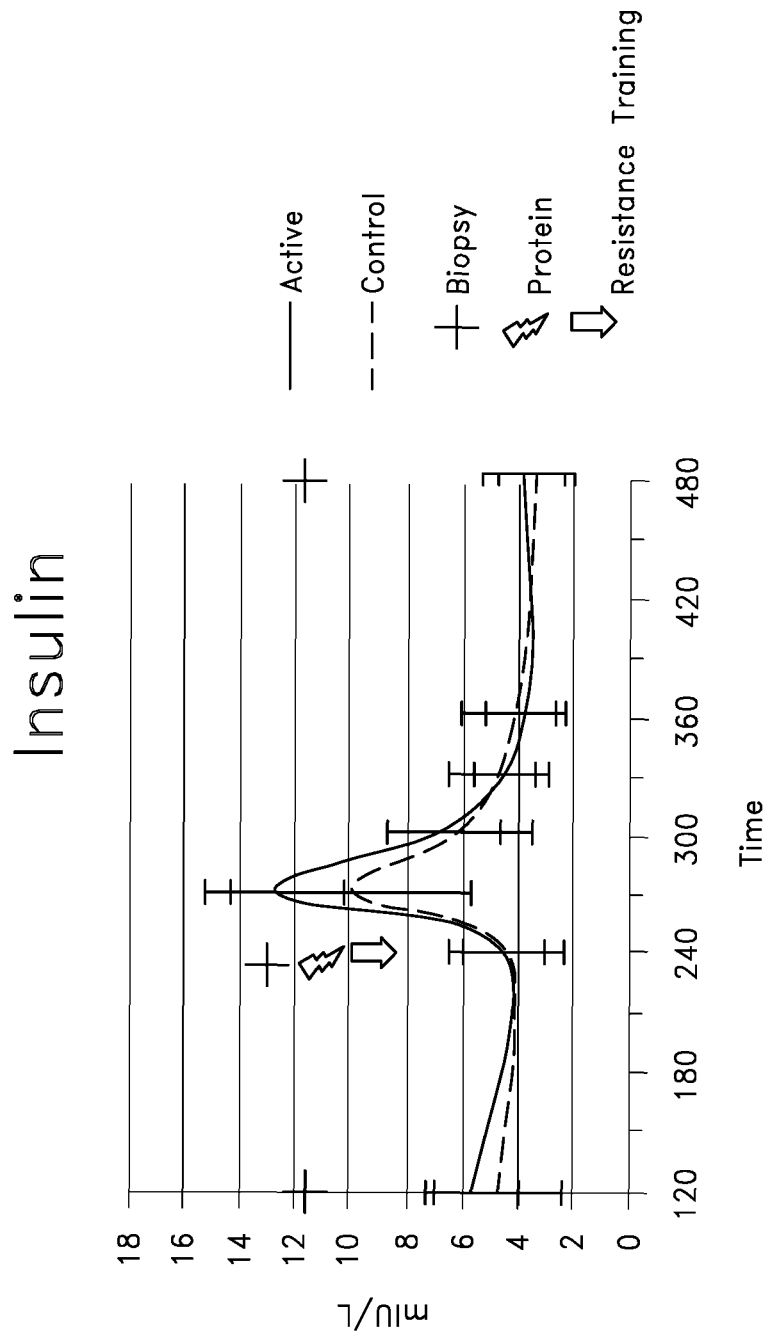
FIG. 3, FIG. 4, and FIG. 5 illustrate changes in mean±SD plasma insulin. Two-way ANOVA revealed a trend (P=0.09) for a difference between trials. Within-trial increases were statistically significant for only Trial A at all time points after 240 min (i.e. 270 min, 300 min, 330 min, 360 min, 390 min, and 480 min).
Figure 4:
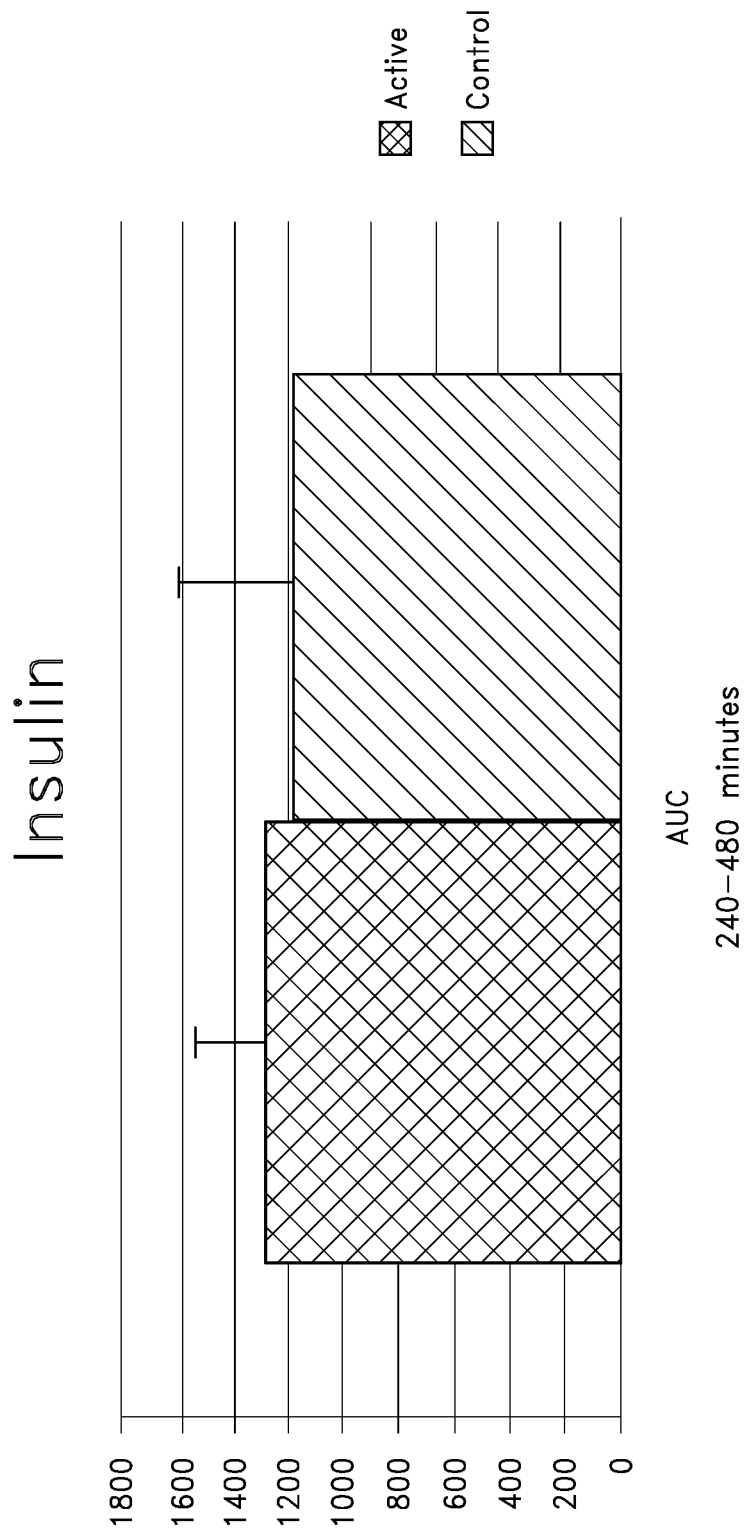
Figure 5:
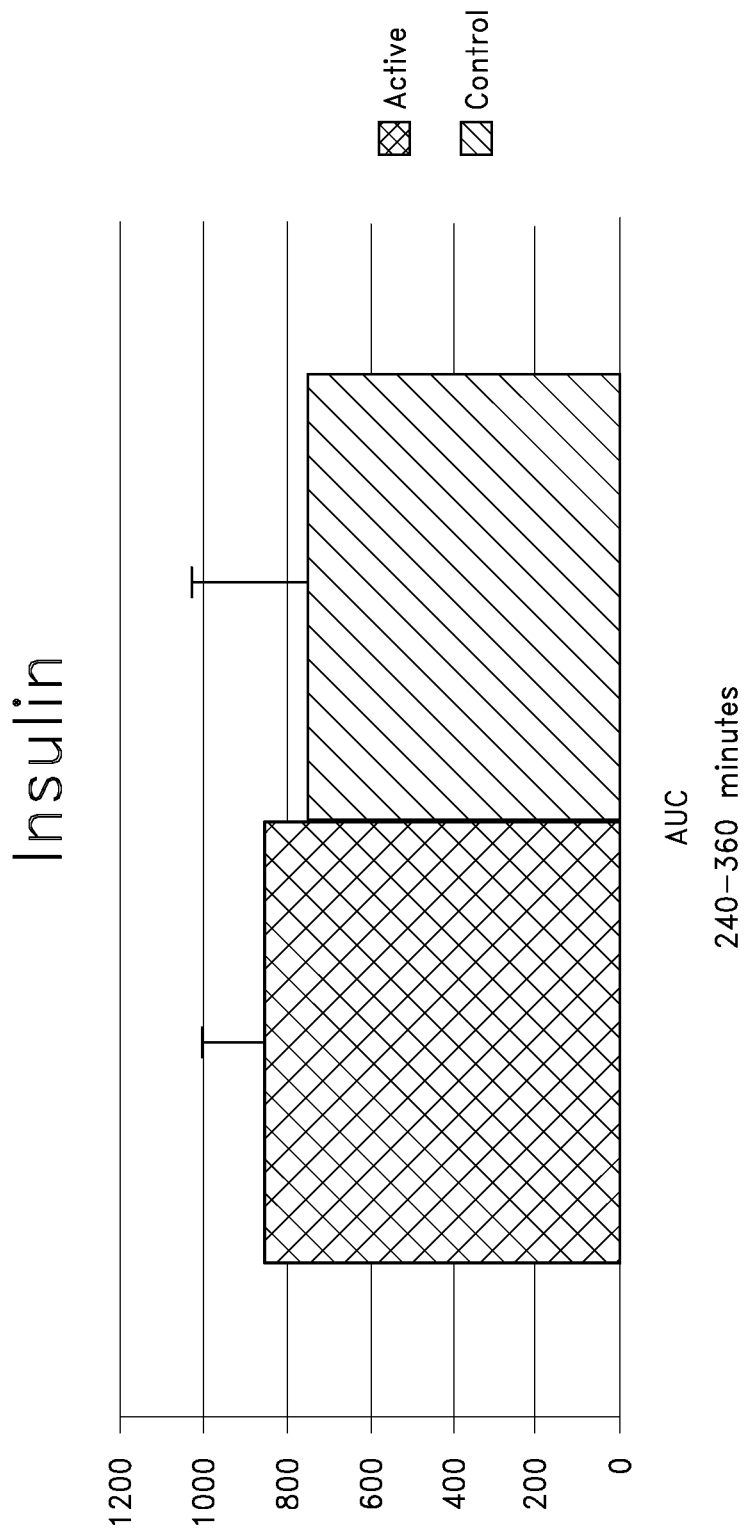
Figure 6:
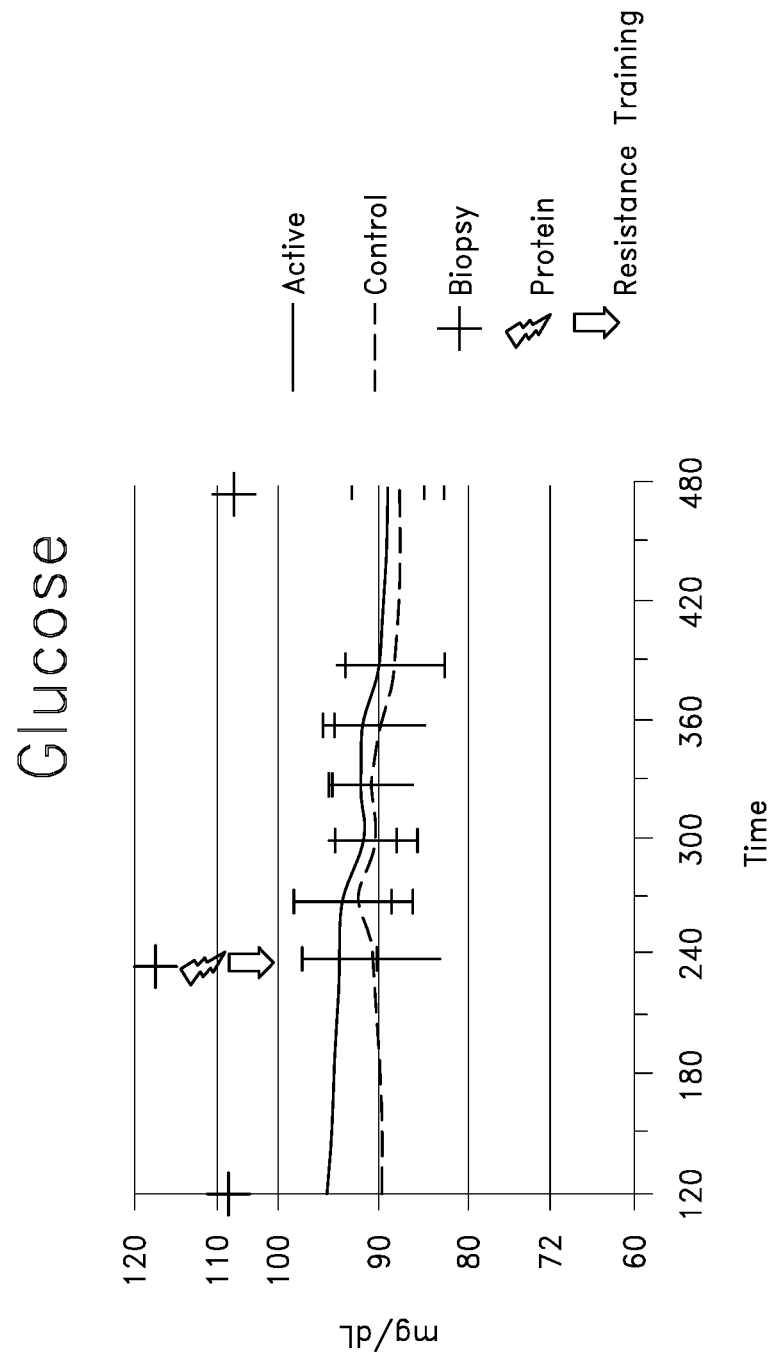
Figure 6A:
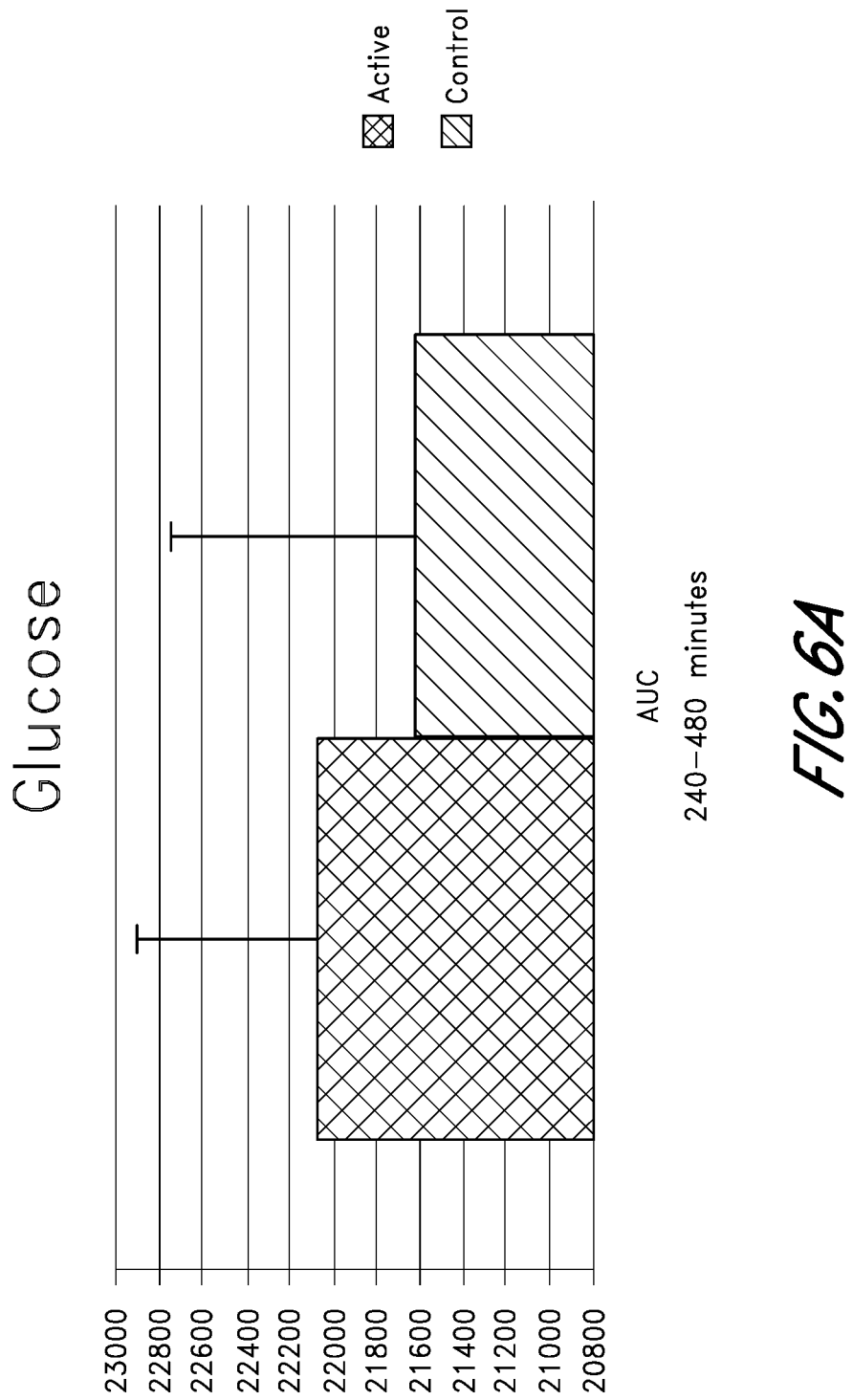
Figure 7:
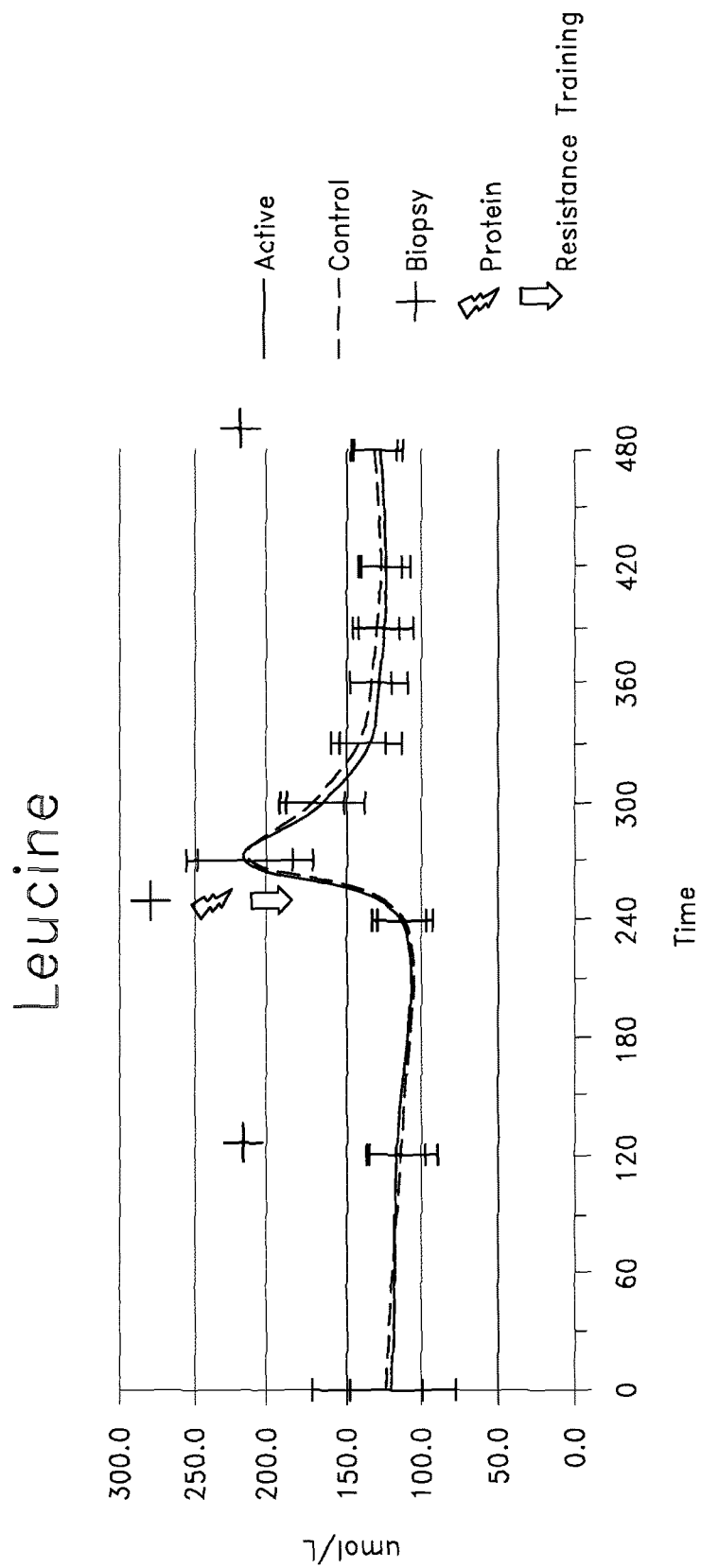
FIG. 7 illustrates peak increases in mean±SD plasma leucine occurred 30 minutes after the oral ingestion of whey protein+CrPic/CrHis+amylopectin (WCAP), (i.e. at 270 min) and were significantly different from baseline (P<0.001). However, no overall interaction was noted (P=0.22), and pair-wise differences were not statistically significant between trials at any time point.
Figure 8:
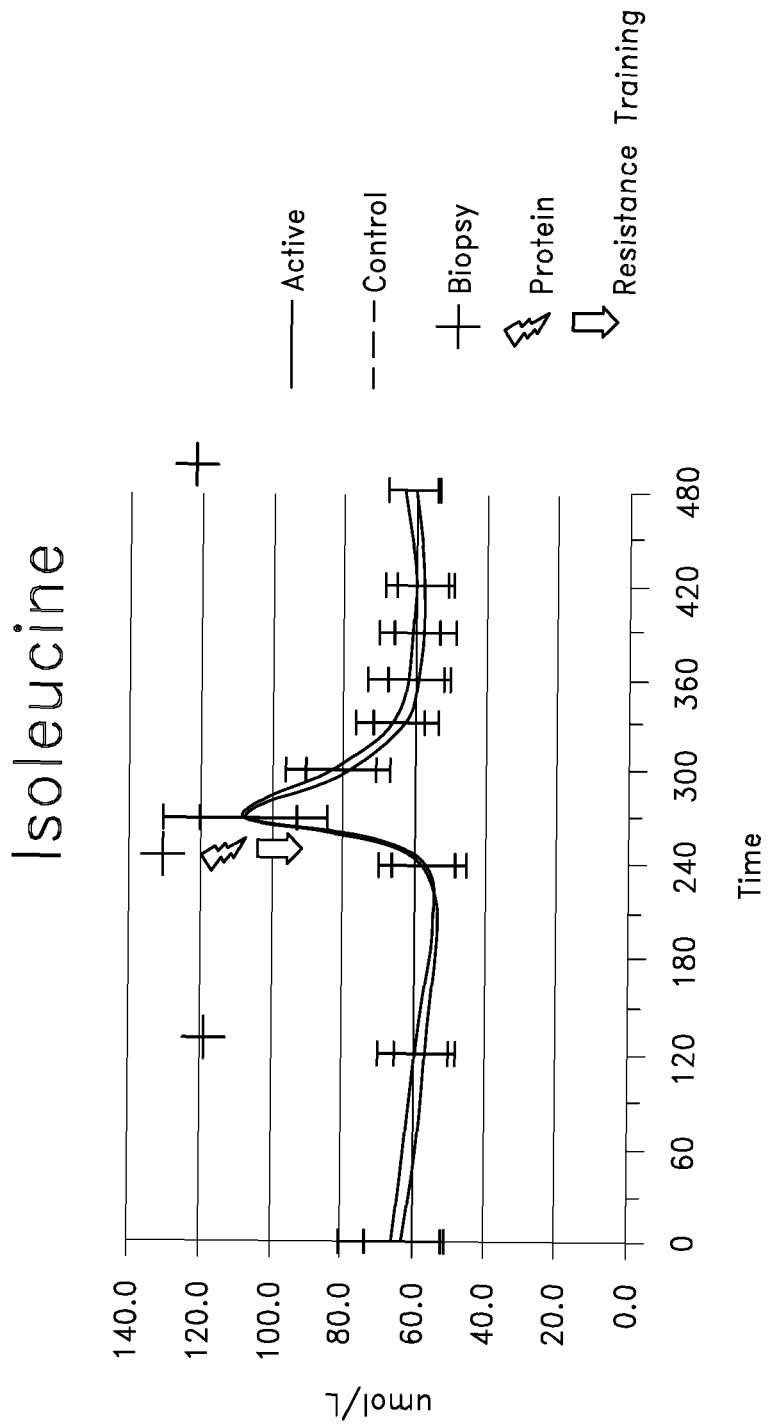
FIG. 8 illustrates peak increases in mean±SD plasma isoleucine occurred 30 minutes after the oral ingestion of WCAP, (i.e. at 270 min) and were significantly different from baseline (P<0.001). However, no overall interaction was noted (P=0.24), and pair-wise differences were not statistically significant between trials at any time point.
Figure 9:
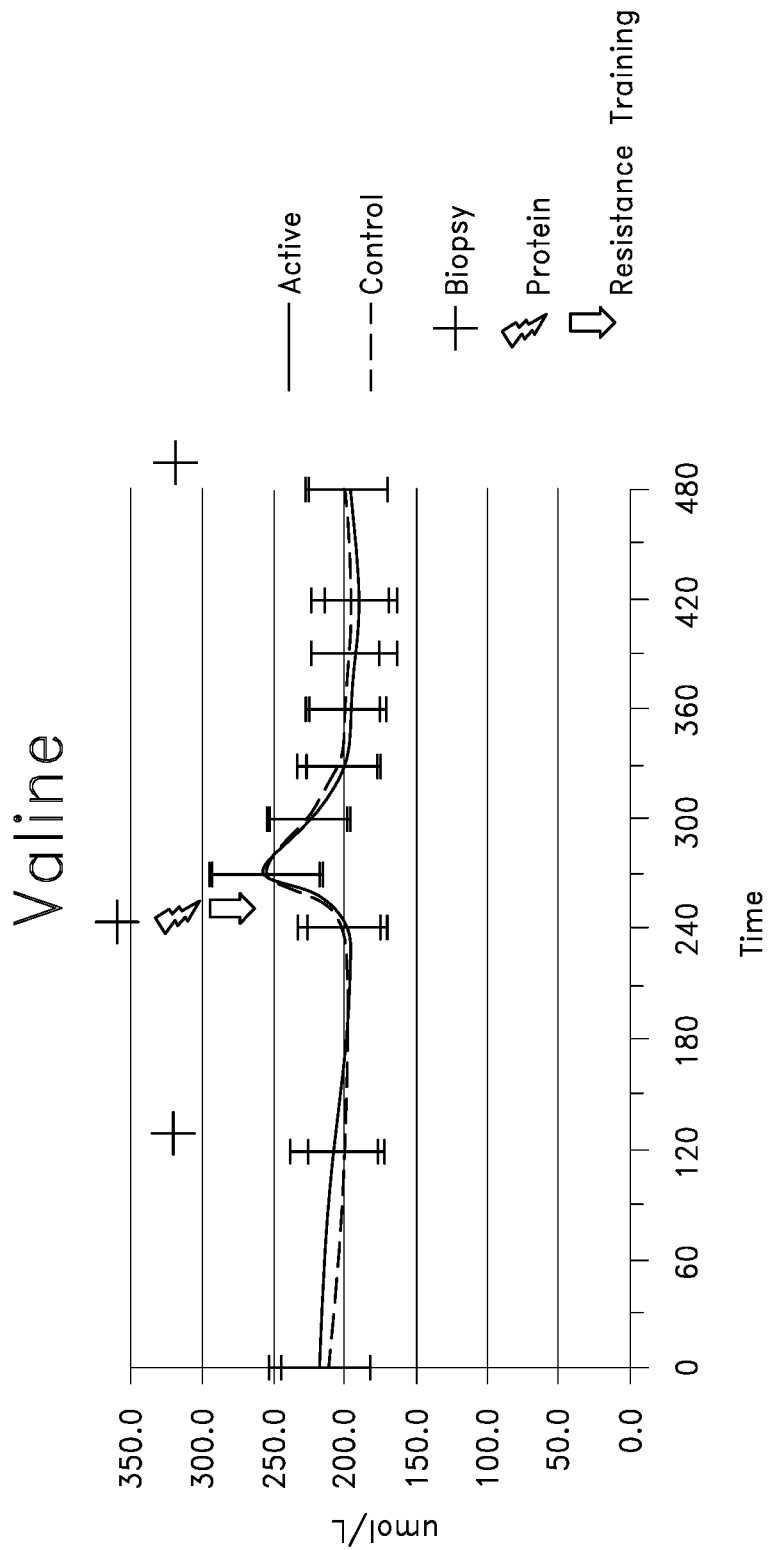
FIG. 9 illustrates peak increases in mean±SD plasma valine occurred 30 minutes after the oral ingestion of WCAP, (i.e. at 270 min) and were significantly different from baseline (P<0.02). However, no overall interaction was noted (P=0.66), and pair-wise differences were not statistically significant between trials at any time point.
Figure 10:
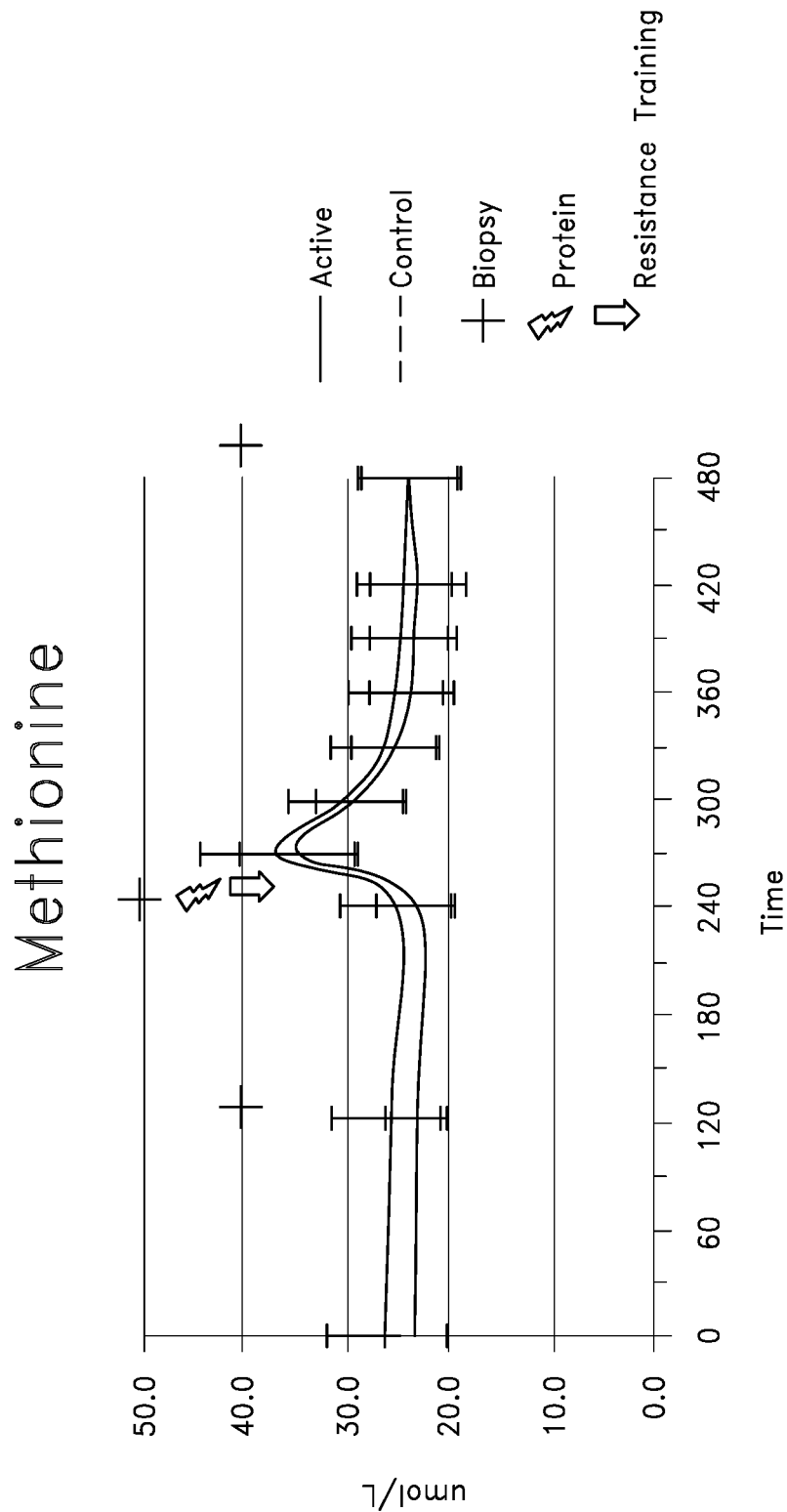
FIG. 10 illustrates peak increases in mean±SD plasma methionine occurred 30 minutes after the oral ingestion of WCAP, (i.e. at 270 min) and were significantly different from baseline (P<0.006). However, no overall interaction was noted (P=0.81), and pair-wise differences were not statistically significant between trials at any time point.
Figure 11:
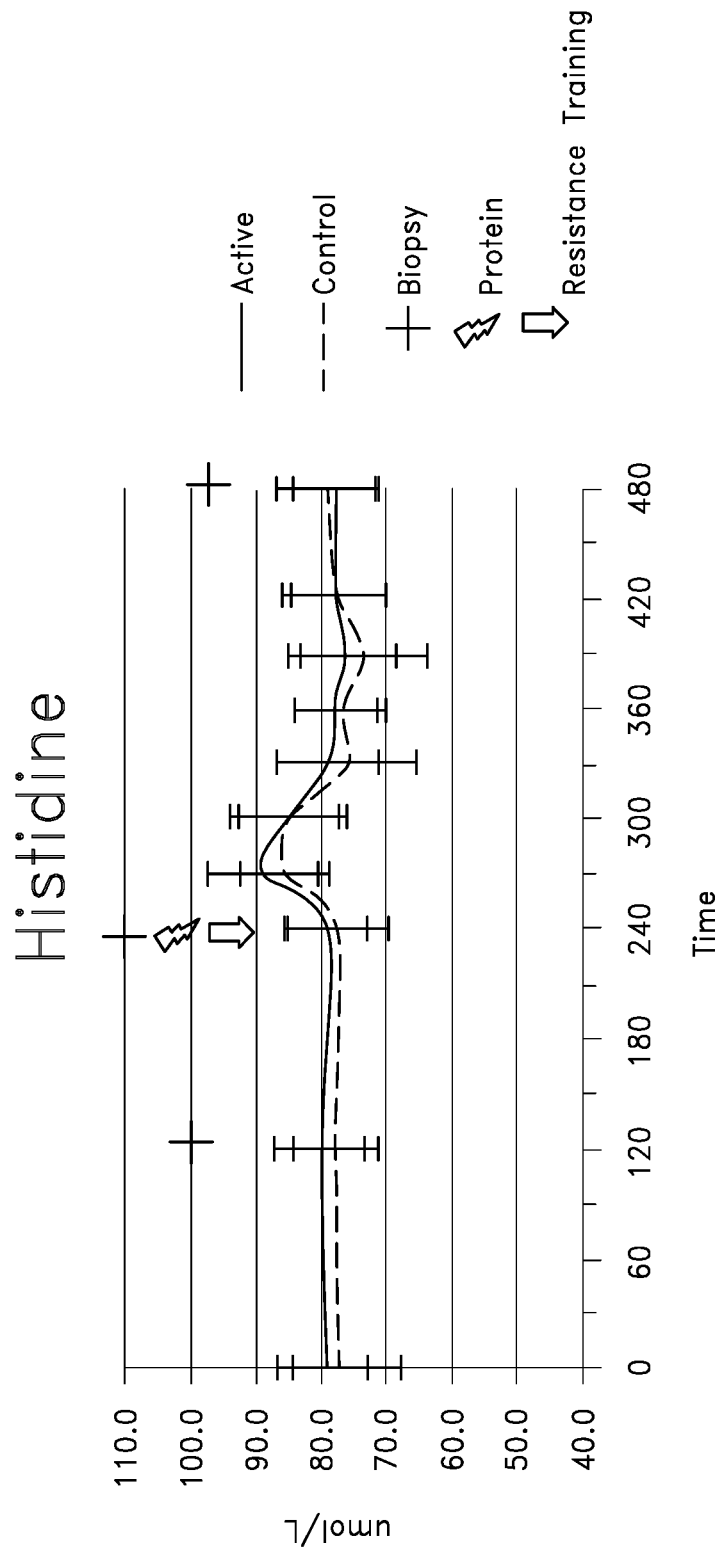
FIG. 11 illustrates peak increases in mean±SD plasma histidine occurred 30 minutes after the oral ingestion of WCAP, (i.e. at 270 min) and tended to be significantly different from baseline in Trial A only (P=0.06). However, no overall interaction was noted (P=0.58), and pair-wise differences were not statistically significant between trials at any time point.
Figure 12:
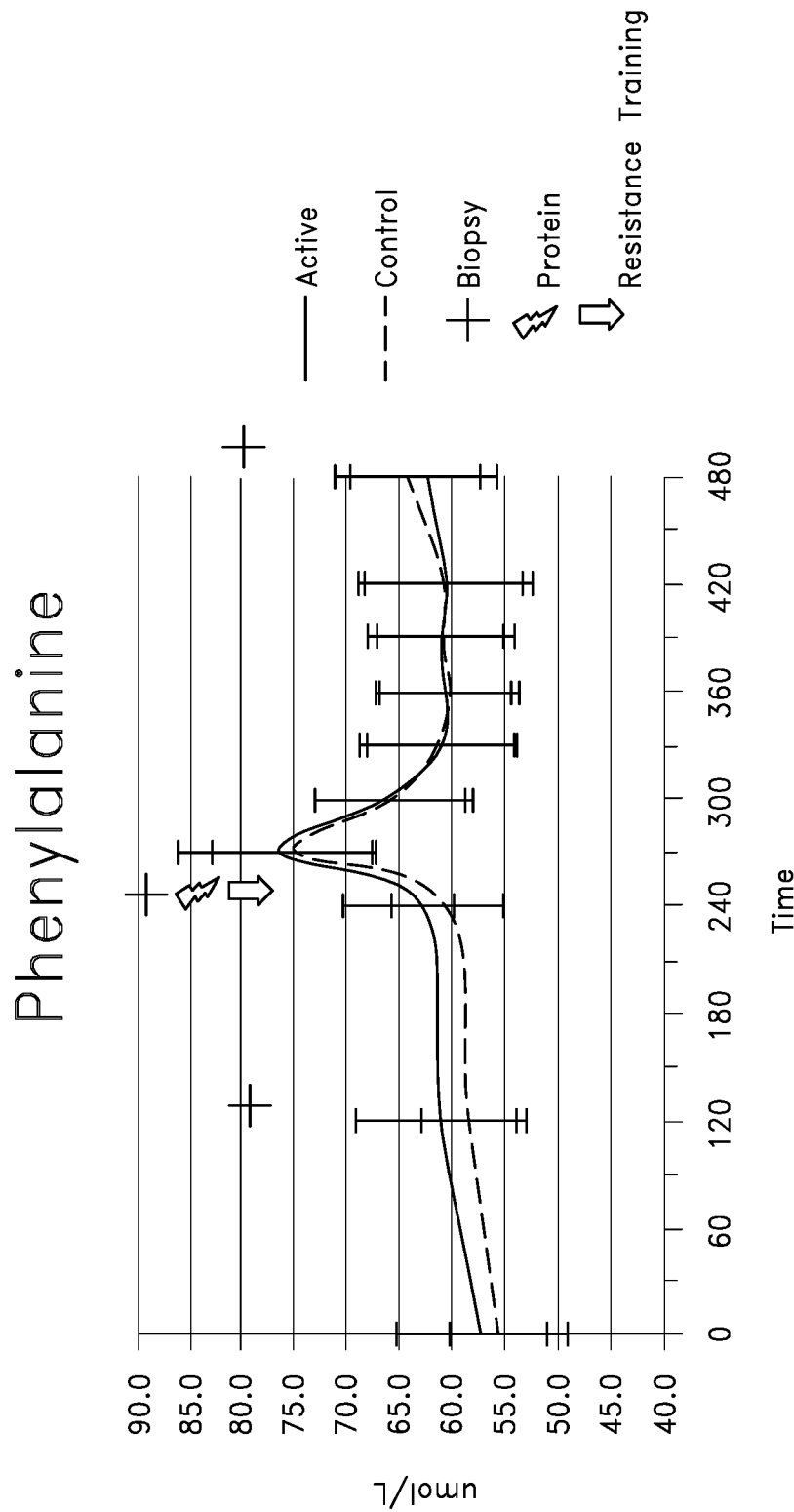
FIG. 12 illustrates peak increases in mean±SD plasma phenylalanine occurred 30 minutes after the oral ingestion of WCAP, (i.e. at 270 min) and were significantly different from baseline (P<0.001). Values at 240 min and 300 min were also significantly greater in both Trials (compared to their respective baseline). However, no overall interaction was noted (P=0.28), and pair-wise differences were not statistically significant between trials at any time point.
Figure 13:
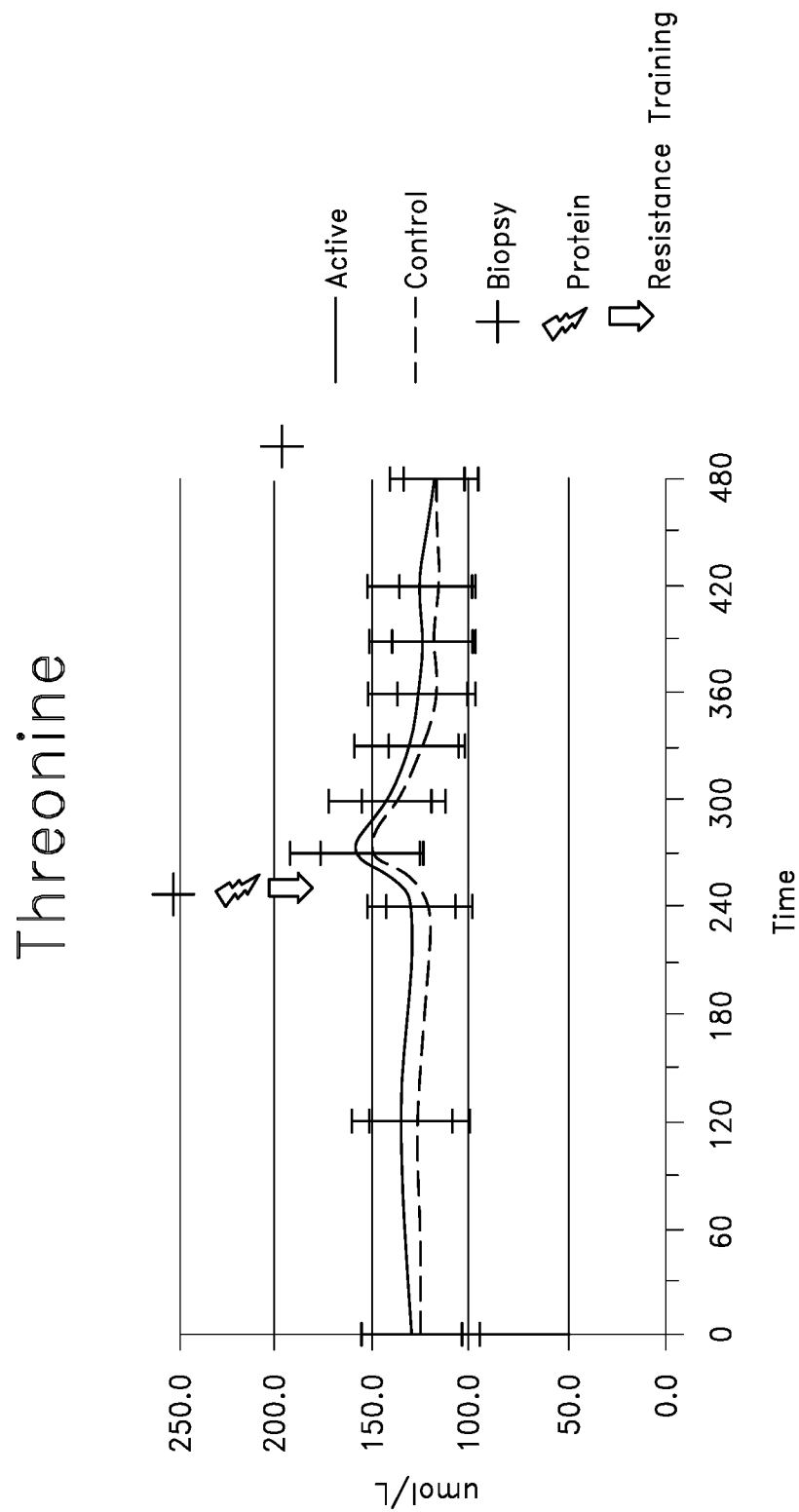
FIG. 13 illustrates peak increases in mean±SD plasma threonine occurred 30 minutes after the oral ingestion of WCAP, (i.e. at 270 min) and were significantly different from baseline (P<0.01) during Trial A only. However, no overall interaction was noted (P=0.62), and pair-wise differences were not statistically significant between trials at any time point.
Figure 14:
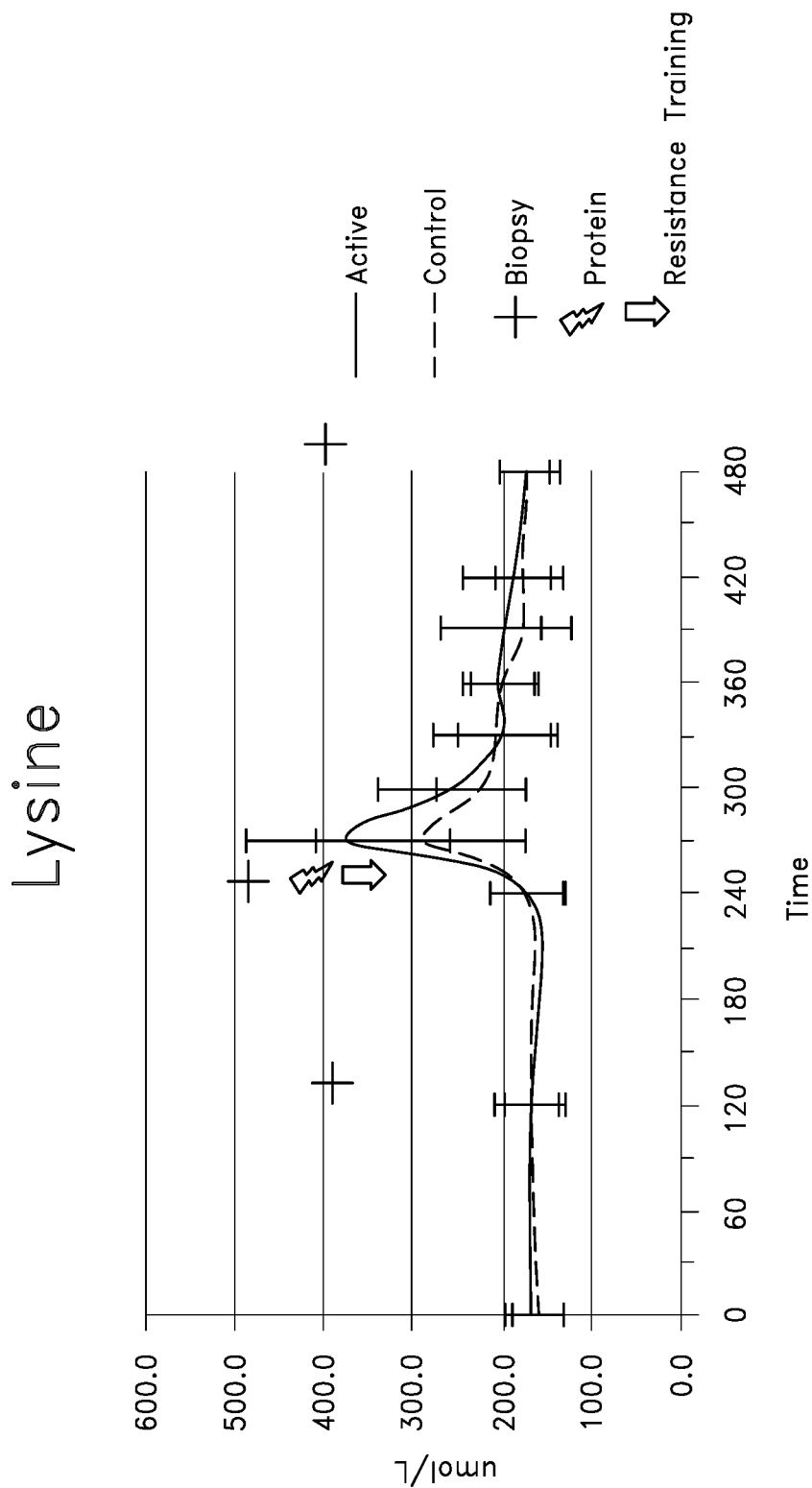
FIG. 14 illustrates peak increases in mean±SD plasma lysine occurred 30 minutes after the oral ingestion of WCAP, (i.e. at 270 min) and were significantly different from baseline (P<0.006). However, no overall interaction was noted (P=0.43), and pair-wise differences were not statistically significant between trials at any time point.
Figure 15:
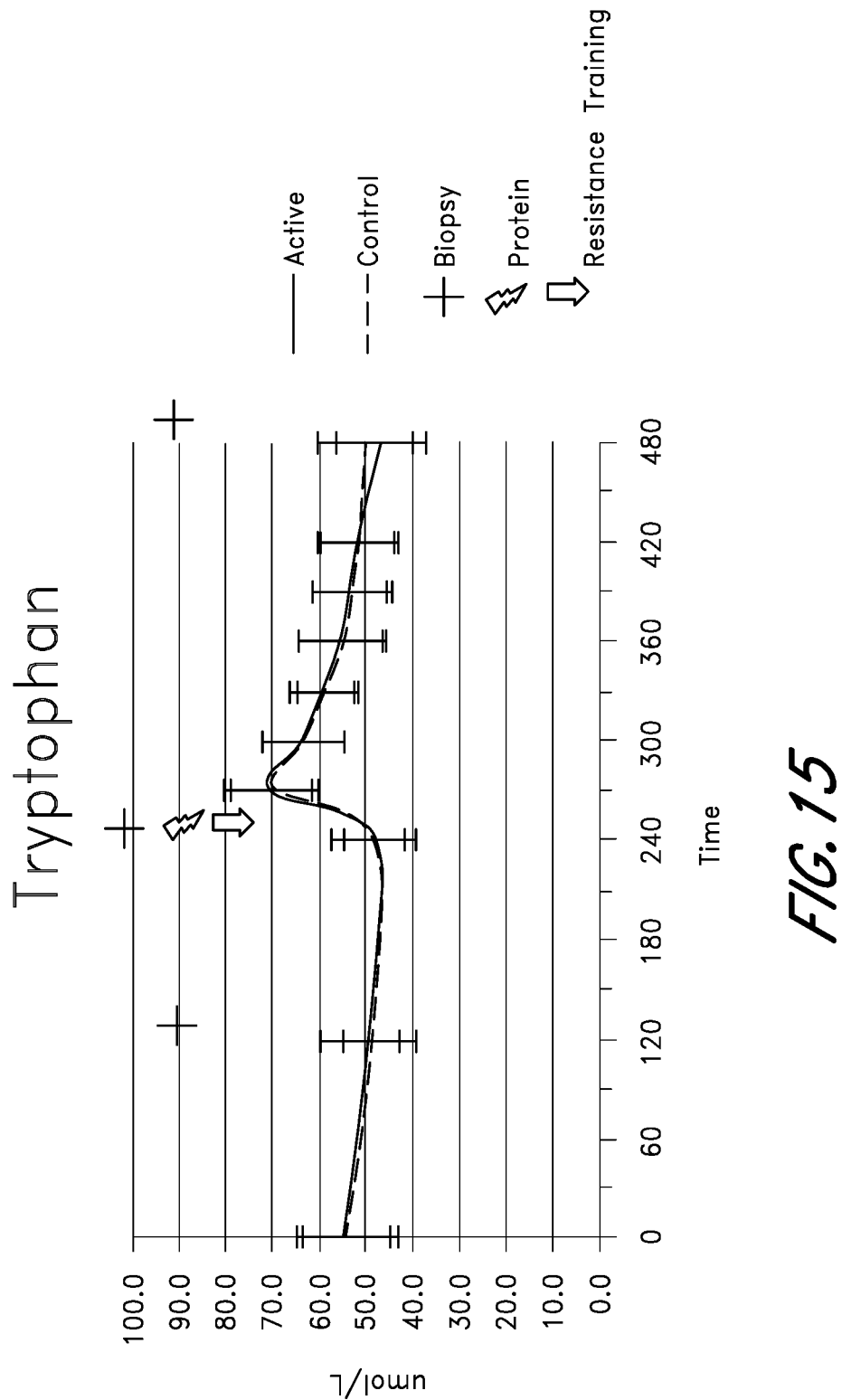
FIG. 15 illustrates peak increases in mean±SD plasma tryptophan occurred 30 minutes after the oral ingestion of WCAP, (i.e. at 270 min) and were significantly different from baseline (P<0.03). However, no overall interaction was noted (P=0.80), and pair-wise differences were not statistically significant between trials at any time point.
Figure 16:
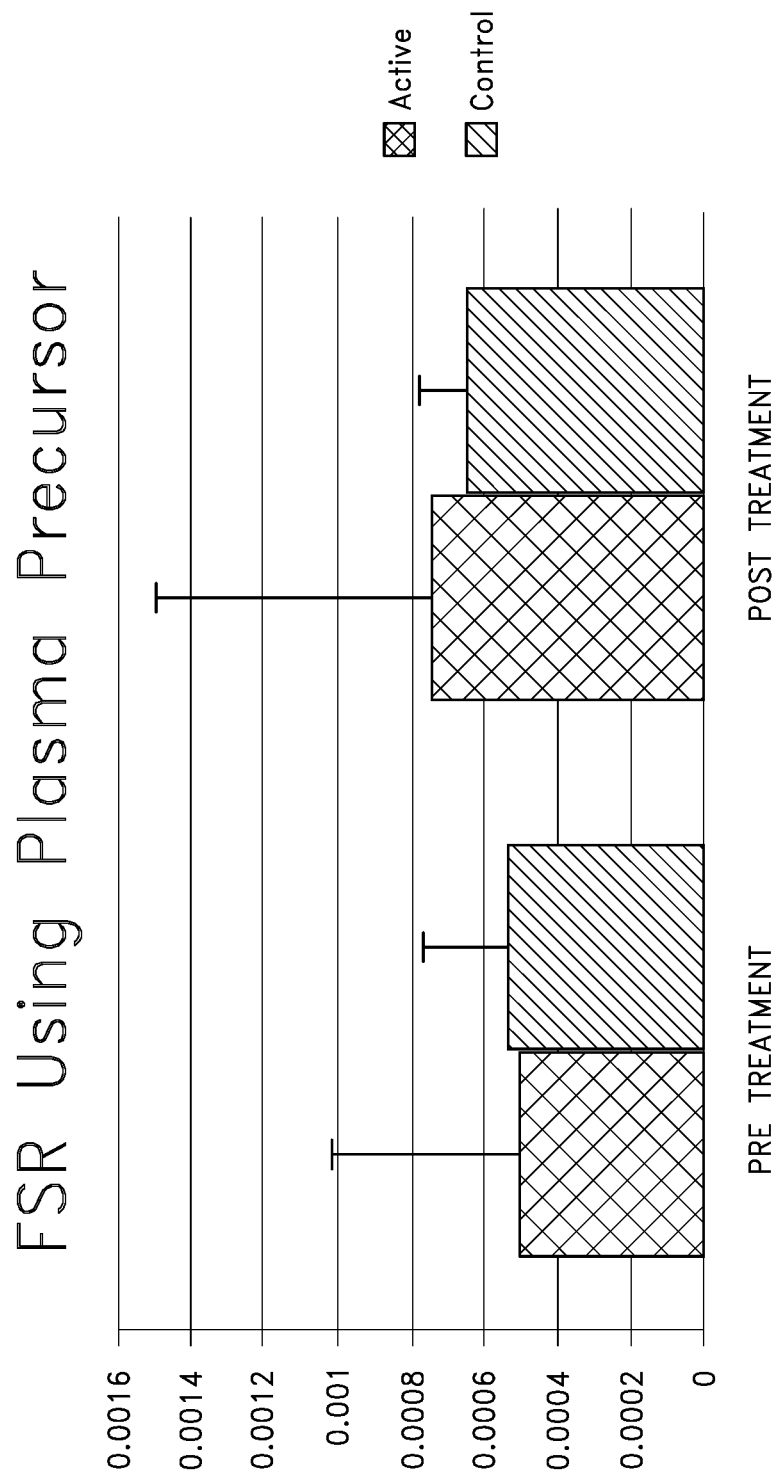
FIG. 16 illustrates mean±SD changes in muscle fractional protein synthesis rate (FSR) using plasma precursor enrichment. Three-way ANOVA (Trial×Gender×Time) was not significant, P=0.59. Two-way ANOVA was not significant (P=0.36); however, one-way ANOVA revealed a statistically significant (within-trial) increase during the Active trial only (P=0.001).
Figure 17:
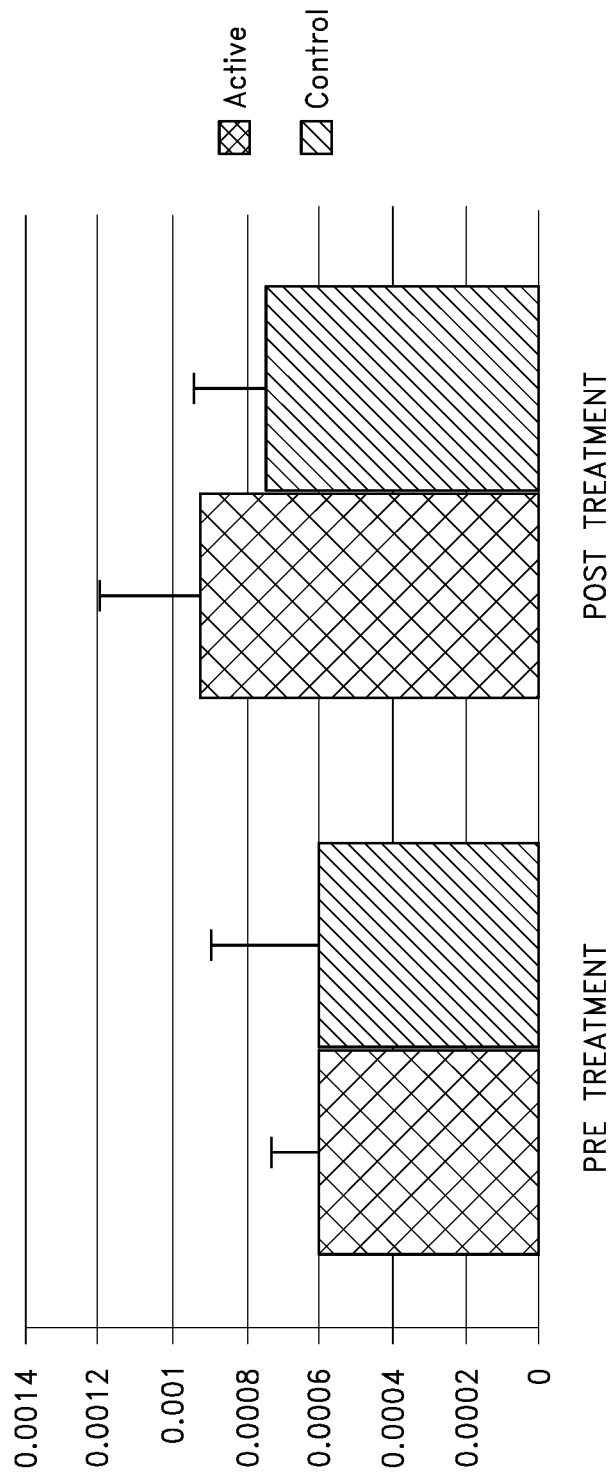

FIG. 17 illustrates mean±SD changes in FSR using intracellular precursor enrichment. Three-way ANOVA (Trial× Gender×Time) was not significant, P=0.37. Two-way ANOVA was not significant (P=0.30); however, one-way ANOVA revealed a statistically significant (within-trial) increase during the Active trial only (P=0.001).

Figure 18:
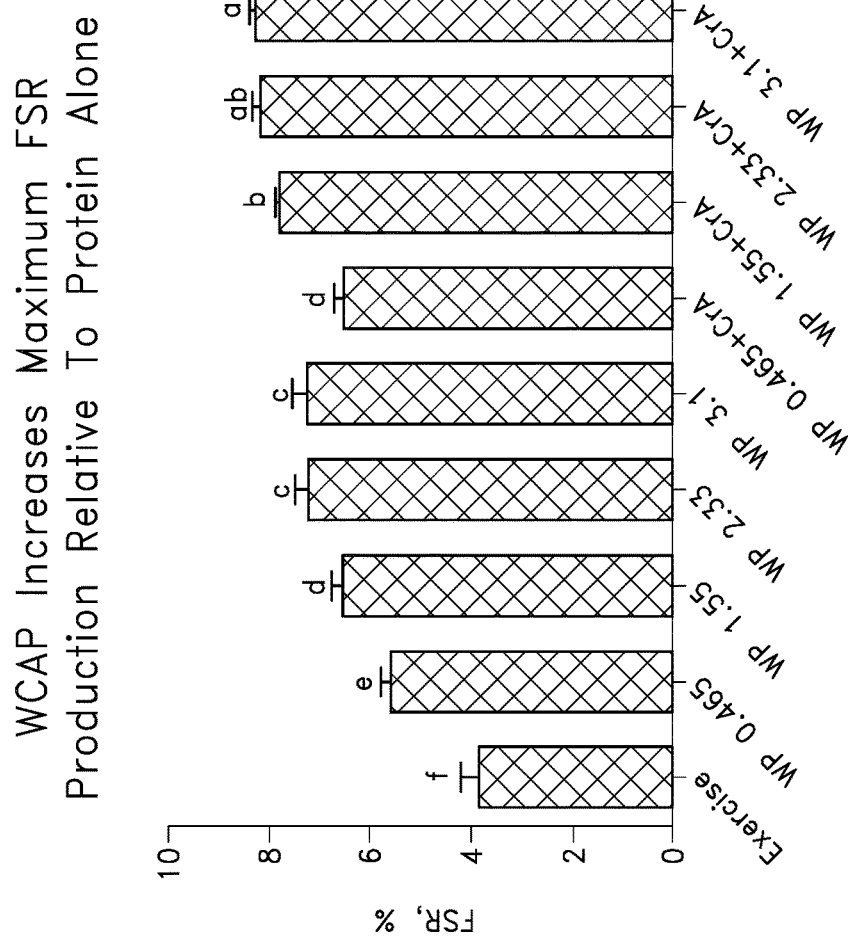

FIG. 18 illustrates that increasing doses of protein alone increased FSR up to a ceiling at 2.33 grams protein/kg. Administration of WCAP provided an unexpectedly significant increase in FSR even at protein levels over the maximum FSR achieved with protein alone, i.e., WCAP increases the protein ceiling relative to whey protein alone. The FSR of lower doses of WCAP also unexpectedly provided enhanced protein synthesis that were equivalent to FSR levels achieved with substantially higher doses of protein alone.

Figure 19:
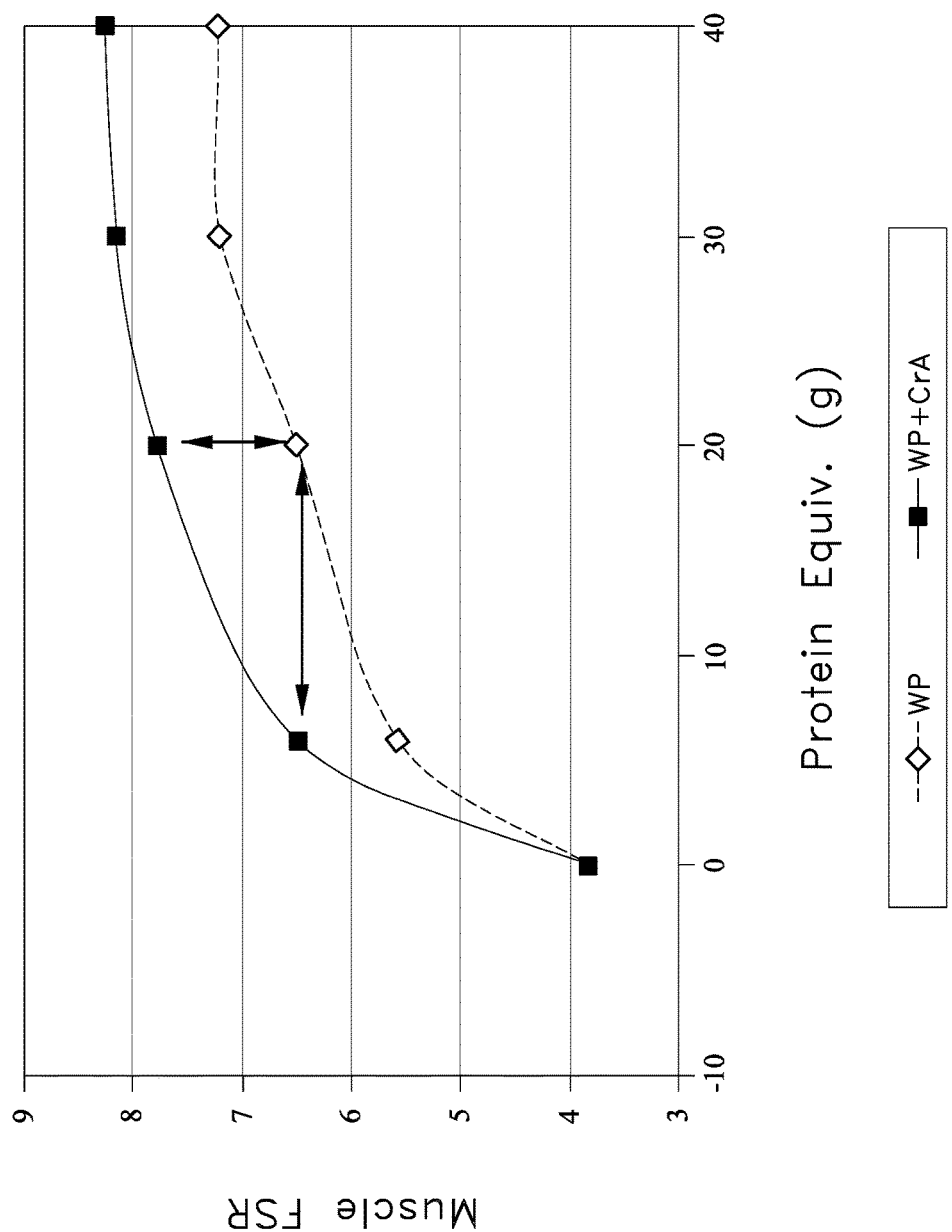

FIG. 19 illustrates that WCAP increases the maximum FSR levels compared to an equivalent dose of protein alone (vertical arrow). FIG. 19 also illustrates that low doses of WCAP provide equivalent FSR levels to much higher doses of protein alone (horizontal arrow).

DETAILED DESCRIPTION

Definitions

The terminology used in the description presented herein is not intended to be interpreted in any limited or restrictive manner, simply because it is being utilized in conjunction with a detailed description of certain specific embodiments described herein. Furthermore, embodiments described herein can include several novel features, no single one of which is solely responsible for its desirable attributes or which is essential to practicing the invention herein described.

Embodiments relate to the use of compositions comprising, consisting essentially of, or consisting of chromium and at least one starch. The chromium may be provided as chromium and histidine, a chromium histidinate complex, chromium trihistidinate, a chromium poly histidinate complex, or combinations thereof, including pharmaceutically acceptable salts, hydrates, solvates, or mixtures thereof in combination with a second slow-acting chromium complex for the treatment or prevention of cardiometabolic syndrome and related conditions, diseases, and disorders.

The term "treating" or "treatment" as used herein is a broad term, and is to be given its ordinary and customary meaning to a person of ordinary skill in the art (and is not to be limited to a special or customized meaning), and does not necessarily mean total cure. Any alleviation of any undesired signs or symptoms of the disease to any extent or the slowing down of the progress, or even prevention of the disease or condition can be considered treatment. As used herein, the term "providing" (a substance) as used herein is a broad term, and is to be given its ordinary and customary meaning to a person of ordinary skill in the art (and is not to be limited to a special or customized meaning), and refers without limitation to supplying, making available, or administering the substance. As used herein, the term "temporally proximate" (to an event) refers to a time about two hours before, to two hours after, the event, including during the event. As used herein, the term "resistance exercise" as used herein is a broad term, and is to be given its ordinary and customary meaning to a person of ordinary skill in the art (and is not to be limited to a special or customized meaning), and refers without limitation to any exercise that causes the muscles to contract against an external resistance, for example a weighted bar, or against body weight. As used herein, the term "subject" as used herein is a broad term, and is to be given its ordinary and customary meaning to a person of ordinary skill in the art (and is not to be limited to a special or customized meaning), and refers without limitation to animals, preferably mammals, and most preferably humans. The term "subject" may be used interchangeably with "patient" and with "person."

The compositions described herein can contain one or more chiral centers and/or double bonds and, therefore, exist as stereoisomers, such as double-bond isomers (i.e., geometric isomers), enantiomers, or diastereomers. The chemical structures depicted herein, and therefore the compositions of the embodiments, encompass all of the corresponding compounds' or compositions' enantiomers and stereoisomers, that is, both the stereomerically pure form (e.g., geometrically pure, enantiomerically pure, or diastereomerically pure) and enantiomeric and stereoisomeric mixtures.

As used herein, a composition that "substantially" comprises a compound means that the composition contains more than about 80% by weight, more preferably more than about 90% by weight, even more preferably more than about 95% by weight, and most preferably more than about 97% by weight of the compound. As used herein, a composition that "substantially" comprises a chromium complex refers to a composition that contains more than or equal to 7.0% of trivalent or dietary chromium. Preferably, a certificate of analysis for the compositions indicate that the compositions are negative for microbial growth, yeast and mold should be present in less than 300 cells/g and the toxic metals should be less than 1 ppm.

In some embodiments, the compositions are in the form of pharmaceutically effective salts. The phrase "pharmaceutically acceptable salt(s)," as used herein includes, but is not limited to, salts of acidic or basic groups that may be present in the compositions. Compounds that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2- hydroxy-3-naphthoate)) salts. Compounds present in the compositions that include an amino moiety also can form pharmaceutically acceptable salts with various amino acids, in addition to the acids mentioned above. Compounds present in the compositions that are acidic in nature are capable of forming base salts with various pharmacologically acceptable cations. Non limiting examples of such salts include alkali metal or alkaline earth metal salts and, particularly, calcium, magnesium, sodium lithium, zinc, potassium, silicon, phosphorus and iron salts.

As used herein, the term "hydrate" means a compound or a salt thereof, that further includes a stoichiometric or non-stoichiometric amount of water bound by non-covalent intermolecular forces. The term hydrate includes solvates, which are stoichiometric or non-stoichiometric amounts of a solvent bound by non-covalent intermolecular forces. Preferred solvents are volatile, non-toxic, and/or acceptable for administration to humans in trace amounts.

The amount of a compound of the embodiments that will be effective in the treatment of a particular disorder or condition will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each circumstances. However, suitable dosage ranges for oral administration are generally about 0.001 milligram to 5000 milligrams of a total chromium complex per kilogram body weight. In preferred embodiments, the oral dose is 0.01 milligram total chromium complex to 1000 milligrams per kilogram body weight, more preferably 0.1 milligram to 100 milligrams per kilogram body weight, more preferably 0.5 milligram to 25 milligrams per kilogram body weight, and yet more preferably 1 milligram to 10 milligrams per kilogram body weight. The dosage amounts described herein refer to total amounts administered; that is, if more than one chromium complex or more than one composition is administered, the preferred dosages correspond to the total amount of the compositions administered. Oral compositions preferably contain 10% to 95% active ingredient.

The compositions can preferably be formulated with other active ingredients as a slow-acting agent or long acting agent in addition to drugs or alone before meals and/or after meals. Effective doses may be extrapolated from dose-response curves derived from in vitro or animal model test systems. Such animal models and systems are well known in the art.

In accordance with the methods, the amount of chromium provided by the compositions that comprise at least 50 µg per dose, for example at least 60 µg, at least 70 µg, at least 80 µg, at least 90 µg, at least 100 µg, at least 125 µg, at least 150 µg, at least 200 µg, at least 250 µg, at least 300 µg, at least 350 µg, at least 400 µg, at least 450 µg, at least 500 µg, at least 550 µg, at least 600 µg, at least 650 µg, at least 700 µg, at least 750 µg, at least 800 µg, at least 850 µg, at least 900 µg, at least 950 µg, at least 1,000 µg, at least 1500 µg, at least 2,000 µg, at least 2500 µg, at least 3000 µg, at least 3500 µg, at least 4000 µg, at least 4500 µg or at least 5000 µg chromium per dose. In some aspects, the amount of chromium may be formulated to provide a certain amount of bioavailable chromium. For example, the compositions may provide at least 1-2,000 µg of bioavailable chromium per day.

In some aspects, chromium is provided in the form of a fast-acting chromium complex and a slow-acting chromium complex. The fast-acting complex may be absorbed more quickly than the slow-acting chromium complex. For example, in some embodiments, a lipophilic chromium complex or slow-acting chromium complex can be chromium picolinate or chromium tripicolinate, and the hydrophilic chromium complex or fast-acting chromium complex can be any one of chromium acetate, chromium chloride, chromium histidinate, and chromium nicotinate, or any combination thereof. In some embodiments, the hydrophilic chromium complex or fast-acting chromium complex is chromium histidinate. In some embodiments, a slow-acting or lipophilic chromium complex is chromium picolinate. The fast-acting and the slow-acting chromium complexes can be provided to a subject such that the ratio of chromium in the form of a "fast-acting" chromium complex to the chromium in the form of a "slow-acting" chromium complex is anywhere from 10:1 to 1:10, e.g., 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, or any fraction in between. In some embodiments, the ratio of chromium provided in the form of a fast-acting chromium complex to the slow-acting chromium complex is 1:1.

By way of example, the level of chromium used for supplementation in order to inhibit the onset of insulin resistance is at least about 50 µg/day. Chromium picolinate and chromium chloride have been administered to rats at levels several thousand times the upper limit of the estimated safe and adequate daily dietary intake (ESADDI) for chromium for humans (based on body weight) without toxic effects. R. Anderson et al., Lack of Toxicity of Chromium Chloride and Picolinate, 16 J. Am. Coll. Nutr. 273-279 (1997). While the level of chromium, in the form of fast-acting and slow-acting chromium complexes, used for supplementation may be within several thousand times the upper limit of the ESADDI, preferably, the total amount of chromium provided by the fast-acting and slow-acting complexes is between about 50 and 2,000 µg/day. More preferably, the amount of total chromium provided by the fast-acting and slow-acting complexes is between about 100 and 2,000 µg/day. Most preferably, the amount of total chromium is between about 400 and 1,000 µg/day. In a particularly preferred embodiment, the amount of total chromium is between about 600 and 1,000 µg/day. These doses are based on a 70 kg adult human, and that the dose can be applied on a per-kilogram basis to humans or animals of different weights.

Advantageously, an individual is administered a pharmaceutically effective dose of a hydrophilic chromium complex such as chromium histidinate in combination with at least one other lipophilic chromium complex, such as chromium picolinate. In some embodiments, a composition the fast-acting and a slow-acting chromium complexes are administered substantially simultaneously. In an alternative embodiment, the fast-acting, hydrophilic and slow-acting, lipophilic chromium complexes are provided to the subject sequentially in either order. If administered separately, the fast-acting and slow-acting chromium complex should be given in a temporally proximate manner, e.g., within a twenty-four hour period. More particularly, a fast-acting and a slow-acting chromium complex can be given within one hour of each other. One of skill in the art will appreciate that other components may be added separately or incorporated into a single formulation to enhance the effects of chromium.

In some embodiments, the compositions can be provided prior to or concomitantly with an insulin resistance-inducing food. Insulin resistance-inducing foods generally have high glycemic indexes, e.g., over 50. In other embodiments, the compositions are provided after the insulin resistance inducing food. In embodiments wherein the compositions and the insulin resistance-inducing foods are not provided concomitantly, the composition and the food are preferably provided in a temporally proximate manner, e.g., within twenty four hours, and more preferably within one hour.

In some embodiments, the compositions can be provided prior to or concomitantly with a high-protein meal or protein supplement. In some embodiments, the compositions can be provided once daily, up to six times daily. In some embodiments, the compositions can be provided prior to or concomitantly with each meal during the day. In some embodiments, the compositions can be provided prior to or concomitantly with each snack during the day. In some embodiments, the compositions can be provided prior to or concomitantly with each meal and each snack during the day.

In some embodiments, the compositions can be provided prior to or concomitantly to aerobic training. In some embodiments, the compositions can be provided prior to or concomitantly to anaerobic training. In some embodiments, the compositions can be provided concomitantly with other exercise supplements, including, but not limited to caffeine, creatine, creatine hydrochloride, creatine monohydrate, taurine, guarana, vitamin C, vitamin $B_1$, vitamin $B_2$, vitamin $B_3$, vitamin $B_5$, vitamin $B_6$, vitamin $B_7$, vitamin $B_9$, and vitamin $B_{12}$, or any combination of the foregoing.

In some embodiments, uncomplexed chelating agents are advantageously included in the compositions to facilitate absorption of other ingested chromium as well as other metals including, but not limited to, copper, iron, magnesium, manganese, and zinc. Suitable chelating agents include histidine, any essential amino D or L amino acids, tri amino acid formulae including but not limited to, triphenylalanine, trihistidine, triarginine, picolinic acid, nicotinic acid, or both picolinic acid and nicotinic acid. Thus, the compositions of the embodiments are readily absorbable forms of chromium complex which also facilitate absorption of other essential metals in the human diet. In some embodiments, certain chelating agents may be added to facilitate absorption of the chromium complex, or combination of chromium complexes in the compositions. Chelating agents such as histidine, picolinic acid and nicotinic acid are available from many commercial sources, including Sigma-Aldrich (St. Louis, Mo.) (picolinic acid; catalog No. P5503; nicotinic acid; catalog No. PN4126). Preferably, the ratio of either the fast-acting, or slow-acting, or the combination of the fast-acting and slow-acting chromium complex to the chelating agent from about 10:1 to about 1:10 (w/w), more preferably from about 5:1 to about 1:5 (w/w). Alternatively, the molar ratio of chromium complex to the uncomplexed chelating agent is preferably 1:1, and may be from about 5:1 to about 1:10. The chelating agents with D or L amino acid and or with tri or mono and di forms of chromium complex with tri amino acid or one or more amino acids but not limited to chromium triphenylanine, chromium trihistidine, chromium polyphenylanine, chromium poly hisitidine, chromium polynicotinate, chromium diphenylananine, chromium dipicolinic acid, chromium dihisitidine etc. More than one chelating agent, e.g., both nicotinic and picolinic acid can be included in the compositions, or administered to subject in the methods described herein.

Certain embodiments also include an amino acid source. Exemplary amino acid sources include, but are not limited to whey protein, casein protein, egg protein, pea protein, rice protein, soy protein, beef protein, hemp protein, vegetable protein and combinations of any of the foregoing. The amino acid source may optionally by hydrolyzed. The protein source is optionally an isolate of one or more of the protein sources described above. The source of protein may be administered at the same time as the chromium and/or starch or at a different time. The relative amounts of amino acids to starch to chromium may vary. In some embodiments, the amino acid source comprises about 1 gram of protein to about 30 grams of protein, or any value in between. In some embodiments, the amino acid source comprises about 1 to about 30 grams, about 2 to about 25 grams, about 3 to about 20 grams, about 4 to about 15 grams, about 5 to about 10 grams of protein, or any amount in between.

Certain embodiments also include one or more starches or saccharides. Exemplary saccharides include, but are not limited to glucose, sucrose, fructose, maltose, maltodextrin, dextrin, amylose, pectin, and amylopectin. The compositions may include at least 1,000 mg per day, for example at least 50 mg, at least 70 mg, at least 80 mg, at least 90 mg, at least 100 mg, at least 125 mg, at least 150 mg, at least 200 mg, at least 250 mg, at least 300 mg, at least 350 mg, at least 400 mg, at least 450 mg, at least 500 mg, at least 550 mg, at least 600 mg, at least 650 mg, at least 700 mg, at least 750 mg, at least 800 mg, at least 850 mg, at least 900 mg, at least 950 mg, at least 1,000 mg, at least 1500 mg, at least 2,000 mg, at least 2500 mg, at least 3000 mg, at least 3500 mg, at least 4000 mg, at least 4500 mg or at least 5000 mg of amylopectin per dose. In some aspects, the amount of amylopectin may be formulated to provide a certain amount of bioavailable amylopectin. For example, the compositions may provide at least 1-5,000 mg of bioavailable amylopectin per day. The chromium and the amylopectin can be provided to a subject such that the ratio of chromium to the amylopectin is anywhere from 1:2,000 or any fraction in between.

In general, the compositions may be formulated such that the starch and the chromium are delivered at the same time or at substantially the same time. In some aspects, the starch and chromium may form a chromium-starch complex. That is to say, one or more starches and chromium ions may be associated with each other and administered in such a manner. For example, the composition may include one or more chromium/amylopectin complexes and/or conformations.

The compositions comprising, for example, chromium and amylopectin may be dosed a plurality of times per day. For example, the composition may be administered once per day or twice per day or three times per day or four times per day or five times per day or six times per day. The composition may be administered before or after a meal or a set time interval before or after a meal. The composition may be administered immediately before or after immediately exercise. The composition may also be administered at a set time interval before or after exercise.

The administration of the compositions can be by any of the methods of administration described below or by delivery methods known by one of skill in the art. The compositions may be administered orally, through parenteral nutrition, e.g., feeding tube or intravenously, and through other known means. Chromium histidinate in combination with other chromium complexes or essential nutrients but not limited to fatty acids, carbohydrates, minerals and vitamins etc. is a particularly preferred source fast-acting chromium complex due to its high level of bioavailability, but other fast-acting, hydrophilic chromium complex can also be used.

Some embodiments provide at least 50 mcg bioavailable chromium. Some embodiments provide at least 100 mcg bioavailable chromium. Some embodiments provide at least 150 mcg bioavailable chromium. Some embodiments provide at least 250 mcg bioavailable chromium. Some embodiments provide at least 50 mcg bioavailable chromium in about 30 minutes. Some embodiments provide at least 100 mcg bioavailable chromium in about 1 hour. Some embodiments provide at least 200 mcg bioavailable chromium in about 2 hours. Some embodiments provide at least 200 mcg bioavailable chromium in about 4 hours.

Some embodiments provide at least 500 mcg bioavailable chromium. Some embodiments provide at least 750 mcg bioavailable chromium. Some embodiments provide at least 1,000 mcg bioavailable chromium. Some embodiments provide at least 1,250 mcg bioavailable chromium. Some embodiments provide at least 500 mcg bioavailable chromium in about 30 minutes. Some embodiments provide at least 750 mcg bioavailable chromium in about 1 hour. Some embodiments provide at least 1,000 mcg bioavailable chromium in about 2 hours. Some embodiments provide at least 1,000 mcg bioavailable chromium in about 4 hours.

Some embodiments provide an increased amount of bioavailable starch relative to starch alone. Some embodiments provide an increased amount of bioavailable protein relative to protein alone. Some embodiments provide an increased amount of bioavailable protein and starch relative to protein and starch alone. In some embodiments, the bioavailability is increased by at least about 10%, at least about 20%, at least about 30%, at least about 40%, at least about 50%, at least about 60%, at least about 70%, at least about 80%, at least about 90%, at least about 95%, or at least about 99%.

For oral administration, the compositions can be provided as a tablet, aqueous or oil suspension, dispersible powder or granule, emulsion, hard or soft capsule, syrup, elixir, or beverage. Compositions intended for oral use can be prepared according to any method known in the art for the manufacture of pharmaceutically acceptable compositions and such compositions may contain one or more of the following agents: sweeteners, flavoring agents, coloring agents and preservatives. The sweetening and flavoring agents will increase the palatability of the preparation. Tablets containing chromium complexes in admixture with non-toxic pharmaceutically acceptable excipients suitable for tablet manufacture are acceptable. Pharmaceutically acceptable vehicles such as excipients are compatible with the other ingredients of the formulation (as well as non-injurious to the patient). Such excipients include inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc. Tablets can be uncoated or can be coated by known techniques to delay disintegration and absorption in the gastrointestinal tract and thereby provide a sustained action over a longer period of time. For example, a time delay material such as glyceryl monostearate or glyceryl distearate alone or with a wax can be employed.

Formulations for oral use can also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil. Aqueous suspensions can contain the chromium complex of the embodiments in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions can be formulated by suspending the active ingredient in a vegetable oil, such as arachis oil, olive oil, sesame oil or coconut oil, or in a mineral oil such as liquid paraffin. The oil suspension can contain a thickening agent, such as beeswax, hard paraffin or cetyl alcohol. Sweetening agents, such as those set forth above, and flavoring agents can be added to provide a palatable oral preparation. These compositions can be preserved by an added antioxidant such as ascorbic acid. Dispersible powders and granules of the embodiments suitable for preparation of an aqueous suspension by the addition of water provide the active ingredient in admixture with a dispersing or wetting agent, a suspending agent, and one or more preservatives. Additional excipients, for example sweetening, flavoring and coloring agents, can also be present.

Syrups and elixirs can be formulated with sweetening agents, such as glycerol, sorbitol or sucrose. Such formulations can also contain a demulcent, a preservative, a flavoring or a coloring agent.

The preparations for parenteral administration can be in the form of a sterile injectable preparation, such as a sterile injectable aqueous or oleaginous suspension. This suspension can be formulated according to methods well known in the art using suitable dispersing or wetting agents and suspending agents. The sterile injectable preparation can also be a sterile injectable solution or suspension in a non-toxic parenterally-acceptable diluent or solvent, such as a solution in 1,3-butanediol. Suitable diluents include, for example, water, Ringer's solution and isotonic sodium chloride solution. In addition, sterile fixed oils can be employed conventionally as a solvent or suspending medium. For this purpose, any bland fixed oil can be employed including synthetic mono or diglycerides. In addition, fatty acids such as oleic acid can likewise be used in the preparation of injectable preparations.

The pharmaceutical compositions can also be in the form of oil-in-water emulsions. The oily phase can be a vegetable oil, such as olive oil or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain sweetening and flavoring agents.

When administered to a mammal, e.g., to an animal for veterinary use or for improvement of livestock, or to a human for therapeutic use, the compositions are administered in isolated form or as the isolated form in a therapeutic composition. As used herein, "isolated" means that the compositions are separated from other components of either (a) a natural source, such as a plant or cell or food, preferably bacterial culture, or (b) a synthetic organic chemical reaction mixture. Preferably, via conventional techniques, the compositions are purified. As used herein, "purified" means that when isolated, the isolate contains at least 95%, preferably at least 98% of the composition.

In some embodiments, the compositions are provided to the subject orally. In other embodiments, the compositions are provided by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems useful in the methods include for example, encapsulation in liposomes, microparticles, microcapsules, capsules, etc., and can be used to administer a compound of the embodiments. In certain embodiments, more than one composition is administered to an individual.

Other modes of administration useful in the methods include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the professional, and will depend in-part upon the site of the condition to be treated. In most instances, administration will result in the release of the compositions into the bloodstream.

In specific embodiments, it can be desirable to administer one or more compositions locally to the area in need of treatment. This can be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of an atherosclerotic plaque tissue Pulmonary administration can also be employed, e.g., by use of an inhaler or nebulizer, and formulation with an aerosolizing agent, or via perfusion in a fluorocarbon or synthetic pulmonary surfactant. In certain embodiments, the compositions can be formulated as a suppository, with traditional binders and vehicles such as triglycerides.

Preferably, the compositions are formulated with a pharmaceutically acceptable vehicle. As used herein, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the embodiments is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compositions of the embodiments and pharmaceutically acceptable vehicles are preferably sterile. Water is a preferred vehicle when the compositions of the embodiments are administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use.

In some embodiments, the compositions are formulated for oral delivery, for example in the form of tablets, lozenges, aqueous or oily suspensions, granules, powders, emulsions, capsules, syrups, or elixirs. Compounds and compositions described herein for oral delivery can also be formulated in foods and food mixes. Orally administered compositions can contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compounds and compositions described herein. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate can also be used. Oral compositions can include standard vehicles such as mannitol, lactose, starch, magnesium stearate, sodium saccharine, cellulose, magnesium carbonate, etc. Such vehicles are preferably of pharmaceutical grade.

In some embodiments, the compositions described herein can be in the form of nutraceutical packs not limited to functional foods, beverages, bars, dietary supplements, capsules, powder form or gelatin form, pharmaceutical packs or kits comprising one or more containers filled with one or more compositions of the embodiments. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound described herein. In another embodiment, the kit comprises a compound described herein and another lipid-mediating compound, glycemic control and antihypertensive drugs, including but not limited to insulin, statin, a thiazolidinedione, or a fibrate or dietary modifications.

The compositions can be assayed in vitro and in vivo, for the desired therapeutic or prophylactic activity, prior to use in humans. For example, in vitro assays can be used to determine whether administration of a specific compound described herein or a combination of compositions of the embodiments are preferred for lowering fatty acid synthesis. The compositions can also be demonstrated to be effective and safe using animal model systems.

Throughout the specification there are references to identifying a subject in need of administration of a composition of the embodiments. The term identification is not intended to be limiting and includes in each instance a belief by the subject that the composition will benefit the subject, self-identification, and identification by third party using various techniques. The identification may be of at least one condition selected from the group consisting of: sarcopenia, muscle atrophy, muscle wasting, muscular dystrophy, insulin resistance, cardiovascular disease, progressive renal disease, end stage renal disease, endothelial dysfunction, left ventricular hypertrophy, cardiac hyperreactivity, dyslipidemia, hyperglycemia, enhanced rennin angiotensin activity, aldosterone syndrome, impaired pressure natriuresis, chronic low grade inflammation, diabetes mellitus, hypertension, atherosclerosis, micoralbuminuria, obesity, depression, Syndrome X, polycystic ovary syndrome, cancer cachexia, spinal injuries, and combinations of any of the foregoing. The identification may be selection of a particular patient population, for example, elderly patients, bed-ridden patients, and/or patients with low-protein diets. The identification may comprise identifying an individual that is taking a composition comprising a compound selected from the group consisting of: steroids, non-steroidal anti-inflammatory compounds, oral contraceptives, implantable steroid contraceptives, hormone replacement therapy, beta blockers, potassium channel openers, immunosuppressive drugs, weight gainer formulations, human growth hormone, testosterone, and combinations thereof. Identification may also include analyzing a patient's family history and/or genetic profile.

In some embodiments, the subject may be elderly, bed-ridden, have a low-protein diet, and/or has one or more of sarcopenia, muscle atrophy, muscle wasting, muscular dystrophy, insulin resistance, cardiovascular disease, progressive renal disease, end stage renal disease, endothelial dysfunction, left ventricular hypertrophy, cardiac hyperreactivity, dyslipidemia, hyperglycemia, enhanced rennin angiotensin activity, aldosterone syndrome, impaired pressure natriuresis, chronic low grade inflammation, diabetes mellitus, hypertension, atherosclerosis, micoralbuminuria, obesity, depression, Syndrome X, polycystic ovary syndrome, cancer cachexia, spinal injuries, and combinations of any of the foregoing. In some embodiments the subject is elderly. In some embodiments, the subject has progressive renal disease or end stage renal disease. In some embodiments, the subject has sarcopenia.

As used herein, the term "treatment" or "treating" refers to an amelioration of a disease or disorder, or at least one discernible symptom thereof. The term "treatment" or "treating" refers to inhibiting the progression of a disease or disorder, either physically, e.g., stabilization of a discernible symptom, or physiologically, e.g., stabilization of a physical parameter, or both.

In certain embodiments, the compositions are provided to a subject, such as a mammal, as a preventative measure against such diseases. As used herein, "prevention" or "preventing" refers to a reduction of the risk of acquiring a given disease or disorder alone or in combination with other clinical condition.

The combination chromium supplementation is useful for the methods for treating obesity and related pathologies, obesity related to complications such as diabetes, diabetes risk factors, leptin resistance, abdominal fat distribution, cardiovascular disease and its related pathologies, cardiovascular and related diseases, such as, for example, hypertrophy, hypertension, congestive heart failure, myocardial ischemia, ischemia reperfusion injuries in an organ, arrhythmia, myocardial infarction, and combinations of any of the foregoing. One embodiment is directed to a method of treating obesity and its associated complications such as diabetes, cardiovascular disease and insulin resistance in a mammal by concurrently administering to the mammal a therapeutically effective amount of a combination chromium supplementation and at least one starch.

The present invention is further disclosed in the following Examples, which are provided for illustrative purposes and are not in any way intended to limit the scope of the invention as claimed.

EXAMPLES

Exemplary Procedures

Double-blind, cross-over design, with twenty subjects (10 men and 10 women), between 22 and 65 are pre-screened using health history questionnaires, vital signs, and blood work. Participants must meet all of the following inclusion criteria in order to participate in the study: Provided voluntary signed and dated informed consent; were in good health as determined by medical history and routine blood chemistries; ages between 22 and 65 (inclusive) years; Body Mass Index of 18.0-29.9 kg/m$^2$; resting systolic blood pressure<140 mm Hg and diastolic blood pressure<90 mm Hg during rested, seated measurements; normal resting heart rate of <90 per minute during rested, seated measurements.

Participants with any of the conditions below are excluded from the study: history of diabetes; history of smoking; history of malignancy in the previous 6 months; prior gastrointestinal bypass surgery (Lapband, etc.); chronic inflammatory condition or disease (Lupus, HIV/AIDS, etc.); known sensitivity or allergy to whey protein or chromium or amylopectin; subjects who currently use, and cannot refrain from using chromium supplements; cannot refrain from consuming protein or amino acid supplements during their participation in this study; will not refrain from resistance training (outside any prescribed training) during the study period; currently participating in another research study with an investigational product; hemoglobin less than 9.5 mg/dl at the screening visit; concomitant use of corticosteroids or testosterone replacement therapy (ingestion, injection, or transdermal), or use of any other anabolic steroid; any other diseases or conditions that would place the subject at increased risk of harm if they were to participate, at the discretion of the medical staff; cannot participate in any resistance training activities more than 2 days per week.

All subjects are provided a particular diet, and asked to maintain their current dietary habits. Each subject's baseline diet is analyzed via NutriBase IX (Clinical Edition) to determine its energy and macronutrient content. Before reporting to the laboratory for subsequent testing, subjects will refrain from exercise for 72 hours, and fasted for at least 8 hours prior to testing.

In addition to the prescribed diet and/or exercise regimen, subjects in the test group are administered a supplement containing chromium picolinate, chromium histidinate, amylopectin, and 10 grams of whey protein. Subjects in the control group are administered a supplement with only amylopectin and 10 grams of whey protein.

Example 1

In the presence of adequate whole protein and/or essential amino acids (EAA), insulin has a stimulatory effect on muscle protein synthesis, whereas in conditions of lower blood EAA concentrations, insulin has an inhibitory effect on protein breakdown. We determined the effect of CrPic/CrHis+amylopectin (CAP) on changes in plasma concentrations of EAA, insulin, and the fractional rate of muscle protein synthesis (FSR). Using a double-blind, cross-over design, ten subjects (6 men, 4 women) consumed 6 g whey protein+2 g of CrPic/CrHis+amylopectin (WCAP) or 6 g whey protein (WP) after an overnight fast. FSR was measured using a primed, continuous infusion of ring-d5-phenylalanine with serial muscle biopsies performed at 2, 4, and 8 hr. Plasma EAA and insulin were assayed by ion-exchange chromatography and ELISA, respectively. After the biopsy at 4 hr, subjects ingested their respective supplement, completed 8 sets of bilateral isotonic leg extension @ 80% of their estimated 1-RM, and a final biopsy was obtained 4 hours later. Both trials increased EAA similarly, with peak levels noted 30 min after ingestion. Insulin tended (P=0.09) to be higher in the WCAP trial. FSR values increased by 32% in WCAP (+0.026%/hr, P<0.001 utilizing either the plasma or intracellular precursor enrichment) and 21% after ingestion of WP (+0.012%/hr, P=NS), respectively. These data indicate that the addition of CrPic/CrHis+amylopectin to a 6 g dose of whey protein increases FSR.

This was an open-label, single dose trial. Ten apparently healthy subjects (men/women=6/4), pre-screened using health history questionnaires, vital signs, and blood work were enrolled in the study. Completed subjects were between the ages of 22 and 34 years old. Research procedures included venous blood draws and vastus lateralis muscle biopsies during a primed, constant infusion of L-[ring-d5]-phenylalanine. The fractional rate of muscle protein synthesis (FSR) was measured using the stable isotope tracer incorporation technique from vastus lateralis muscle biopsies performed 2, 4, and 8 hrs after initiating stable isotope tracer infusion. Blood samples were collected at baseline (time 0) and at specified time points after the beginning of stable isotope tracer infusion (i.e. +30 min, +1 hr, +4 hr, and +8 hr) to assess changes in amino acid concentrations. After the biopsy at 4 hr, a single dose of WCAP was administered orally and a final biopsy was obtained 4 hours later (i.e. 4 hours post-prandial).

Participants met all of the following inclusion criteria in order to participate in the study: Provided voluntary signed and dated informed consent; were in good health as determined by medical history and routine blood chemistries; ages between 21 and 45 (inclusive) years; Body Mass Index of 18.5-29.9 kg/m$^2$; normotensive (resting systolic blood pressure<140 mm Hg and diastolic blood pressure<90 mm Hg) during rested, seated measurements; normal resting heart rate (<90 per minute) during rested, seated measurements.

Participants with any of the conditions below were excluded from the study: history of diabetes; history of smoking; history of malignancy in the previous 6 months; prior gastrointestinal bypass surgery (Lapband, etc.); chronic inflammatory condition or disease (Lupus, HIV/AIDS, etc.); known sensitivity or allergy to whey protein or chromium or amylopectin; subjects who currently use, and cannot refrain from using chromium supplements, or any other dietary ingredient that in the opinion of the research team might affect insulin sensitivity or glucose tolerance; do not or will not refrain from eating animal proteins during their participation in this study; cannot refrain from consuming protein or amino acid supplements during their participation in this study; will not refrain from resistance training during the study period; currently participating in another research study with an investigational product; hemoglobin less than 9.5 mg/dl at the screening visit; concomitant use of corticosteroids or testosterone replacement therapy (ingestion, injection, or transdermal); any other diseases or conditions that would place the subject at increased risk of harm if they were to participate, at the discretion of the medical staff; cannot participate in any resistance training activities more than 2 days per week.

All subjects were asked to maintain their current dietary habits. Each subject's baseline diet was assessed by a 24-hour diet record, and was analyzed via NutriBase IX (Clinical Edition) to determine its energy and macronutrient content (see Table 1 below). Before reporting to the laboratory for subsequent testing, subjects followed their previously recorded 24-hour diet records, refrained from exercise for 72 hours, and fasted for at least 8 hours prior to testing.

TABLE 1

Dietary intake of subjects (N = 10) at baseline.

| Subject #/Gender | Total Calories | CHO (g) | FAT (g) | PRO (g) | CHO (%) | FAT (%) | PRO (%) |
|---|---|---|---|---|---|---|---|
| 01/M | 2641 | 165 | 102 | 264 | 25 | 35 | 40 |
| 02/M | 2067 | 263 | 32 | 180 | 51 | 14 | 35 |
| 03/F | 1905 | 185 | 80 | 109 | 39 | 38 | 23 |
| 04/M | 1873 | 234 | 49 | 121 | 50 | 24 | 26 |
| 05/M | 2839 | 227 | 97 | 262 | 32 | 31 | 37 |
| 06/M | 3104 | 279 | 106 | 256 | 36 | 31 | 33 |
| 07/M | 2312 | 213 | 97 | 144 | 37 | 38 | 25 |
| 08/F | 1399 | 139 | 46 | 104 | 42 | 30 | 28 |
| 09/F | 1730 | 202 | 56 | 108 | 46 | 29 | 25 |
| 10/F | 1326 | 198 | 22 | 82 | 60 | 15 | 25 |

Determination of Muscle Protein Synthesis

Subject Preparation: On the morning of the study and after an overnight fast (8 hrs), an 18-22 gauge polyethylene catheter was inserted into each arm; one was placed in a distal vein for heated blood sampling (5 ml each time point), and another was placed in the forearm for infusion of the stable isotope tracers.

Amino Acid (Isotopic) Tracer: After insertion of peripheral catheters, a primed (5.04 μmol/kg), constant (0.084 μmol/kg/min) infusion of the stable isotope (GRAS substance) ring-d$_5$-phenylalanine was started. Stable isotopes were obtained from Cambridge Isotope Laboratories (Tewksbury, Mass.) and tested for sterility and pyrogenicity (by CIL and the preparing pharmacy—Cantrell Pharmacy). Prior to infusion, the stable isotope was then filtered during infusion through a sterile 0.22 micron (Millipore) filter placed in the infusion line.

Blood Sampling: Blood samples (5 ml) were collected in Lithium Heparin tubes at baseline (time 0) and after the beginning of isotope infusion (4, 4+30, 5, 5+30, 6, 6+30, 7 and 8 hrs) for analysis of amino acid concentrations, and for the analyses of plasma insulin and glucose (4, 4+30, 5, 5+30, 6, 6+30 and 8 hrs). After centrifugation, plasma samples were stored in separate aliquots at −80 degrees C. until analysis.

Muscle Biopsy Procedure: Muscle biopsies from the vastus lateralis were performed after 2, 4, and 8 hrs of tracer infusion. After the biopsy at 4 hr, a single dose of WCAP or the placebo was administered orally under supervision. Muscle biopsies were performed under local anesthesia (using sterile 1% lidocaine, without epinephrine) for normal pain management and under strict sterile procedures. Prior to each muscle biopsy, a sterile field was created on the skin surface using a Betadine skin preparation kit. Then the skin and underlying tissue were injected with local anesthetic (Lidocaine) to minimize pain.

A 5 mm Bergstrom needle was advanced into the muscle through a small (~1 cm) incision produced by a #11 blade disposable scalpel. Immediately after applying suction, a small sample of the muscle (approximately 80-100 mg) was removed with the needle. The sample was cleaned with sterile saline, trimmed of any visible connective tissue, blotted, and then cut into three equal portions. All three samples were immediately frozen in liquid nitrogen and stored at −80° C.

After the biopsy procedure, the skin was cleansed, edges approximated with ¼ inch×1.5 inch adhesive Steri-strips, and a breathable film dressing (Tegaderm) was applied to the site. Firm pressure was maintained until bleeding at the site ceased. To minimize the risk of infection and bruising, an antibiotic ointment and pressure dressing (with self-adhesive elastic bandage) were applied by the medical staff before the subject was released. All subjects were instructed to refrain from exercise for at least 48 hours and to use Tylenol for pain control, as needed.

After qualifying for the study, subjects were assigned to receive, in double-blinded manner, whey protein (6 g) and 2.01 grams of the product (WCAP) or whey protein (6 g) and placebo. Whey supplements were prepared in powdered form, while product (WCAP) and placebo were prepared in capsule form. All supplements were packaged in coded generic containers for double-blind administration.

The Supplement Fact Panel was used below

Chromium—Amylopectin Product

| DIRECTIONS: For adults, take 5 capsules daily. Supplement Facts Serving Size: 5 Capsules (2 grams) Servings Per Container: 15 | | |
| --- | --- | --- |
| | Amount Per Serving | % Daily Value |
| Chromium (from Picolinate and Histidinate) | 1000 mcg | 834% |
| Amylopectin (from waxy maize) | 1790 mg | † |

† Daily Value not established.
Other ingredients: Dicalcium phosphate, microcrystalline cellulose, gelatin, water, magnesium stearate

| Schematic Diagram of Visits | | | |
| --- | --- | --- | --- |
| | Day 0 | Test 1 | Test 2 (5-7 days later) |
| A. Informed Consent | ✓ | | |
| B. Health History Questionnaire | ✓ | | |
| C. Physical Exam and EKG | ✓ | | |
| D. Comprehensive Blood Chemistry* | ✓ | | |
| E. Vitals (HR and BP)** | ✓ | | |
| Height/Body Weight | ✓ | ✓ | ✓ |
| Muscle Biopsies (3 per trial) | | ✓ | ✓ |
| Blood Amino Acid Analyses (9 time points) | | ✓ | ✓ |
| Phenylalanine Tracer Enrichment (8 time points) | | ✓ | ✓ |
| Glucose/Insulin analyses (7 time points) | ✓ | ✓ | |
| Diet Record Analysis | ✓ | ✓ | |
| Side Effect Questionnaire | ✓ | ✓ | |

*includes: glucose, blood urea nitrogen, creatinine, AST, ALT, total bilirubin, alkaline phosphatase, triglycerides, cholesterol, HDL, LDL, sodium, potassium, total protein, albumin, globulin, iron, CBC, platelet count and differential white cell count.
**Enrollment of the subjects into a specific testing order occurred after the research staff cleared the questionnaires, vitals and blood work as being normal or within acceptable limits.

Compliance to product ingestion was confirmed by having all subjects consume their dose of WCAP in the presence of the medical staff. Compliance to diet and physical activity controls (i.e. 24-hr diet duplication, no exercise for 72 hours, 8-hr fast) was confirmed via verbal acknowledgment by all subjects.

Outcome variables (muscle FSR and blood amino acid concentrations) were analyzed via dependent t-tests and one-way ANOVA, respectively, to determine within-trial changes from baseline. Two-way factorial ANOVA (trial×time) was also employed to explore between-trial changes over time. Statistical significance was set at $P<0.05$ and trends defined as $0.051<P<0.10$.

One female subject dropped out prior to the first biopsy due to dizziness during the lidocaine injection procedure. She was promptly replaced with another female subject.

Six males and four females completed the study (see Table 1). The average age, height, and weight of the subjects was: 26.6+/−3.7 years, 175.5+/−10.9 centimeters (69.09 inches), and 78.56+/−17.4 kg (172.8 lbs). Upon screening, normal values were obtained for blood pressure (122/78 mm Hg), heart rate (66 beats per minute), fasting blood sugar (93 mg/dL), fasting insulin (5 mIU/L), and HOMA-IR* (1.2) [* HOMA-IR=fasting insulin ($\mu$U/ml)/22.5*(glucose (mmol/l)); normal value<2 in adults, <3 in children (Keskin et al., 2005)].

Consistent with previous investigations, a robust increase in plasma essential amino acids (EAA) was realized after ingestion of WCAP (as well as with placebo); with peaks levels achieved approximately 30 min post-ingestion (i.e. occurring at 270 min on all graphs). EAA concentrations returned to near baseline (fasted) levels approximately 3 hr post-ingestion. Individual amino acids followed similar responses. Two-way ANOVA revealed no treatment by time interactions for any plasma amino acid responses.

Muscle Fractional Synthesis Rate (FSR): The results indicate that the Active trial (i.e. WCAP) yielded a more robust response (≈32%) in FSR versus the Control trial (21%; P=0.001). Specifically, in the Active trial, pre-treatment $FSR_{pl}$ was 0.0507±0.01% and post-treatment $FSR_{pl}$ was 0.0745±0.016%. In the Control trial, pre-treatment $FSR_{ic}$ was 0.0532±0.023% while post-treatment $FSR_{ic}$ was 0.0647±0.013%. See accompanying graphs on page 20 and 21.

The significant response of the Active trial was achieved in light of similar leucine and essential amino acid concentrations resultant from each treatment. A potential explanation for improved response of the Active trial may lie in its insulinogenic properties. Peak insulin response of the Active trial trended towards significance (p=0.09).

Data quality was quite satisfactory. Fasted and post-intervention FSR values, as well as their intra-subject variability, are reasonable and physiological. Plasma leucine and EAA responses are also representative of 6 grams of quality protein ingestion. Blood insulin indicated a general response to protein ingestion, though the potential difference noted in the Active trial might be attributable to an ingredient particular to this treatment. There was a small issue with subject 6 during the Active trial. Despite repeated analyses and sample processing, a reliable protein-bound enrichment of biopsy 1 was not attainable. The protein-bound enrichments of muscles 2 and 3 for this subject X treatment were commensurate with the group data set, and the calculated FSR for the post-intervention period was similar to the group mean. These data indicate that study conduct was consistent and not responsible for this anomalous finding. Upon questioning the subject, he admitted to dietary non-compliance during the Active trial. For this reason, the ANOVA was performed with 10 subjects the Control trial and 9 in the Active trial. If/when published, it is suggested that this explanation accompany the data/results description.

Potential side effects commonly associated with the consumption of protein/amino acids can include mild gastrointestinal disturbances (burping, nausea, etc.) as well as heart-burn/acid reflux and flatulence. No such effects were noted in this study, nor were there changes in resting vital signs (i.e. heart rate and blood pressure) during the course of the study. Details of the subjects' responses to a Symptom Questionnaire are provided in Table 2 and information on adverse events is detailed in Table 3.

TABLE 2

Symptom Questionnaire Responses

| | Subject #- | | | | | | | | | |
|---|---|---|---|---|---|---|---|---|---|---|
| | 01 | 02 | 03 | 04 | 05 | 06 | 07 | 08 | 09 | 10 |
| Trial Questions: | A/B | A/B | A/B | A/B | A/B | A/B | A/B | A/B | A/B | A/B |
| Did you have any difficulty adhering to the supplementation protocol? | NO | NO | NO | NO | NO | NO | NO | NO | NO | NO |
| Did you notice anything different with any of the following?<br>a. your training outside the study;<br>b. appetite;<br>c. thirst;<br>d. skin;<br>e. upset stomach;<br>f. diarrhea;<br>g. gas or flatulence;<br>h. headache;<br>i. sex drive;<br>j. sleepiness;<br>k. nervousness or clarity of thought;<br>l. aggression;<br>m. muscle cramping;<br>n. other | NO | NO | NO | NO | NO | NO | NO | NO | NO | NO |

TABLE 3

Adverse Event Reporting

| | Subject | | | | | | | | | | |
|---|---|---|---|---|---|---|---|---|---|---|---|
| | 01 | 02 | 03 | 04 | 05 | 06 | 07 | 08 | 09 | 10 | *D/O #1 |
| Adverse Event (yes/no) | NO | NO | yes | NO | NO | | | NO | | | YES |
| Details of adverse event (if yes) | | | | | | | | | | | |
| Event | | | Numbness/ swelling | | | | | | | | dizziness |
| Onset date | | | Apr. 13, 2015 | | | | | | | | Apr. 2, 2015 |
| Onset time | | | 8:00 am | | | | | | | | 10:30 am |
| Resolve date | | | Apr. 17, 2015 | | | | | | | | Apr. 2, 2015 |
| Resolve time | | | 8:00 am | | | | | | | | 11:00 am |
| Continuing at end of study (yes/no) | | | No | | | | | | | | NO |
| Intensity (1: mild 2: moderate 3: severe) | | | 1 | | | | | | | | 1 |
| Relationship to study treatment (1: not related 2: unlikely 3: possibly 4: probably 5: definite) | | | 2 | | | | | | | | 1 |
| Treatment action taken (1: none 2: medication 3: hospitalization 4: discontinuation 5: other) | | | 5 ice and massage | | | | | | | | 4 |

TABLE 3-continued

| | Adverse Event Reporting | | | | | | | | | | |
|---|---|---|---|---|---|---|---|---|---|---|---|
| | Subject | | | | | | | | | | |
| | 01 | 02 | 03 | 04 | 05 | 06 | 07 | 08 | 09 | 10 | *D/O #1 |
| Relationship to study product | | | No | | | | | | | | NO |
| Serious | | | No | | | | | | | | NO |

*D/O = drop out

In summary, these data are consistent with a within-group effect for the Active trial increasing the muscle FSR response, whereas the Control trial did not demonstrate such a within group effect by 1-way ANOVA. An interim power analysis, utilizing the data obtained thus far suggests that a total sample size of 14-17 subjects would provide 80% power for detecting a significant difference (if one exists) for this within-subject, 2-trial crossover design. Our recommendation would be for an additional 5 subjects enrolled if the goal is to show a significant, comparative difference between treatments. Future efforts should be directed towards a more chronic administration of WCAP on changes in clinical endpoints (i.e., loss/gain of lean mass, functional outcomes, adaptations to structured exercise, etc.). Further, relatively small dose burden of the investigational product lends itself to testing with a broad range of products and delivery systems in circumstances where the anabolic response of skeletal muscle is desired.

Example 2

Example 2 is conducting using the general procedures described herein. DOMS: Using a comparison model with 2 independent variables (control and WCAP) and 6 dependent variables (maximal isometric and isokinetic voluntary strength, range of motion, upper arm circumference, plasma creatine kinase activity, and muscle soreness). A 2-way repeated-measures analysis of variance and paired t-tests are used to examine differences in changes of the dependent variable over time (before, immediately and 30 minutes after exercise, and 1, 2, 3, 4, 7, 10, and 14 days post-exercise) between control and WCAP conditions.

Twenty healthy subjects (10 men and 10 women) with no history of upper arm injury and no experience in resistance training. In the single-blind study, the subjects are separated into control and WCAP groups, and each subject performs 10 sets of 6 maximal isokinetic (90°·s-1) eccentric actions of the elbow flexors with each arm on a dynamometer, separated by 2 weeks. The control group receives a combination of whey protein and amylopectin (control), while the WCAP group receives a combination of whey protein and amylopectin with chromium histidinate and chromium picolinate. The two combinations are iso-volumic and are equivalent in protein and carbohydrate content.

Maximal voluntary isometric and isokinetic elbow flexor strength, range of motion, upper arm circumference, plasma creatine kinase activity, and muscle soreness are measured. Delayed-onset muscle soreness is significantly less for the WCAP group for peak soreness in extending the elbow joint and palpating the brachioradialis muscle. Soreness while flexing the elbow joint and palpating the brachialis muscle is also less in the WCAP group. WCAP has significant effects on plasma creatine kinase activity, with a lower peak value at 4 days post-exercise, and upper arm circumference, with a smaller increase than the control at 3 and 4 days post-exercise. Significant effects of WCAP on recovery of muscle strength is also evident. WCAP is also effective in alleviating DOMS, and reducing post-exercise muscle swelling, and recovering muscle function.

Example 3

Aerobic Exercise Recovery: Nine male, endurance-trained cyclists perform an interval workout followed by 4 hr. of recovery, and a subsequent endurance trial to exhaustion at 70% $VO_2$ max, on three separate days.

Immediately following the first exercise bout and 2 hr. of recovery, subjects drink iso-volumic amounts of WCAP, protein and fluid replacement drink (FR), or carbohydrate replacement drink (CR), in a single-blind, randomized design. Carbohydrate content is equivalent for WCAP and CR and protein content is equivalent for WCAP and FR. Time to exhaustion (TTE), average heart rate (HR), rating of perceived exertion (RPE), and total work (WT) for the endurance exercise were compared between trials. TTE and WT are significantly greater for the WCAP group compared to the FR and CR groups. This suggests that WCAP is an effective recovery aid between two exhausting aerobic exercise bouts, and that WCAP increases exercise stamina.

Example 4

Recovery from Resistance Exercise: WCAP supplementation maintains a short-term net anabolic hormonal profile and decreases muscle cell damage during periods of high-intensity resistance training (overreaching), thereby enhancing recovery and decreasing the risk of injury and illness.

Twenty previously resistance trained males are randomly assigned to either a WCAP or placebo group (receiving an equal amount of whey protein and amylopectin as the WCAP group). Subjects consume the supplement for 3 weeks before commencing a fourth week of supplementation with concomitant high-intensity total-body resistance training (overreaching) (3 3 6-8 repetitions maximum, 8 exercises). Blood is drawn prior to and after supplementation, then again after 2 and 4 days of training. Serum is analyzed for testosterone, cortisol, and creatine kinase. Serum testosterone levels are significantly higher, and cortisol and creatine kinase levels are significantly lower in the WCAP group during and following resistance training.

This suggests that WCAP supplementation produces a net anabolic hormonal profile while attenuating training-induced increases in muscle tissue damage. Athletes' nutrient intake, which periodically increases amino acid intake to reflect the increased need for recovery during periods of overreaching, may increase subsequent competitive performance while decreasing the risk of injury or illness.

Example 5

Increasing Muscle Mass: Using a protocol, similar to that described above, subjects are instructed to follow a diet and exercise regimen for 4 weeks, including resistance training three days per week. At the completion of the study, subjects' body mass and body fat percentage are measured. The test group shows an average of about 5% more muscle mass than the control group.

Example 6

Increasing the Rate of Muscle Hypertrophy: Using the standard protocol, described above, subjects are instructed to follow a diet and exercise regimen for 4 weeks, including resistance training three days per week. At the completion of the study, the circumference of subjects' biceps, quadriceps, and chest are measured. The test group shows an average increase in circumference of about 5% relative to the control group.

Example 7

Increasing the Muscle Uptake of Branched Chain Amino Acids: Using the standard protocol, described above, subjects are instructed to follow a diet and exercise regimen for 4 weeks, including resistance training three days per week. Once each week, a muscle biopsy is obtained (according to the procedure described in Example 1), one hour after administration of the supplement. One biopsy is obtained from each arm and leg, for a total of four biopsies over the four week trial. The test group shows an average increase in cellular levels of branched chain amino acids (leucine, isoleucine, and valine) of about 15% relative to the control group.

Example 8

Decreasing Muscle Soreness: Using the standard protocol, described above, subjects are instructed to follow a diet and exercise regimen for 4 weeks, including resistance training three days per week. However, the subjects in this trial also self-identify as exercise naiver (e.g., 0 to 1 bouts of intense exercise and/or resistance training per week). Subjects fill out a questionnaire regarding their soreness level prior to beginning the trial, and then each day throughout the trial. The test group reports 25% less soreness relative to the control group.

Example 9

Process for Making Chromium, Starch, and Protein Compositions: The protein source(s) and the starch(es) are mixed in water to form a wet blend. The wet blend is then spray dried, followed by dry mixing with chromium picolinate and chromium histidinate. In an alternative process the ingredients are simply dry blended.

Example 10

The subject rats were divided into nine groups: Exercise alone, 0.465 grams whey protein per kilogram of body weight (g/kg), 1.55 g/kg whey protein, 2.33 g/kg whey protein, 3.1 g/kg whey protein, 0.465 g/kg WCAP, 1.55 g/kg WCAP, 2.33 g/kg WCAP, and 3.1 g/kg WCAP. The dose of protein, using human doses converted to rate using a conversion factor to rat of 6.2, provides the following: 0.465 grams in the study is equivalent to a human dose of 6 grams; 1.55 g is equivalent to 20 grams; 2.33 g is equivalent to 20 grams; and 3.1 g is equivalent to 40 grams. See Nair and Jacob, *J. Basic Clin. Pharm.*, Vol. 7, No. 2, pp. 27-31 (2016).

The results demonstrate a ceiling of FSR at a dose of 2.33 g/kg of protein alone (FIG. 18). Administration of WCAP provided an unexpectedly significant increase in FSR even at protein levels over the maximum FSR achieved with protein alone (FIG. 18). Thus, ingestion of protein as WCAP provides FSR levels greater than the maximum FSR levels observed with protein alone (FIG. 19, vertical arrow). Likewise, the FSR of lower doses of WCAP were also unexpectedly enhanced, demonstrating equivalent FSR to levels achieved with substantially higher doses of protein alone (FIG. 18). For example, 0.465 g/kg WCAP increased FSR up to levels observed with 1.55 g/kg of whey protein alone. Accordingly, ingestion of 0.465 g/kg WCAP provides an equivalent FSR to ingestion of 3.33-fold more protein alone. Surprisingly, significantly less total protein intake (as WCAP) is required to achieve equivalent FSR rates compared to protein alone (FIG. 19, horizontal arrow).

The methods, compositions, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that varying substitutions and modifications can be made to the invention disclosed herein without departing from the scope and spirit of the invention.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,'

'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method for increasing muscle mass, comprising: providing an effective amount of a chromium complex and an amount of a starch in combination with an amount of a protein to a subject, wherein:
   the amount of a starch is not part of an excipient starch, and
   the chromium complex is selected from the group consisting of chromium picolinate, chromic tripicolinate, chromium nicotinate, chromic polynicotinate, chromium chloride, chromium histidinate, chromium trihistidinate, and chromium yeast, or a combination thereof.

2. The method of claim 1, further comprising providing a compound selected from the group consisting of caffeine, creatine, creatine hydrochloride, creatine monohydrate, taurine, guarana, vitamin C, vitamin $B_1$, vitamin $B_2$, vitamin $B_3$, vitamin $B_5$, vitamin $B_6$, vitamin $B_7$, vitamin $B_9$, and vitamin $B_{12}$, or a combination thereof.

3. The method of claim 1, wherein the protein is a whey protein.

4. The method of claim 3, wherein the whey protein is hydrolyzed.

5. The method of claim 1, wherein the protein comprises at least one essential amino acid.

6. The method of claim 5, wherein the at least one essential amino acid is leucine.

7. The method of claim 1, wherein the starch of the amount of a starch is amylopectin.

8. A method of stimulating muscle synthesis, comprising:
providing an effective amount of a chromium/amylopectin complex in combination with an amount of a protein, wherein the amylopectin in the chromium/amylopectin complex is not an excipient.

9. A method of increasing muscle power comprising:
providing a composition having a chromium complex to provide a first bioavailable amount of chromium to a subject and an amount of a starch source to provide a second bioavailable amount of starch to the subject; and
providing an amount of a protein to the subject, wherein:
the amount of a starch is not part of an excipient starch, and
the chromium complex is selected from the group consisting of chromium picolinate, chromic tripicolinate, chromium nicotinate, chromic polynicotinate, chromium chloride, chromium histidinate, chromium trihistidinate, and chromium yeast, or a combination thereof.

10. The method of claim 1, wherein the chromium complex comprises chromium picolinate and chromium histidinate.

11. The method of claim 1, wherein the chromium complex comprises chromium histidinate and the starch of the amount of a starch is amylopectin.

12. The method of claim 1, wherein the chromium complex comprises chromium picolinate and the starch of the amount of a starch is amylopectin.

13. The method of claim 1, wherein the chromium complex comprises chromium nicotinate and the starch of the amount of a starch is amylopectin.

14. The method of claim 1, wherein the chromium complex comprises chromium picolinate and chromium histidinate, and wherein the starch of the amount of a starch is amylopectin.

* * * * *